(12) United States Patent
Curtiss, III et al.

(10) Patent No.: US 7,341,860 B2
(45) Date of Patent: Mar. 11, 2008

(54) REGULATED ANTIGEN DELIVERY SYSTEM (RADS)

(75) Inventors: Roy Curtiss, III, St. Louis, MO (US); Steven A. Tinge, Belleville, IL (US)

(73) Assignees: Washington University, Saint Louis, MO (US); AVANT Immunotherapeutics, Inc., Needham, MA (US)

( * ) Notice: Subject to any disclaimer, the term of this patent is extended or adjusted under 35 U.S.C. 154(b) by 451 days.

(21) Appl. No.: 10/924,574

(22) Filed: Aug. 24, 2004

(65) Prior Publication Data

US 2005/0106176 A1    May 19, 2005

Related U.S. Application Data

(62) Division of application No. 09/560,539, filed on Apr. 28, 2000, now Pat. No. 6,780,405.

(51) Int. Cl.
*C12N 1/20*    (2006.01)
*C12P 21/06*    (2006.01)

(52) U.S. Cl. .................... 435/252.3; 435/69.1
(58) Field of Classification Search ............. 435/252.3, 435/69.1
See application file for complete search history.

(56) References Cited

U.S. PATENT DOCUMENTS

| | | | |
|---|---|---|---|
| 4,190,495 A | 2/1980 | Curtiss, III |
| 4,424,065 A | 1/1984 | Langhoff et al. |
| 4,837,151 A | 6/1989 | Stocker |
| 4,888,170 A | 12/1989 | Curtiss, III |
| 5,015,573 A | 5/1991 | Yarranton et al. |
| 5,028,530 A | 7/1991 | Lai et al. |
| 5,278,744 A | 1/1994 | Geboers et al. |
| 5,294,441 A | 3/1994 | Curtiss, III |
| 5,389,368 A | 2/1995 | Gurtiss, III |
| 5,424,065 A | 6/1995 | Curtiss, III et al. |
| 5,468,485 A | 11/1995 | Curtiss, III |
| 5,656,488 A | 8/1997 | Curtiss, III |
| 5,672,345 A | 9/1997 | Curtiss, III |
| 5,674,746 A | 10/1997 | Morris |
| 5,840,483 A | 11/1998 | Curtiss, III |
| 5,855,879 A | 1/1999 | Curtiss, III |
| 5,855,880 A | 1/1999 | Curtiss, III |
| 5,888,790 A | 3/1999 | Cahoon et al. |
| 6,024,961 A | 2/2000 | Curtiss, III |

FOREIGN PATENT DOCUMENTS

WO    WO 96/40947    12/1996

OTHER PUBLICATIONS

Amann et al., *Gene*, 40: 183-190 (1985).
Buchanan et al., *Infect. Immun.*, 55: 1000-1003 (1987).
Bumann et al., *FEMS Immunology and Medical Microbiology*, 27(4): 357-364 (2000).
Buxton et al., *J. Gen. Microbiol.*, 120: 283-293 (1980).
Curtiss et al., *Infect. Immun.*, 55: 3035-3043 (1987).
Dul et al., *J. Bacteriol.*, 15: 12121-12214 (1973).
Galan et al., *Gene*, 94: 29-35 (1990).
Jagusztyn-Kryincka et al., *J. Gen. Microbiol.*, 128: 1135-1145 (1982).
Kahn et al., *Meth. Enzymol.*, 68: 268-280 (1979).
Klecker et al., *J. Mol. Bio.*, 116: 125-159 (1977).
Nakayama et al., *Bio/technology*, 6: 693-697 (1988).
Ulmer et al., *Curr. Opin. Immunol*, 8: 531-536 (1996).
Umbarger et al., *Ann. Rev. Biochem.*, 47: 533 (1987).
Wright et al., *Gene*, 49(3): 311-321 (1986).

*Primary Examiner*—Mark Navarro
(74) *Attorney, Agent, or Firm*—Yankwich & Associates, P.C.; Leon R. Yankwich; Micahel R. Wesolowski, Esq.

(57) ABSTRACT

We describe a regulated antigen delivery system (RADS) that has (a) a vector that includes (1) a gene encoding a desired gene product operably linked to a control sequence, (2) an origin of replication conferring vector replication using DNA polymerase III, and (3) an origin of replication conferring vector replication using DNA polymerase I, where the second origin of replication is operably linked to a control sequence that is repressible by a repressor. The RADS microorganism also has a gene encoding a repressor, operably linked to an activatible control sequence. The RADS described provide high levels of the desired gene product after repression of the high copy number origin of replication is lifted. The RADS are particularly useful as live bacterial vaccines. Also described is a delayed RADS system, in which there is a delay before the high copy number origin is expressed after the repression is lifted. The delayed RADS is also particularly useful for live bacterial vaccines. Also described are several control elements useful for these systems, as well as methods for providing immunity to a pathogen in a vertebrate immunized with the RADS microorganisms.

23 Claims, 23 Drawing Sheets

Figure 6. pYA3484

Figure 7. pYA3485

Figure 11. Modification of pMEG-771 to include a *lacRB* (LacI repressor binding) site after P22 P R right before pUCrep to yield pYA3535

Figure 11. Modification of pMEG-771 to include a *lacRB* (LacI repressor bindng) site after P22 P R right before pUC *RNAII* to yield pYA3535

Figure 12. Modification of pMEG-771 to replace *asd* gene with *araC* P$_{BAD}$ *c2* GTG*asd*

Figure 20. pYA3530 with *araC* P$_{BAD}$ GTG *asd*

Figure 21. pYA3531 with *araC* P$_{BAD}$ P22 *c2* GTG *asd*

Figure 22. pMEG-771 modified with asd gene replaced by araC P$_{BAD}$ c2 GTGasd and P$_{trc}$ MCS 5ST1T2 replaced by eucaryotic CMV BGH pA expression cassette from pVAX1 plasmid

REGULATED ANTIGEN DELIVERY SYSTEM (RADS)

This application is a divisional application of U.S. Ser. No. 09/560,539, filed Apr. 28, 2000, now U.S. Pat. No. 6,780,405.

REFERENCE TO GOVERNMENT GRANT

This invention was made with government support under Grant Numbers DE06669, AI 24533, AI 38599, and USDA 9902097. The government has certain rights in this invention.

BACKGROUND OF THE INVENTION (1) Field of the Invention

The invention relates to materials and methods for preparing vaccines and recombinant DNA expression products, and more particularly to genetically engineered attenuated pathogenic microorganisms that are useful for expressing antigens and other recombinant products encoded on plasmid-borne genes.

(2) Description of the Related Art

References Cited:
Amann and Brosius (1985), *Gene* 40:193.
Ausubel et al. (1995), SHORT PROTOCOLS IN MOLECULAR BIOLOGY, John Wiley and Sons.
Berg and Howe, Eds. (1989) MOBILE DNA, American Society for Microbiology, Washington, D.C.
Berger and Kimmel, Eds. (1987), GUIDE TO MOLECULAR CLONING TECHNIQUES, Methods in Enzymology (Volume 152), Academic Press, San Diego
Buchanan et al (1987), *Infect. Immun.* 55:1000.
Buxton et al (1980), *J. Gen. Microbiol.* 120:283.
Cossart et al. Eds. (2000), CELLULAR MICROBIOLOGY, ASM Press, Washington, D.C.
Curtiss and Kelly (1987), *Infect. Immun.* 55:3035.
Davis, Dulbecco, Eisen, Ginsberg, and Wood (1980), MICROBIOLOGY, Third Edition (Harper and Row).
Dul et al (1973), *J. Bacteriol.* 115:1212.
Galan et al (1990), *Gene*, 94:29-35.
Gebhardt et al. Eds. (1994) METHODS FOR GENERAL AND MOLECULAR BACTERIOLOGY, American Society for Microbiology, Washington, D.C.
Jagusztyn-Krynicka, et al (1982), *J. Gen. Microbiol.* 128:1135.
Kahn et al (1979), *Meth. Enzymol.* 68:268.
King and Stansfield, (1985), DICTIONARY OF GENETICS, Oxford University Press
Kleckner et al (1977), *J. Mol. Biol.* 116:125.
Madigan et al. (2000), BROCK BIOLOGY OF MICROORGANISMS, ninth ed., Prentice Hall
Maloy et al. (1996), GENETIC ANALYSIS OF PATHOGENIC BACTERIA, Cold Spring Harbor Laboratory Press.
METHODS IN ENZYMOLOGY (Academic Press, Inc.);
Miller, Jeffrey H. (1992) A SHORT COURSE IN BACTERIAL GENETICS, Cold Spring Harbor Laboratory Press
Miller et al. Eds (1994) MOLECULAR GENETICS OF BACTERIAL PATHOGENESIS; ASM Press, Washington, D.C.
Nakayama et al (1988), *Biotechnol.* 6:693.
Neidhardt et al., Eds. (1996), *ESCHERICHIA COLI* AND *SALMONELLA:* CELLULAR AND MOLECULAR BIOLOGY, second ed., ASM Press, Washington D.C., especially Chapters 110, 133, 135, 141.
Ogra et al., Eds. (1999), MUCOSAL IMMUNOLOGY, second ed., Academic Press, San Diego.
Paul, Ed. (1999), FUNDAMENTAL IMMUNOLOGY, fourth ed., Philadelphia: Lippincott-Raven
Peters (1993), BIOTECHNOLOGY, A Guide to Genetic Engineering, Wm. C. Brown Publishers
Sambrook et al. (1989), MOLECULAR CLONING, A LABORATORY MANUAL, second ed., Cold Spring Harbor Laboratory Press.
Snyder and Champness (1997), MOLECULAR GENETICS OF BACTERIA, ASM Press, Washington, D.C.
Ulmer et al. (1996) *Curr. Opin. Immunol.* 8:531-6
Umbarger (1978), *Ann. Rev. Biochem.* 47:533
U.S. Pat. No. 4,190,495.
U.S. Pat. No. 4,424,065.
U.S. Pat. No. 4,888,170.
U.S. Pat. No. 5,294,441.
U.S. Pat. No. 5,278,744.
U.S. Pat. No. 5,389,368.
U.S. Pat. No. 5,424,065.
U.S. Pat. No. 5,468,485.
U.S. Pat. No. 5,656,488.
U.S. Pat. No. 5,672,345.
U.S. Pat. No. 5,840,483.
U.S. Pat. No. 5,855,879.
U.S. Pat. No. 5,855,880.
U.S. Pat. No. 5,888,790.
U.S. Pat. No. 6,024,961.

Related Art

Genetically engineered microorganisms have widespread utility and importance. One important use of these microorganisms is as live vaccines to produce an immune response. Live vaccines are most effective when they produce high levels of antigen. However, the synthesis of a high level expression of a recombinant antigen may be deleterious to the microorganism. Because of this, regulated (as opposed to constitutive) expression systems have been identified and utilized where the recombinant gene of interest is operably linked to control elements that allow expression of significant amounts of the recombinant gene only when it is induced, derepressed or activated. Examples include the cspA gene promoter, the phoA gene promoter, $P_{BAD}$ (in an araC-$P_{BAD}$ system), the trp promoter, the tac promoter, the trc promoter, $\lambda P_L$, P22 $P_R$, mal promoters, and the lac promoter. These promoters mediate transcription at low temperature, at low phosphate levels, in the presence of arabinose, in the presence of at low tryptophan levels, and in the presence of lactose (or other lac inducers.)

One important use of genetically engineered microorganisms is as a live vaccine for inducing immunity. See, e.g., U.S. Pat. Nos. 6,024,961; 4,888,170; 5,389,368; 5,855,879; 5,855,880; 5,294,441; 5,468,485; 5,387,744; 5,840,483, 5,672,345; 5,424,065; 5,378,744; 5,888,790; 5,424,065; 5,656,488; 5,006,335; 5,643,771; 5,980,907; 5,851,519; and 5,527,529, all of which are incorporated by reference. When the genetically engineered microorganism is to be utilized as a vertebrate live vaccine, certain considerations must be taken into account. To provide a benefit beyond that of a nonliving vaccine, the live vaccine microorganism must attach to, invade, and survive in lymphoid tissues of the vertebrate and expose these immune effector sites in the vertebrate to antigen for an extended period of time. By this continual stimulation, the vertebrate's immune system becomes more highly reactive to the antigen than with a nonliving vaccine. Therefore, preferred live vaccines are attenuated pathogens of the vertebrate, particularly pathogens that colonize the gut-associated lymphoid tissue (GALT) or bronchial-associated lymphoid tissue (BALT). An additional advantage of these attenuated pathogens over nonliving vaccines is that these pathogens have elaborate mechanisms to gain access to lymphoid tissues, and thus efficient exposure to the vertebrate's immune system can be expected. In contrast, nonliving vaccines will only provide an immune stimulus if the vaccine is passively exposed to the immune system, or if host mechanisms bring the vaccine to the immune system.

As described in U.S. Pat. No. 5,888,799, for example, pathogenic bacteria can be attenuated by introduction of mutations so that upon infection of an animal host disease symptomology is not elicited, yet the bacteria retain the ability to attach to, invade, and colonize lymphoid tissues within the animal host for a sufficient time to induce an immune response against the attenuated bacteria. These attenuated bacterial vaccine strains can be genetically engineered to express foreign antigens encoded by genes on plasmid vectors or inserted into the chromosome that are derived from heterologous pathogenic bacteria, viruses, fungi, or parasites. These recombinant attenuated bacterial vaccines can be delivered as live vaccines to mucosal surfaces in an immunized individual so that the recombinant bacteria serve as a factory within these lymphoid tissues of the immunized vertebrate, producing the foreign antigen and eliciting a primary and/or protective immune response enabling the immunized animal host to survive infection by the pathogen whose antigen is expressed by the recombinant attenuated bacterial vaccine.

Bacteria can be attenuated by introducing mutations that permit environmental regulation of surface molecule synthesis such as lipopolysaccharides in gram-negative microorganisms as affected by a galE mutation (U.S. Pat. No. 5,006,335). Bacteria can also be attenuated by introduction of mutations that impose specific nutritional requirements, such as for constituents of nucleic acids such as purines, constituents of the cell wall such as diaminopimelic acid (DAP) (U.S. Pat. No. 4,888,170), or that impose requirements for aromatic amino acids and vitamins derived therefrom, such as caused by aro mutations (U.S. Pat. No. 5,643,771). Still other means of attenuation are achieved by mutating genes affecting global regulation of other genes. Thus mutants with mutations in the genes for adenylate cyclase, cya, and the cAMP receptor protein, crp, are attenuated and immunogenic (U.S. Pat. Nos. 5,294,441; 5,389, 368; 5,468,485; 5,855,879 and 5,855,880). Similarly, mutations in the phoPQ two-component regulatory system (U.S. Pat. No. 5,424,065) and mutations such as ompR (U.S. Pat. No. 5,527,529), hemA Benjamin et al., 1991, *Microb. Pathog.* 11:289-295), and htrA (U.S. Pat. No. 5,980,907) have also been used to render bacteria attenuated yet immunogenic. All mutants of pathogenic bacteria that are attenuated are not necessarily immunogenic to the same degree. It is therefore possible to introduce mutations such as rpoS which render bacteria attenuated, but impair the ability of the attenuated bacteria to colonize lymphoid tissues, thus reducing the immunogenicity of the bacteria. See U.S. Pat. No. 6,024,961. Thus, some attenuation mechanisms hyperattenuate the vaccine, precluding the candidate vaccine from either reaching or persisting in lymphoid tissues to a sufficient extent or duration to permit induction of a protective immune response to the wild-type pathogen whose antigen is expressed by the recombinant attenuated bacterial vaccine.

Since immune responses induced to expressed foreign antigens are proportional to the levels of antigen expressed by the recombinant attenuated bacterial vaccine (Doggett et al., 1993, *Infect. Immun.* 61:1859-1866; Schodel et al., 1994, *Infect. Immun.* 62:1669-1676; Srinivasan et al, 1995, *Biol. Reprod.* 53:462-471), the placement of the gene for the foreign antigen on a multi-copy plasmid vector is much preferable to the insertion of the gene for the foreign antigen into the chromosome of the attenuated bacterial vaccine vector. This is because the level of foreign antigen expression is generally proportional to the number of copies of the gene for the foreign antigen expressed within the attenuated bacterial host.

Since plasmid-containing recombinant attenuated bacterial vaccines produce large amounts of antigen that provides no advantage to the vaccine, the plasmid vectors are often lost over time after immunization (Curtiss et al, 1988, *Vaccine* 6:155-160). In many cases, ten percent or less of the recombinant attenuated bacterial vaccine isolated from the immunized vertebrate retains the plasmid after three or four days. When this plasmid loss occurs, the immune response is directed more against the attenuated bacterial host vaccine itself rather than against the expressed foreign antigen. This problem was solved by the establishment of balanced-lethal host-vector systems as described in U.S. Pat. Nos. 5, 672, 345 and 5,840,483. In that system, a mutation is introduced into the chromosome of the attenuated bacterial vaccine to preclude synthesis of an essential cell wall constituent, diaminopimelic acid or DAP, which is not prevalent in the environment and is totally absent in animal tissues. In the absence of DAP, the DAP-requiring bacteria undergoes DAP-less death and lysis. The bacterium also contains a plasmid vector comprising a gene complementing the mutation in the chromosome. The plasmid-containing strain is thus able to synthesize DAP and survive in the absence of an exogenous DAP supply, as occurs in an immunized vertebrate. Colonization of internal lymphoid organs in the immunized vertebrate can then occur. One such system employs deletion mutations for the gene for β-aspartate semialdehyde dehydrogenase, the asd gene, and plasmid vectors that would contain the wild-type asd gene in addition to the elements causing expression of a foreign antigen (Nakayama et al., 1988, *Bio/Tech.* 6:693-697; Galan et al., 1990, *Gene* 94:29-35). Aside from the Asd$^+$ plasmid vector encoding the foreign antigen, these Δasd bacterial strains also contain attenuating mutations as described above. When orally administered, these balanced-lethal host-vector vaccines effectively attach to, invade, and colonize lymphoid tissues similar to a bacterium attenuated in the same manner but not expressing the foreign antigen. An important additional benefit of this balanced-lethal host-vector system is the absence of antibiotic resistance gene on the plasmid vector, since live vaccines are not permitted to contain such genes.

As stated above, the level of immune response to a foreign antigen is generally proportional to its level of expression by the recombinant attenuated bacterial vaccine. Unfortunately, overexpression of a foreign antigen is often toxic such that it reduces the rate of growth and therefore the ability of the attenuated bacterial vaccine to colonize lymphoid tissues. As a consequence, the immunogenicity is much diminished. For this reason, it has therefore been necessary to have a balance between the ability of the vaccine to colonize and grow in lymphoid tissues with its ability to produce the foreign antigen.

Another issue of importance in the use of recombinant attenuated bacterial vaccines is their potential, after administration to an animal or human, to be shed in feces and survive in the environment so as to potentially lead to immunization of individuals in which immunization is not desired. This issue is particularly important with agricultural vaccines that might be administered in the feed and/or drinking water or by spray such that the vaccine could persist in the environment and expose other animals to that vaccine other than the animal species desired to be immunized. We therefore designed an environmentally limited viability system (ELVS) for recombinant attenuated bacterial vaccine constructions as described in WO96/40947, incorporated herein by reference. In some embodiments of that invention, vaccine strains were constructed that, in a permissive environment, express essential genes and not express lethal genes, but upon entering a non-permissive environment, such as the ambient temperature following shedding of fecal matter, would cease expressing essential genes and commence expressing lethal genes, leading to the death of the vaccine construct. In other embodiments, the containment features of the vaccine relating to the expression of essential genes and the non-expression of lethal genes in a permissive environment, such as during growth of the vaccine strain in a fermenter, were extended for a period of time after the vaccine strain entered a non-permissive environment, such as the immunized animal host. Such delayed onset environmentally limited viability systems enable the vaccine to attach to, invade, and colonize lymphoid tissues prior to the onset of death brought about by non-expression of essential genes and expression of lethal genes. Although many examples of essential genes and lethal genes are described in WO96/40947, a preferred regulated essential gene therein is the asd gene encoding β-aspartate semialdehyde dehydrogenase, an enzyme necessary for the biosynthesis of DAP, which is an essential constituent of the rigid layer of the bacterial cell wall and is not available in the environment, and especially in animal hosts. The preferred lethal genes therein are those derived from a bacterial virus that lead to lysis of the bacterium when expressed from within the cytoplasm of the microorganism. One way that biological containment is achieved in those inventions is through the employment of a runaway plasmid vector that serves as both a balanced-lethal host-vector system (to maintain the plasmid) and as an ELVS to provide biological containment. As disclosed therein, in the permissive environment (e.g., a fermenter) the bacteria would maintain a very low plasmid copy number and even turn off the expression of the plasmid-encoded foreign antigen. However, at some time after entering a non-permissive environment (e.g., the immunized animal host), the system causes plasmid copy number to increase very significantly, increasing the number of copies of the lethal genes for phage induced lysis. Since the copy number of the gene specifying the foreign antigen is increased, overproduction of the foreign antigen occurs at a time near the time when the bacterium might die by lysis to liberate the foreign antigen and thus augment the induction of an immune response.

Based on the above discussion, there is a need for a live vaccine that is able to effectively colonize the inoculated animal and grow in the lymphoid tissues without causing disease, yet still have the capacity to produce large amounts of antigen in vivo to induce an effective immune response. The present invention addresses that need through the utilization of regulated antigen delivery systems (RADS) based on the use and function of runaway vectors (RAVs).

SUMMARY OF THE INVENTION

Briefly, therefore, the inventors have succeeded in discovering that a novel Regulated Antigen Delivery System (RADS), comprising a novel runaway vector (RAV) and at least one activatible chromosome-derived repressor, in which the copy number of an extrachromosomal vector increases greatly in response to the derepression of the vector caused by the withdrawal of the activating stimulus, can be advantageously utilized in bacterial expression systems, preferably live bacterial vaccines that are attenuated derivatives of pathogenic microorganisms. The derepressible runaway characteristic of the RADS is derived from the chromosomal activatible repressors in combination with elements of the RAV. The essential elements of the RAV are (a) a first origin of replication (ori) conferring a low copy number, where the first ori preferably confers vector replication using DNA polymerase III; (b) a second ori, operably linked to a first promoter that is repressed by a chromosome-encoded repressor, wherein the second ori preferably confers vector replication using DNA polymerase I; and (c) a foreign gene, operably linked to a second promoter that is preferably also repressed by a chromosome-encoded repressor. As a vaccine, the RADS is capable of causing an effective exposure of the immunized vertebrate's lymphoid tissues to a large dose of vector-encoded foreign gene product production in response to the withdrawal of the stimulus. Another advantage provided as a vaccine is the ability of the RADS microorganism to be grown in vitro under low copy number control, then switched to runaway conditions after vertebrate inoculation to cause an increase in antigen production in vivo. Under derepressed runaway conditions, the RADS microorganism is highly impaired due to extremely high plasmid replication activity coupled with extremely high foreign gene product production. Because of its impaired state, the derepressed RADS microorganism cannot generally survive for extended periods. The RADS therefore features an inherent containment system, in which the RADS microorganism cannot survive when not exposed to the repressor gene-activating stimulus, even in the absence of derepressible plasmid-derived phage lysis genes in the environmentally limited viability system (ELVS) as disclosed in WO96/40917.

The switch to the derepressed runaway state can be delayed after exposure of the microorganism to the derepressing environmental stimulus. In this "delayed RADS," the repressible promoters on the RAV continue their repression of the runaway condition and antigen production for a time even when the repressing stimulus is discontinued. An example of an activatible promoter that can be operably linked to a repressor on the RADS chromosome, and that is useful in delayed RADS, is the araC-$P_{BAD}$ promoter, which responds to arabinose. When linked in a RADS to a repressor such that the presence of arabinose represses the runaway condition, the transfer of the RADS bacteria to an environment without arabinose (such as when inoculated in a vertebrate) does not derepress the high copy number ori until arabinose that is still present inside the bacteria diffuses out or becomes metabolized by the microorganism. The delay can be advantageously increased by conferring mutations in the microorganism that eliminate its ability to metabolize the activating stimulus. This can be accomplished in the exemplified case with a mutation in the araCBAD operon to eliminate the ability of the microorganism to metabolize arabinose. The increased delay in this enhanced delay system is because the derepression to the runaway state is no longer influenced by the metabolism of the activator since the ability to metabolize the activator is eliminated. Thus, derepression is dependent only on diffusion of the activator (arabinose) out of the microorganism. Other means to alter and/or delay runaway replication and/or foreign gene expression are also disclosed.

The delay RADS is particularly useful for live bacterial vaccines because it allows time for the bacteria to colonize the vertebrate's lymphoid tissues before switching to high copy number and producing high levels of antigen. As such, the delayed RADS is very effective in vaccines administered intranasally. When the delay is enhanced by mutations preventing metabolism of the repressor as described above, the delay is sufficient for an oral vaccine to be ingested and colonize the gut-associated lymphoid tissue (GALT) before the derepressed runaway state allows production of high amounts of antigen. Thus, high antigen levels are delivered directly to the GALT, causing a highly effective immune response.

The RADS of the present invention can be utilized in conjunction with known mutations used to attenuate the virulence of the preferred pathogenic live vaccines. The RADS is also fully compatible with plasmid maintenance systems such as the balanced lethal systems as disclosed in U.S. Pat. No. 5,672,345.

Thus, in one embodiment, the present invention is directed to a microorganism comprising a regulated antigen delivery system (RADS). The RADS comprises (a) a vector comprising (1) a site for insertion of a gene encoding a desired gene product; (2) a first origin of replication (ori) conferring vector replication using DNA polymerase III; and (3) a second ori conferring vector replication using DNA polymerase I. Further, the second ori is operably linked to a first control sequence repressible by a first repressor, and the runaway vector does not comprise a phage lysis gene. The RADS also comprises a gene encoding a first repressor operably linked to a first activatible control sequence. Preferably, the vector also comprises a gene encoding a desired gene product inserted into the site of step (a), wherein the gene encoding the desired gene product is operably linked to a second control sequence. The first control sequence and the second control sequence can be the same sequence or different sequences. Preferred repressors are LacI repressor and C2 repressor; the second control sequence can be repressible by a second repressor.

Preferably, the microorganisms described above is an attenuated derivative of a pathogenic bacterium. Also, the vector is preferably a plasmid and the desired gene product is an antigen. Most preferably, the microorganism is a *Salmonella* sp. A preferred activatible control sequence is araCP$_{BAD}$.

The above-described microorganisms can include a balanced-lethal host-vector system consisting of a lack of a functioning essential gene on the chromosome and a recombinant functioning copy of the essential gene on the vector. The essential gene is preferably an asd gene. In one embodiment, the asd gene is inactivated by the insertion of a repressor gene operably linked to araCP$_{BAD}$. The microorganisms can also comprise an inactivating mutation in a native gene that is selected from the group consisting of cya, crp, phoPQ, ompR, galE, cdt, hemA, aroA, aroC, aroD and htrA.

In the above described microorganisms, the first ori is preferably a pSC ori, and the second ori is preferably a pUC ori; the first control sequence is preferably P22 P$_R$ and the first repressor is preferably C2 repressor. Additionally, the second control sequence is preferably P$_{trc}$ and the second control sequence preferably repressible by a second repressor, which is preferably a LacI repressor. An example of a preferred runaway vector of the present invention is pMEG-771 with a gene encoding an antigen. Modifications of that runaway vector, and other exemplified vectors, is also within the scope of the invention. Examples of antigens for use in the present invention are Ery65 and SeM.

In an additional embodiment, the desired gene in the microorganism is operably linked to a eukaryotic control sequence. In these embodiments, the microorganism also preferably comprises a ΔendA mutation.

The microorganism of the present invention can also exhibit delayed-RADS characteristics. The delayed RADS characteristics are preferably conferred by an alteration selected from the group consisting of (a) a mutation that delays the loss of activator molecules by metabolism or leakage, (b) a mutation or insertion to increase repressor concentration, and (c) inclusion of a vector control sequence with binding sites for more than one repressor and/or vector sequences encoding repressor molecules that act on a vector control sequence.

The present invention is also directed to a method of producing a desired gene product. The method comprises, in order, (a) engineering a gene encoding the desired gene product into the vector of any of the above described microorganisms, wherein the microorganism comprises control sequences that represses expression of the second ori under a first environmental condition, but in which the expression of the second ori is derepressed under a second environmental condition; (b) culturing the above described microorganism under the first environmental condition; and (c) culturing the microorganism under the second environmental condition for a time sufficient to produce the desired gene product. A preferred first environmental condition comprises the presence of arabinose and a preferred second environmental condition comprises the absence of arabinose. The first environmental condition can be achieved under in vitro culture conditions and the second environmental condition can be achieved in a vertebrate. The microorganism used in this method can also comprise an inactivating deletion in the araCBAD operon and/or in the araE gene.

The present invention is also directed to a vaccine for immunization of a vertebrate, wherein the vaccine comprises any of the microorganisms described above, in a pharmaceutically acceptable carrier.

In an additional embodiment, the present invention is also directed to a method of inducing immunoprotection in a vertebrate. The method comprises administering the above vaccine to the vertebrate.

The present invention is also directed to a method of delivering a desired gene product to a vertebrate. The method comprises administering any of the above microorganisms to the vertebrate.

Among the several advantages achieved by the present invention, therefore, may be noted the provision of vectors and microorganisms for production of a desired gene product, as in a live bacterial vaccine, in which a runaway condition is effected by environmental conditions that derepress constitutive vector replication and gene product production; the provision of vaccines comprising the above microorganisms for superior stimulation of immunoprotection to the antigen gene product; the provision of methods for inducing immunoprotection to a antigen gene product by using the above vaccines; and the provision of methods for delivering a desired gene product to a vertebrate.

BRIEF DESCRIPTION OF FIGURES AND FIGURE LEGENDS

Figure 19:
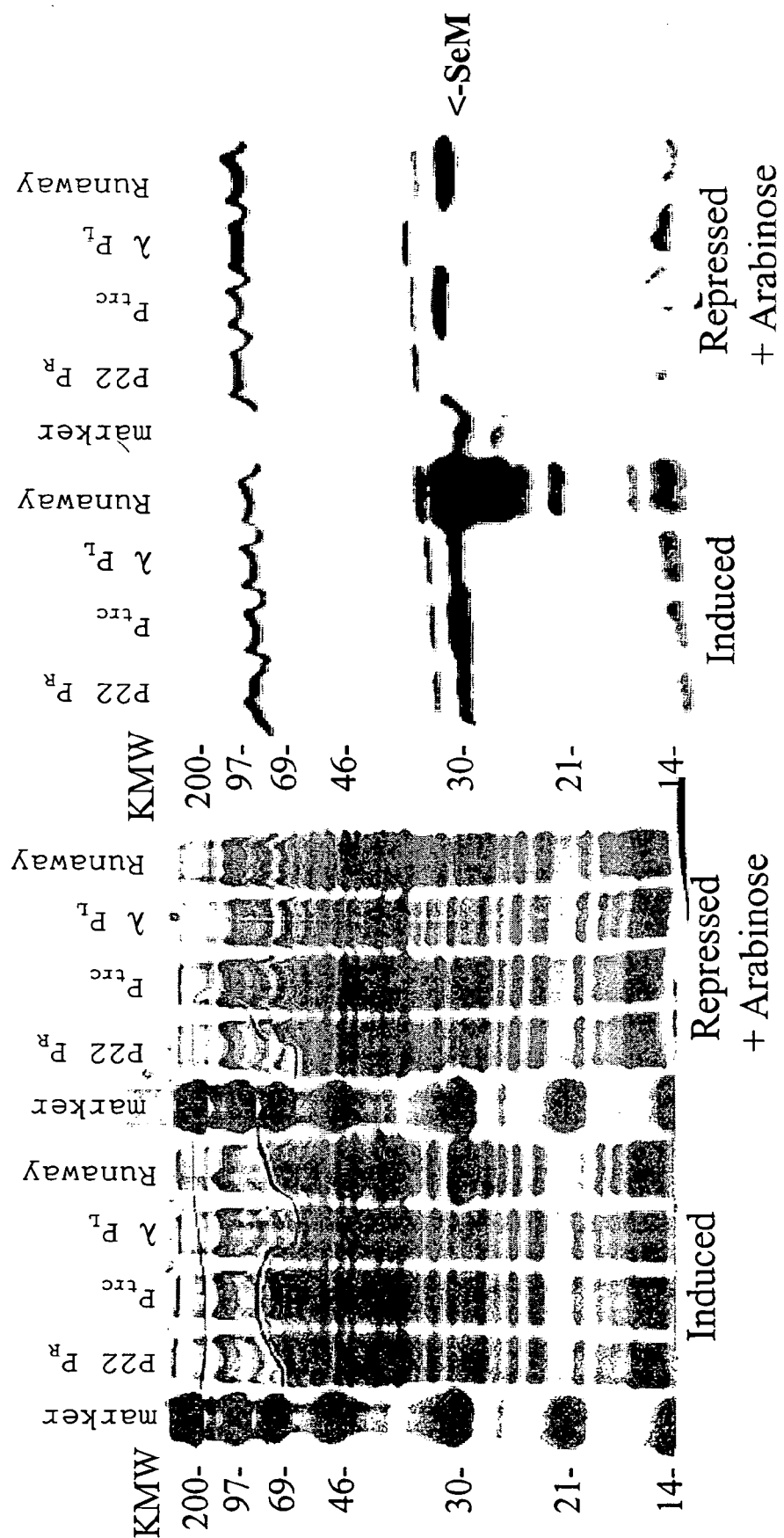

FIG. 19 is a comparison of SeM expression by S. typhimurium strains MGN-4598 (pMEG-825) $P22P_R$SeM, MGN-4598(pMEG-826) $P22P_{trc}$SeM, MGN-2238(pMEG-575) $\lambda P_L$SeM containing different Asd+ vectors with antigen expression under control of various promoters in comparison to the expression by a RADS, MGN-4598(pMEG-573)+ SeM, as revealed by Coomassie staining or Western blot of PAGE of total proteins of the strains when grown for six hours in Lennox Broth in the presence or absence of arabinose following a dilution of 1 to 1,000.

Figure 20:
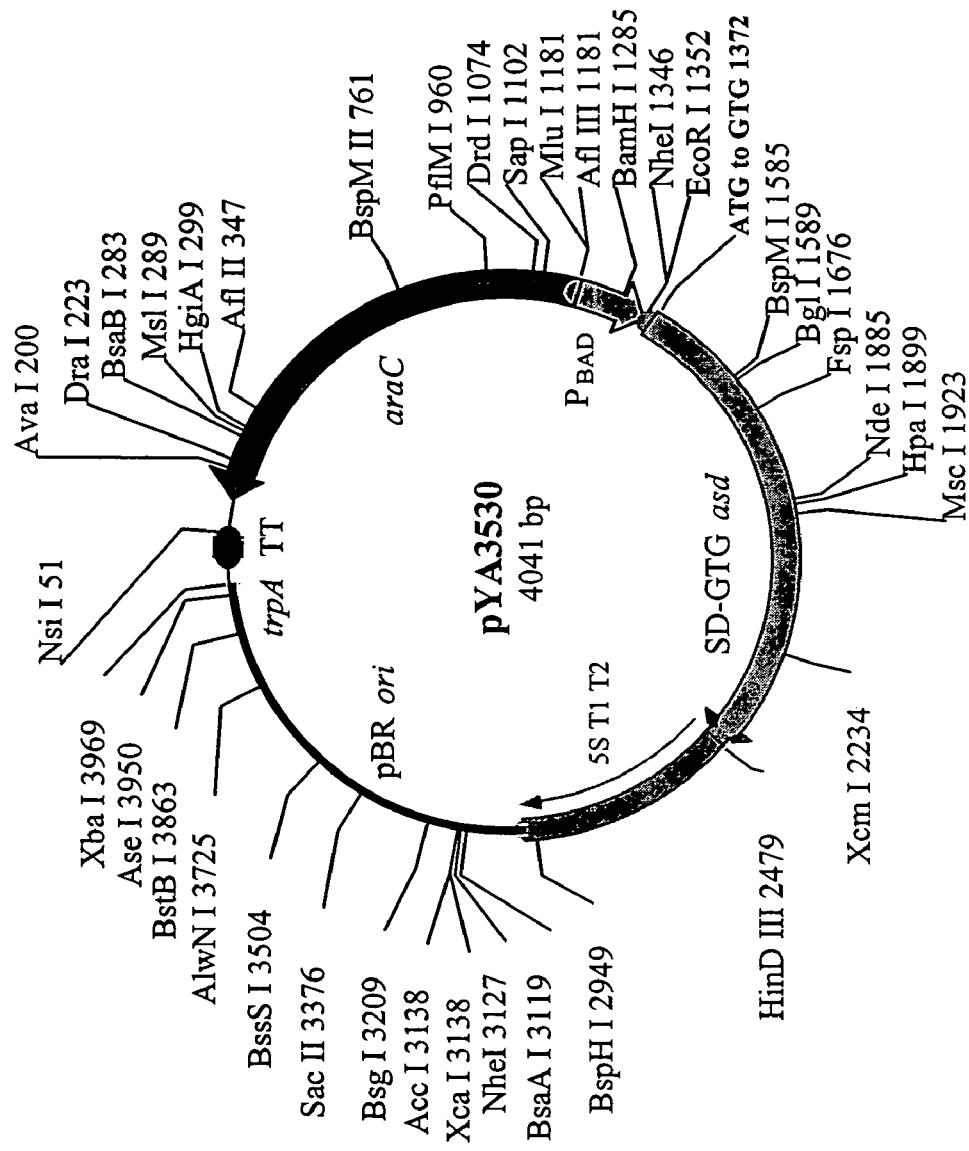

FIG. 20 depicts Asd+ vector pYA3530 with $araCP_{BAD}$GT-Gasd.

Figure 21:
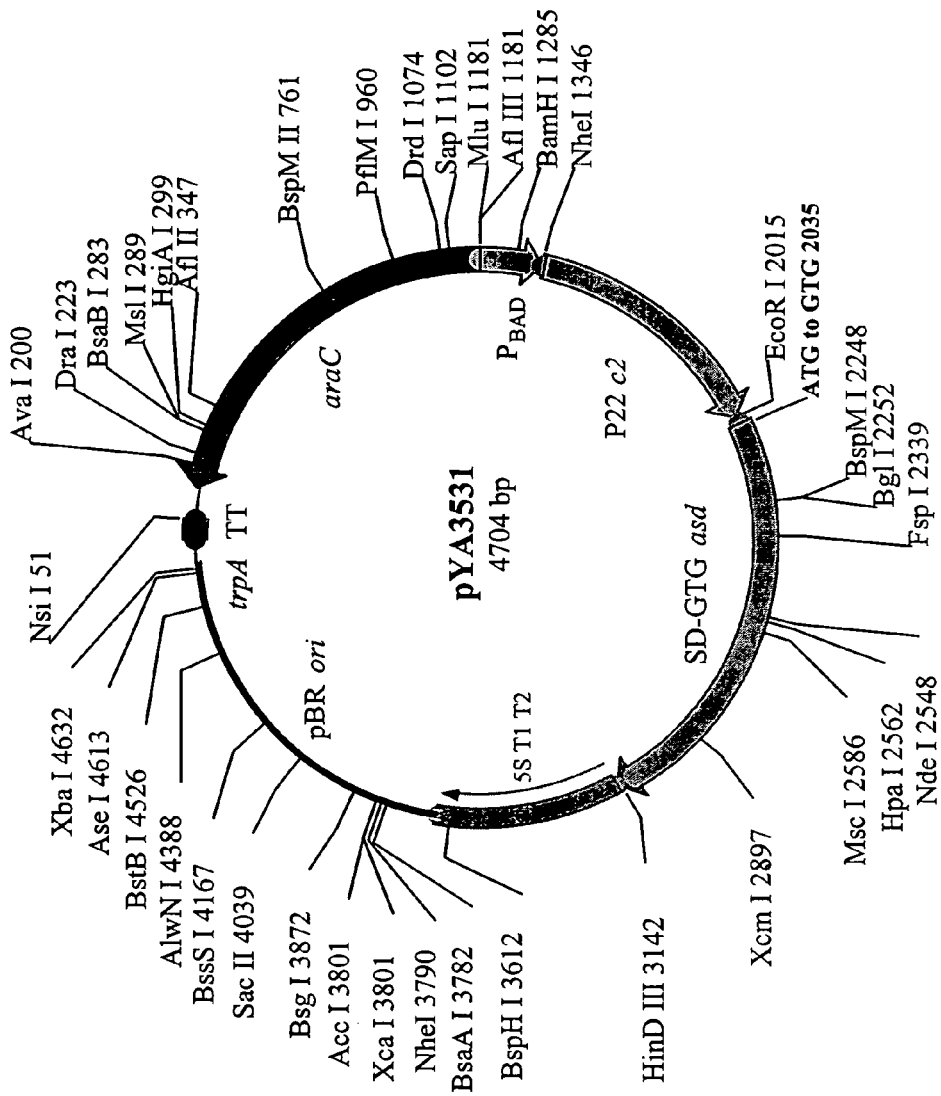

FIG. 21 depicts Asd+ vector pYA3531 with $araCP_{BAD}$c2GTGasd.

Figure 22:
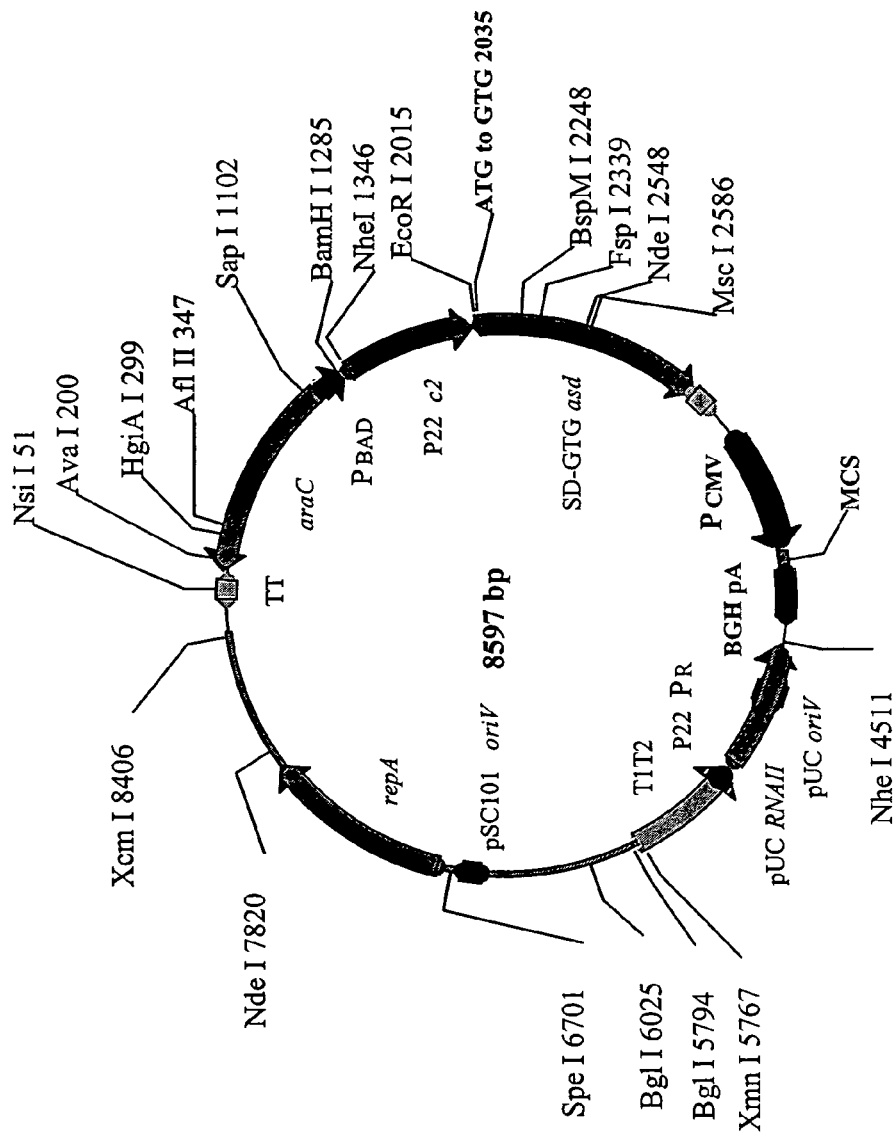

FIG. 22 depicts DNA transfer vector based on RAVs.

Figure 23:
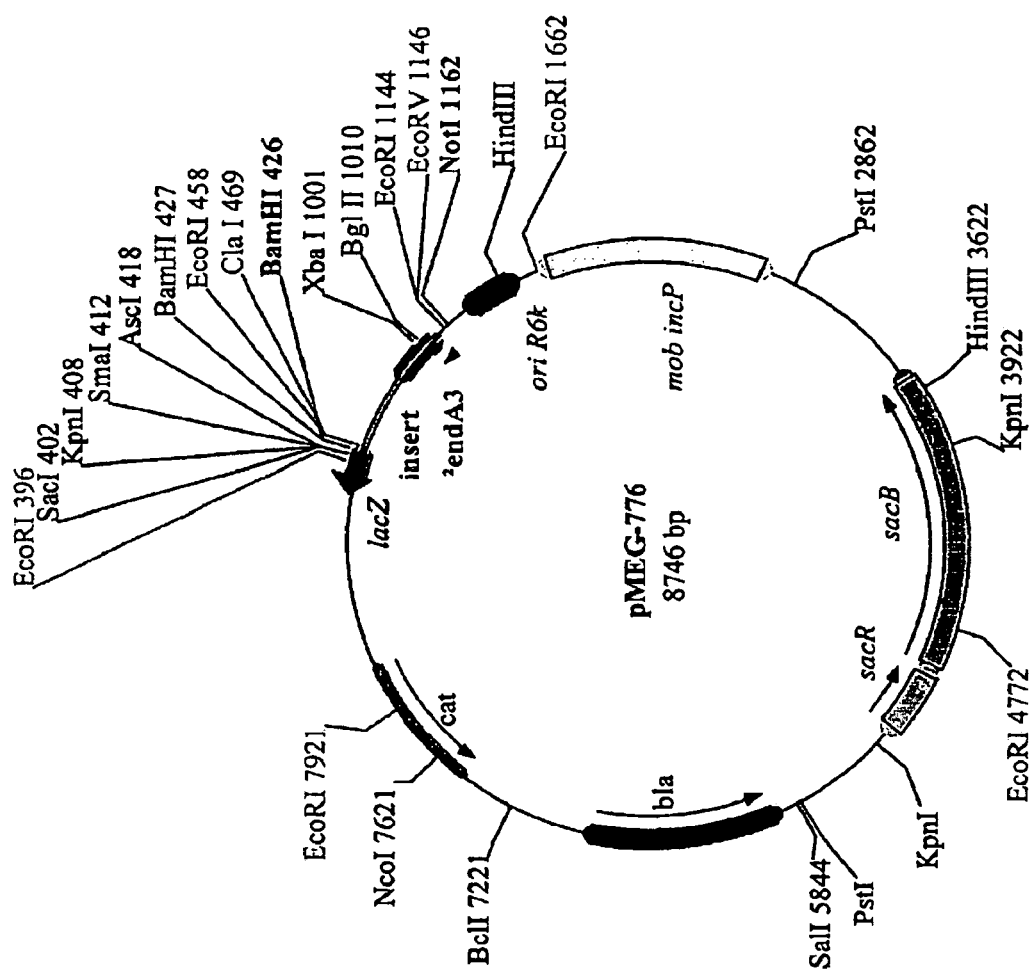

FIG. 23 depicts suicide vector pMEG-776, for delivery of $\Delta endA3$.

DETAILED DESCRIPTION OF THE INVENTION

A. Definitions

"Recombinant host cells", "host cells", "cells" and other such terms denoting microorganisms are used interchangeably, and refer to cells which can be, or have been, used as recipients for recombinant vectors or other transferred DNA, and include the progeny of the original cell transfected. It is understood that the progeny of a single parental cell may not necessarily be completely identical in genomic or total DNA complement as the original parent, due to accidental or deliberate mutation.

A "progeny population" means the population of living bacterial cells in a culture propagated from a single, recombinant bacterial cell. Unless otherwise defined, a recombinant gene on an extrachromosomal vector is "stably maintained" in a progeny population when the majority of the cells in a population which lack a native essential gene which is complemented by the recombinant gene are both able to survive in a particular environment (e.g., lacking diaminopimelic acid (DAP)) and continue to maintain and/or express a desired gene on the extrachromosomal vector. Preferably, at least 90% of the cells in the population survive in a stably maintained environment; more preferably, at least 99% of the cells survive.

"Control sequence" refers to DNA sequences that are necessary to effect the expression of coding sequences to which they are operably linked. As such, control sequences provide sites for the action of repressors, activators, enhancers, RNA polymerase, and other transcription factors. Non-limiting examples of such control sequences are promoters and ribosome binding sites.

Control sequences permitting expression of gene products in bacteria are distinctly different from control sequences necessary for gene expression in eukaryotic organisms such that prokaryotic control sequences generally do not function in eukaryotic cells and vice versa. The term "control sequence" can encompass those sequences from prokaryotes or eukaryotes.

A "regulator gene" is a gene that encodes a protein that controls the rate of synthesis of another gene. An example of a regulator gene is a gene that encodes a repressor.

As used herein, a "repressor" is a protein that is synthesized by a regulator gene and binds to an operator locus, blocking transcription of that operon.

As used herein, an "inducer" is a small organic molecule that causes an activatible control sequence to become active.

"Operably linked" refers to a juxtaposition wherein the components so described are in a relationship permitting them to function in their intended manner. A control sequence "operably linked" to a coding sequence is present in the cell in such a way that expression of the coding sequence may be influenced by the presence of the control sequence.

"Gram-negative bacteria" include cocci, nonenteric rods, enteric rods and spirilla. Non-limiting examples of genera of gram-negative bacteria include *Neisseria, Spirillum, Pasteurella, Brucella, Yersinia, Francisella, Enterobacter, Haemophilus, Bordetella, Escherichia, Salmonella, Shigella, Klebsiella, Proteus, Vibrio, Pseudomonas, Xanthomonas, Erwinia, Bacteroides, Acetobacter, Aerobacter, Agrobacterium, Azotobacter, Spirilla, Serratia, Vibrio, Myxococcus Rhizobium, Chlamydia, Rickettsia, Fusobacterium, Borrelia* and *Trepanema*.

"Gram-positive bacteria" include cocci, nonsporulating rods, and sporulating rods. Non-limiting examples of genera of gram-positive bacteria include *Actinomyces, Bacillus, Clostridium, Corynebacterium, Erysipelothrix, Lactobacillus, Listeria, Mycobacterium, Nocardia, Staphylococcus, Streptococcus*, and *Streptomyces*.

"Mycobacteria" are defined on the basis of their distinctive staining property, i.e., they resist decolorization with acidified organic solvents, and on the presence of long chain (approximately 60 carbons) mycolic acids.

A "mutation" is an alteration of a polynucleotide sequence, characterized either by an alteration in one or more nucleotide bases, or by an insertion of one or more nucleotides into the sequence, or by a deletion of one or more nucleotides from the sequence, or a combination of these.

A "gene" is a biological unit of heredity. Generally, a gene is a polynucleotide sequence that encodes an RNA molecule or a polypeptide, or a mutation of said polynucleotide sequence. The gene may be a naturally occurring sequence that is capable of being expressed into an active or inactive polypeptide. The gene may also comprise a mutation, for example a point mutation, insertion, or deletion, such that it is not capable of being expressed, or such that it expresses an altered or truncated polypeptide or RNA molecule. A gene may be created by recombinant DNA methodologies. Alternatively, the gene may be synthesized by well-known synthetic methods.

Most (91%) structural genes use the ATG codon for methionine as the first codon. However, more rarely (8%) they employ GTG as the start codon and even more rarely (1%) use the TTG start codon, but never CTG. When transcribing messenger RNA, transcription starts at the +1 nucleotide site and ends after the transcription terminator.

A "native gene" is a gene as it occurs in the chromosome of a wild-type organism, for example, the gene encoding β-aspartic semialdehyde dehydrogenase (Asd) in wild-type *E. coli* or *Salmonella*.

A "recombinant gene," as used herein, is defined as an identifiable polynucleotide sequence within a larger polynucleotide sequence that is not found in nature in that form and position in the larger sequence. The recombinant gene can be, for example, a wild-type gene that is inserted in a non-native position in the chromosome, or a mutant form of the wild-type gene in the native position, or a wild-type gene inserted into its native position along with other non-native sequences, as can occur at low frequency in homologous recombination between a plasmid and a chromosome. A recombinant gene can also include combinations of coding regions with control regions with which the coding regions do not naturally occur. As used herein, recombinant genes are the products of particular genetic engineering manipulations.

The gene symbols for mutant strains utilized herein are those described by Berlyn, Chapter 109 in Neidhardt et al., 1996, and Sanderson et al., Chapter 110 in Neidhardt et al., 1996. The symbols used for transposons, particularly Tn10, follow the convention used in Altman et al., Chapter 141 in Neidhardt et al., 1996.

A "replicon" is an autonomously replicating DNA. The characteristic of autonomous replication is conferred by an origin of replication. Examples include plasmid vectors, and bacterial chromosomes.

A "runaway vector" ("RAV") is a extrachromosomal replicating nucleic acid such as a plasmid which comprises two origins of replication. One of the origins of replication confers a low copy number and preferably confers vector replication using DNA polymerase III; the second origin of replication preferably confers vector replication using DNA polymerase I. that can replicate in a microorganism at either a low copy number or a high copy number, depending on the status of control sequences controlling copy number.

An "individual" treated with a vaccine of the invention is defined herein as including all vertebrates, for example, mammals, including domestic animals and humans, various species of birds, including domestic birds, particularly those of agricultural importance. In addition, mollusks and certain other invertebrates have a primitive immune system, and are included as an "individual".

"Transformation" or "transfection," as used herein, refers to the insertion of an exogenous polynucleotide into a host cell, irrespective of the method used for the insertion, for example, direct uptake (naturally or by electroporation), transduction, or conjugation. The exogenous polynucleotide may be maintained as a plasmid, or alternatively, may be integrated within the host genome.

By "vaccine" is meant an agent designed to stimulate the immune system of a living organism so that protection against future harm is provided. A particular vaccine may or may not be effective in any particular animal. Immunization refers to the process of rendering an organism immune to a disease.

As used herein, "immune system" refers to anatomical features and mechanisms by which a multi-cellular animal reacts to an antigen. As is well known, the vertebrate humoral immune system results in the elicitation of antibodies that specifically bind to the antigen. The antibody so produced may belong to any of the immunological classes, such as immunoglobulins A, D, E, G or M. Of particular interest are vaccines that stimulate production of immunoglobulin A (IgA) since this is the principal immunoglobulin produced by the secretory system of warm-blooded animals. However, vaccines of the present invention are not limited to those that stimulate IgA production. For example, vaccines of the nature described infra are likely to produce a range of other immune responses in addition to IgA formation, for example, cellular immunity. Immune response to antigens is well studied and widely reported. A survey of immunology is given in Roitt, Brostoff and Male, *Immunology:* Fourth Edition, C. V. Mosby International Ltd., London (1998). Unless otherwise indicated, vaccines are live bacteria that express or deliver antigens or genetic material encoding antigens to which immune responses are desired.

As used herein, "immunogenic" means able to elicit an immune response.

A vertebrate is any member of the subphylum Vertebrata, a primary division of the phylum Chordata that includes the fishes, amphibians, reptiles, birds, and mammals, all of which are characterized by a segmented bony or cartilaginous spinal column. All vertebrate species have a functional immune system and respond to antigens by cellular and/or humoral immune responses. Thus all vertebrates are capable of responding to vaccines. Although vaccines are most commonly given to mammals, such as humans or dogs (rabies vaccine), vaccines for commercially raised vertebrates of other classes, such as the fishes and birds, are contemplated as being within the scope of the present invention.

As used herein, a "pathogen" is a microorganism that is capable of causing disease or impairing normal physiological function, or is an attenuated derivative of a disease causing microorganism.

"Attenuated" refers to a pathogen having mutations that reduce the ability of the pathogen to elicit disease symptomology and disease in an individual, but which do not eliminate the potential of the attenuated bacterium to attach to, invade and persist in appropriate lymphoid tissues within the individual. Attenuated microbes are useful, for example, to expose an organism to a particular gene product, such as an antigen or a therapeutic protein, over an extended time period. "Attenuated" does not mean that a microbe of that genus or species cannot ever function as a pathogen, but that the particular microbe being used is attenuated with respect to the particular animal being tested. Attenuated host cells of the present invention may belong to a genus or species that is normally pathogenic. Attenuated strains are incapable of inducing a full suite of symptoms of the disease that is normally associated with its pathogenic counterpart. Sometimes "avirulent" is used as a substitute term for attenuated.

Lymphoid tissues of interest in the present invention include the gut-associated lymphoid tissue (GALT), bronchial-associated lymphoid tissue (BALT), basal-associated lymphoid tissue (NALT), mucosal-associated lymphoid tissue (MALT), and the conjunctive-associated lymphoid tissue.

As used herein, "microbe" or "microorganism" includes bacteria, viruses, protozoa, and unicellular fungi.

As used herein, "DNA vaccine vector" refers to a plasmid DNA molecule propagated in a bacterial cell that has a gene sequence encoding a desired gene product operably linked to a eukaryotic control sequence, so that the desired gene product is expressed only after introduction of the DNA vaccine vector internally into eukaryotic cells by vaccination (immunization). The DNA vaccine vector can be administered to individuals to be immunized by injection, air gun or preferably by use of attenuated bacteria that liberate the DNA vaccine vector on entrance into host cells of the immunized individual. See, e.g., Herrmann et al., 1999, "DNA Vaccines for Mucosal Immunity," pp. 809-816 in MUCOSAL IMMUNITY, Second ed., Ogra, Mestecky, Lamm, Strober, Bienenstock, and McGhee, eds., Academic Press, San Diego, 1628 pp.; Ulmer et al. (1996).

B. General Description

Unless otherwise indicated, the practice of the present invention employs conventional techniques of cell culture, molecular biology, microbiology, recombinant DNA manipulation, immunology and animal science, which are within the skill of the art. Such techniques are explained fully in the literature. See, e.g., DNA CLONING, Volumes I and II (D. N. Glover, ed., 1985); OLIGONUCLEOTIDE SYNTHESIS (M. J. Gait ed., 1984); NUCLEIC ACID HYBRIDIZATION (B. D. Hames and S. J. Higgins, eds., 1984); B. Perbal, A PRACTICAL GUIDE TO MOLECULAR CLONING (1984); the series, METHODS IN ENZYMOLOGY (Academic Press, Inc.); VECTORS: A SURVEY OF MOLECULAR CLONING VECTORS AND THEIR USES (R. L. Rodriguez and D. T. Denhardt, eds., 1987, Butterworths); Sambrook et al. (1989), MOLECULAR CLONING, A LABORATORY MANUAL, second ed., Cold Spring Harbor Laboratory Press; Sambrook et al. (1989), MOLECULAR CLONING, A LABORATORY MANUAL, second ed., Cold Spring Harbor Laboratory Press; and Ausubel et al. (1995), SHORT PROTOCOLS IN MOLECULAR BIOLOGY, John Wiley and Sons.

The present invention is based on the discovery that the production of a vector-borne recombinant desired gene product in a microorganism can be conveniently increased by utilizing vector control elements that can be induced to increase the copy number of the vector.

The invention is directed toward a Regulated Antigen Delivery System (RADS), which utilizes microorganisms that comprise extrachromosomal vectors, called runaway vectors (RAVs), as well as genes encoding at least one repressor whose synthesis is under the control of an activatible control sequence. Essential elements of a RAV are (a) a gene encoding a desired gene product operably linked to a control sequence, (b) a first origin of replication ("ori") conferring vector replication using DNA polymerase I, (c) a second ori conferring vector replication using DNA polymerase III. The second ori is operably linked to a first control sequence that is repressible by the repressor.

In a RADS, the microorganism is maintained under conditions in which the first control sequence is repressed. Since the first control sequence controls utilization of the second ori, replication under these maintenance conditions is controlled by the first ori. However, under conditions where the repressor affecting the second ori is not made, derepression of the second ori takes place and control of vector replication switches to the second ori. The second ori then confers uncontrolled vector replication, thus producing very large amounts of the vector and the desired gene product encoded on the vector.

As further discussed infra, preferred use of RADS microorganisms is as a live bacterial vaccine. In those embodiments, the desired gene product is an antigen.

In a RADS, levels of expression of the desired gene product is controlled, at least in part, by controlling vector copy number. Copy number is controlled through the use of more than one origin of replication (ori) on the RAV.

As is well known, an ori is the region on a chromosome of extrachromosomal vector where DNA replication is initiated. For a review of plasmid replication in bacteria, see Helinski et al., pp. 2295-2324 in *Escherichia coli* and *Salmonella*, Cellular and Molecular Biology, Second Ed. Neidhardt et al., Eds. 1996. In the ColE1-type plasmids, replication is initiated by the synthesis of a 700-base preprimer RNA, designated RNA II. Transcription of RNA II is initiated 555 bases upstream from the ori. Upon transcription, the 3' end of RNA II forms a hybrid with the plasmid at the ori. Cleavage of this RNA-DNA hybrid occurs at the replication origin, exposing a 3'-hydroxyl group that serves as the primer for DNA synthesis catalyzed by host DNA polymerase I. ColE1-type replicons do not specify an essential replication protein, however, they do require DNA polymerase I. Replication control in the ColE1-type plasmids is normally regulated by the binding of an unstable RNAI transcript, which is complementary to the RNAII pre-primer transcript. RNAI is transcribed divergent to, but within the RNAII coding region. Additional levels of regulation are provided by a protein encoded by rop elsewhere on the plasmid, which interacts with the RNAI and RNAII transcripts to prevent DNA replication. The RAV as described has been obtained by replacing the native promoter for RNAII with a-strong regulated promoter, capable of producing excess RNAII transcripts and thus uncontrolled replication of the ColE1-type replicon when the repressor for the new promoter is not present.

The choice of ori's for use in the present invention is not narrowly limited, provided the first ori confers replication by DNA polymerase III (e.g., the product of the dnaE gene in E. coli) and the second ori confers replication by DNA polymerase I (e.g., the product of the polA gene in E. coli). Preferably, the first ori confers a low copy number to the vector, to minimize any disadvantage imparted by replication of the vector. A preferred first ori is a pSC ori, which is known to confer about six to eight vector copies per chromosomal DNA equivalent in E. coli or Salmonella spp. A preferred second ori is a pUC ori.

The second ori is operably linked to a promoter that is repressible by a repressor. Preferred promoters for this purpose are $P_{lac}$ or $P_{trc}$, which are repressed by the LacI repressor, and P22 $P_R$, which is repressed by the C22 repressor.

The LacI repressor and C22 repressor are preferred repressors. Preferably, these repressors are encoded on the chromosome of the microorganism. The repressor gene is operably linked to an activatible control sequence that allows synthesis of the repressor only when the inducer of the control sequence is present. As more fully discussed infra, a preferred activatible control sequence is araCP$_{BAD}$, which is activated by arabinose. Therefore, in a RADS microorganism using araCP$_{BAD}$ to control repressor synthesis, the presence of arabinose activates expression of the repressor, which prevents the utilization of the second ori. Vector replication is then is under the control of the first ori. However, when arabinose is withdrawn, the repressor is no longer made and the first control sequence is derepressed, allowing runaway replication of the vector. Regulation with arabinose is also useful since free arabinose is not generally available in nature. For example, arabinose is absent from avian and vertebrate tissues.

Regulation with arabinose is especially useful for delayed RADS. As discussed more fully infra, in delayed RADS, the induction of the high copy number ori is delayed after being triggered. Such a system is useful for live bacterial vaccines, which are generally grown in culture under conditions in which the runaway plasmid replication is not initiated (e.g., with arabinose). The bacteria are then inoculated into the vertebrate. In such a system, the inoculated bacteria colonize the lymphoid tissue before runaway plasmid replication is initiated, which allows production of large amounts of antigen. The delay in initiating runaway vector replication by the high copy number ori avoids the interference of the bacteria's ability to colonize caused by the production of high antigen levels and high vector levels. A delay system where araC-P$_{BAD}$ controls synthesis of the repressor, to allow the second ori to initiate runaway replication when arabinose is not-present; is effective because, once arabinose is no longer supplied, it takes time for the arabinose concentration to decline sufficiently to allow the AraC protein to begin acting as a repressor. However, this delay is not very long because the araCBAD operon efficiently metabolizes arabinose, thus rapidly (within about 15 min) reducing arabinose levels to the point where repressor synthesis does not occur. This short delay system can nonetheless allow sufficient delay of the initiation of runaway replication to provide an advantage, e.g., in live bacterial vaccines where the vaccine can be delivered to lymphoid tissue quickly, as is the case with intranasal inoculation. However, with oral inoculation, runaway replication would commence well before the vaccine reaches the GALT. In that situation, much of the antigen produced by the runaway vector is not exposed to lymphoid tissue and is thus wasted. Therefore, for situations where a longer delay is desired, as with oral administration of a live bacterial vaccine, an enhanced delay RADS can be utilized. In that system, the time of temporary viability is extended by utilizing a microorganism with an inactivation mutation in the operon that controls production of enzymes that degrade the inducer. Where arabinose is the inducer, its metabolism can be eliminated by an inactivating deletion mutation in the araCBAD operon. Such a deletion prevents metabolism of arabinose, leading to a higher intracellular level of arabinose after arabinose exposure has been withdrawn. This results in a longer delay before arabinose levels decline sufficiently to allow the AraC protein to begin acting as a repressor. This enhanced delay is sufficient to allow orally administered vaccines comprising the enhanced delayed RADS system to colonize the GALT before runaway vector replication is initiated.

An example of a RAV is the plasmid vector pMEG-771 (FIG. 1). pMEG-771 must be maintained in a bacterial strain which possesses genes for two repressor proteins, the P22 C2 repressor and the LacI repressor of the lac operon, whose syntheses are regulated by the araCP$_{BAD}$ control sequence so that transcription of the c2 and lacI genes are dependent upon the presence of arabinose in the growth medium. The araC gene product in the presence of arabinose is a transcription activator causing transcription from P$_{BAD}$ of any structural genes linked to it. In the absence of arabinose the araC gene product serves as a repressor at P$_{BAD}$ to preclude transcription of structural genes fused to the P$_{BAD}$ promoter. Within the chromosome of the strain harboring pMEG-771 are the deletion/insertion mutations ΔasdA19::TTaraCP$_{BAD}$c2TT and ΔilvG3::TTaraCP$_{BAD}$lacITT. When this strain is grown in the presence of arabinose, the c2 repressor gene is expressed and the C2 repressor binds to the P22 P$_R$ to preclude transcription of the pUC RNAII gene, which is fused to P$_R$. The RNAII gene specifies an initiator RNA that, in the presence of DNA polymerase I (encoded by the chromosomal polA gene), initiates replication at the pUC ori. The plasmid continues to replicate making use of the pSC101 replicon control so that there are about six plasmid copies per chromosome DNA equivalent. This strain also produces copious quantities of the LacI repressor protein when the strain is grown in the presence of arabinose. In that situation, the lacI gene product binds to P$_{TRC}$ and represses transcription from this promoter so that any foreign gene sequence inserted into the multi cloning site from NcoI to HindIII is not synthesized. In this case, the strain grows exceedingly well under cultural conditions such as in a fermenter since energy demands to maintain the pMEG-771 plasmid vector are minimal due both to low plasmid copy number and the inability to express large amounts of the foreign protein. However, when the vaccine strain is administered to an immunized animal host, there is no exogenous arabinose and the arabinose within the bacterial vaccine cells disappears due to its catabolism or also by possible leakage out of the cell. Under those conditions, C2 and LacI repressor proteins cease to be synthesized and the density of these repressors within the cell decreases permitting not only transcription of the pUC RNA II sequence needed to initiate plasmid replication from the pUC ori in a completely unregulated manner, but also initiation of transcription of a gene for a foreign antigen. The overall level of production of the desired gene product is thus greatly increased due to increasing plasmid copy number along with increased transcription of the foreign gene from P$_{TRC}$.

Some elements of RADS were previously described in WO96/40947. See in particular FIG. 8 of that publication.

However, in that system the RAV was used primarily for the purpose of preventing the bacterial vaccine from retaining viability in nonpermissive environments such as below 30°, since in moving from body temperature to ambient temperature the cI857 vector-borne gene product becomes functional so that c2 repressor gene expression ceases, which leads to the derepression of the lysis genes.

The RAV exemplified in pMEG-771 utilizes various regulatory elements that work alone or in conjunction with other regulatory elements to achieve the desired result. The regulatory elements used in a RADS are not narrowly limited to those used in pMEG-771 and its associated host (araCP$_{BAD}$, P$_R$, P$_{TRC}$, lacI repressor, C2 repressor); these elements may be substituted for others with similar functions, described as follows and as known in the art.

In general, the genes in a RADS of the present invention can be regulated 1) by linking the coding sequences to control sequences that promote or prevent transcription under permissive and non-permissive conditions, 2) by regulating the expression of trans regulatory elements that in turn promote or prevent transcription of the genes of the RAV and/or the host chromosome, 3) by adapting or altering trans regulatory elements, which act on the genes of the RAV and/or host chromosome, to be active or inactive under either high copy number or low copy number conditions, or by using combinations of these schemes. The RAVs of the present invention require various promoters to coordinate expression of different elements of the system. Some elements, such as temperature-sensitive repressors or environment-specific regulatory elements, use inducible, derepressible or activatible promoters. Preferred promoters for use as regulatory elements in an RAV are the cspA gene promoter, the phoA gene promoter, P$_{BAD}$ (in an araC-P$_{BAD}$ system), the trp promoter, the tac promoter, the trc promoter, λP$_L$, P22 P$_R$, mal promoters, and the lac promoter. These promoters mediate transcription at low temperature, at low phosphate levels, in the presence of arabinose, in the presence of low tryptophan levels, and in the presence of lactose (or other lac inducers), respectively. Each of these promoters and their regulatory systems are well known.

Trans Regulatory Elements. As used herein, "trans regulatory element" refers to a molecule or complex that modulates the expression of a gene. Examples include repressors that bind to operators in a control sequence, activators that cause transcription initiation, and antisense RNA that binds to and prevents translation of a mRNA. For use in RADS of the present invention, expression from regulated promoters is modulated by promoter regulatory proteins. These promoter regulatory proteins can function to activate or repress transcription from the promoter. Preferred trans regulatory elements are proteins mediating regulation of the cspA gene promoter, the phoA gene promoter, P$_{BAD}$ (in an araC-P$_{BAD}$ system), the trp promoter, the tac promoter, the trc promoter, the mal promoters, and the lac promoter.

Another type of trans regulatory element is RNA polymerase. Genes of the RADS can be regulated by linking them to promoters recognized only by specific RNA polymerases. By regulating the expression of the specific RNA polymerase, expression of the gene is also regulated. For example, T7 RNA polymerase requires a specific promoter sequence that is not recognized by bacterial RNA polymerases. A T7 RNA polymerase gene can be placed in the host cell and regulated to be expressed only in the permissive or non-permissive environment. Expression of the T7 RNA polymerase will in turn express any gene linked to a T7 RNA polymerase promoter. A description of how to use T7 RNA polymerase to regulate expression of a gene of interest, including descriptions of nucleic acid sequences useful for this regulation appears in Studier et al., *Methods Enzymol.* 185:60-89 (1990).

Another type of trans regulatory element is antisense RNA. Antisense RNA is complementary to a nucleic acid sequence, referred to as a target sequence, of a gene to be regulated. Hybridization between the antisense RNA and the target sequence prevents expression of the gene. Typically, antisense RNA complementary to the mRNA of a gene is used and the primary effect is to prevent translation of the mRNA. Expression of the genes of a RADS can be regulated by controlling the expression of the antisense RNA. Expression of the antisense RNA in turn prevents expression of the gene of interest. A complete description of how to use antisense RNA to regulate expression of a gene of interest appears in U.S. Pat. No. 5,190,931.

Other types of trans regulatory elements are elements of the quorum sensing apparatus. Quorum sensing is used by some cells to induce expression of genes when the cell population reaches a high density. The quorum sensing system is activated by a diffusible compound that interacts with a regulatory protein to induce expression of specific genes (Fuqua et al., *J. Bacteriol.* 176:269-275 (1994)). There is evidence that the diffusible compound, referred to as an autoinducer, interacts directly with a transcriptional activator. This interaction allows the activator to bind to DNA and activate transcription. Each quorum sensing transcriptional activator is typically activated only by a specific autoinducer, although the activator can induce more than one gene. It has also been shown that quorum sensing regulation requires only the transcriptional activator and a gene that contains a functional binding site for the activator (Gray et al., *J. Bacteriol.* 176:3076-3080 (1994)). This indicates that quorum sensing regulation can be adapted for the regulation of genes in a RADS of the present invention. For example, a gene encoding a quorum sensing transcriptional activator can be expressed in a RADS host, and another gene of the RADS can be under the control of a promoter that is controlled by the quorum sensing transcriptional activator. This will cause the RADS gene to be expressed when the cognate autoinducer is present and not expressed in the absence of the autoinducer. A gene under such control is referred to herein as being under quorum control. Where the RADS host produces the autoinducer, the gene under quorum control will be expressed when cell density is high, and will not be expressed when cell density is low. Any of the genes in a RADS can be placed under quorum control, including essential genes, lethal genes, replication genes and regulatory genes, which are described in WO96/40947. For operation of the RADS, the autoinducer can be supplied, for example, by the RADS host through the action of endogenous genes (that is, genes responsible for the synthesis of the autoinducer), in culture medium, or both. In the later case, the autoinducer supplied in the medium mimics the permissive conditions of high cell density. Alternatively, a gene for the production or synthesis of the autoinducer can be incorporated as an element of the RADS. Such an autoinducer gene would be considered a regulatory gene as used herein.

Examples of quorum sensing transcriptional activator genes and genes for the production of their cognate autoinducer are luxR and luxI (Gray et al., *J. Bacteriol.* 176:3076-3080 (1994)), lasR and lasI (Gambello and Iglewski, *J. Bacteriol.* 173:3000-3009 (1991)), traR and traI (Piper et al., *Nature* 362:448-450 (1993)), rhlI and rhlR (Latifi et al., *Mol Microbiol* 17(2):333-343 (1995)), and expR and expI (Pirhonen et al., *EMBO J* 12:2467-2476 (1993)). Autoinducers for these pairs include N-(3-oxohexanoyl)homoserine lactone (VAI; for LuxR), N-(3-oxododecanoyl) homoserine lactone (PAI; for LasR), and N-(3-oxooctanoyl) homoserine lactone (AAI; for TraR). Some promoters that are induced by the quorum sensing transcriptional activators are luxI promoters, the lasB promoter, the traA promoter, and the traI promoter.

Quorum control can be used to effect regulated antigen delivery in a number of ways, for example, by obtaining production of desired gene products such as antigens, and non-expression of high copy number ori primer RNA II sequences under permissive conditions of high cell density in, for example, a fermenter, with the opposite expression pattern appearing as cell density decreases when, for example, the cells are introduced into an animal or released into the environment. As another example, a regulatory gene such c2 can be placed under quorum control. Then other elements of the RADS can be placed under control of the product of the regulatory gene, using, for example, P22P$_R$. The regulatory gene will be expressed in the presence of the autoinducer, and not expressed in the absence of the autoinducer. Where the regulatory gene is c2 and a RADS gene is linked to P22P$_R$, the RADS gene will be expressed (that is, derepressed) when the autoinducer is not present (since no C2 protein will be made), and repressed when the autoinducer is present. Where an essential gene or a replication gene is under quorum control (the autoinducer induces expression), it is preferred that the autoinducer be present under permissive conditions and absent under non-permissive conditions. Where a regulatory gene is under quorum control, the presence or absence of the autoinducer under permissive or non-permissive conditions will depend on whether the product of the regulatory gene is a positive or negative regulator.

Trans regulatory elements, such as repressors or antisense RNA, can be expressed from either the chromosome or a plasmid. To limit the size and complexity of the plasmid portion of the system, however, it is preferred that these regulatory elements be expressed from the bacterial chromosome.

Temperature-Sensitive Regulation. A preferred type of regulation for microorganisms intended for growth in humans or other warm-blooded animals is temperature regulation. This is based on the contrast between the high and constant body temperature present in mammals and birds and the low and variable temperature present in the ambient environment into which microorganisms are shed. To accomplish this, a preferred RADS expresses genes ensuring survival at about 37° C. It is preferred that, where an RADS is intended to be administered to an animal, any temperature-based regulation should take into account the normal body temperature of the target animal. For example, chickens have a body temperature of 41.5° C., and pigs have a body temperature of around 40° C.

Temperature-regulated gene expression suitable for use in the RADS is described by Neidhardt et al., *Annu. Rev. Genet.* 18:295-329 (1984). There are well-defined heat shock genes that are strongly expressed at high temperature. Although the expression of these genes is temperature-regulated, there is frequently some low basal level of expression at the restrictive temperatures (Jones et al., *J. Bacteriol.* 169:2092-2095 (1987)). Temperature-regulated promoters exhibiting tighter control are described by Tobe et al., *Mol. Micro.* 5:887-893 (1991), Hromockyi et al., *Mol. Micro.* 6:2113-2124 (1991), and Qoronfleh et al., *J. Bacteriol.* 174:7902-7909 (1992).

For desired genes such as antigens, the *S. flexneri* virB promoter can be used, with *S. flexneri* virF gene and promoter elsewhere on the same plasmid, on a separate plasmid, or on the chromosome (Hromockyi et al. (1992); Tobe et al. (1991). A *Yersina* two component system for temperature regulation can also be used involving the structural gene for the temperature-regulated positive activator virF (Lambert de Rouvroit et al., *Molec. Microbiol.* 6:395-409 (1992) in combination with promoters of the yopH or yadR genes, with or without modification of the histone-like YmoA protein encoded by ymoA (Cornelis, in *Molecular Biology of Bacterial Infections* (Cambridge University Press, Cambridge, 1992)). The *Shigela* virF gene is equivalent to IcrF in *Y. pestis* (Hoe et al., *J. Bacteriol.* 174:4275-4286 (1992). Many other repressor-promoter combinations can be adapted to express genes in a temperature-specific manner by using temperature-sensitive forms of the repressor. Methods for obtaining temperature-sensitive mutant repressors are well established.

Cold-specific expression can also be accomplished by coupling a gene to a cold-shock promoter or a cold-sensitive promoter. Cold shock promoters may be obtained from known cold-shock genes. Cold shock genes with promoters have been described (Jones et al. (1987)). An example of a useful cold-shock promoter is the promoter from cspA (Vasina and Baneyx, *Appl. Environ. Micro.* 62:1444-1447 (1996)). Promoters with temperature-specific expression can be identified by a promoter probe vector. Such vectors have flanking DNA from a gene that is dispensable and which can readily be selected for or identified using, for example, a chromogenic substrate. Other cold-specific promoters useful for expression of the essential gene can be identified by screening for cold-sensitive lack of expression of β-galactosidase in an *S. typhimurium* lacZ fusion library (Tanabe et al., *J. Bacteriol.* 174:3867-3873 (1992)).

A preferred system that is less complex involves the interaction of the bacteriophage lambda promoters, $\lambda P_L$ and $\lambda P_R$, with the CI857 temperature-sensitive repressor. This system has been described, for example, by Lieb, *J. Mol. Biol.* 16:149-163 (1966). The lambda phage promoters $\lambda P_L$ and $\lambda P_R$, with their mutant temperature-sensitive repressor CI857, provide a tightly regulated system used in expression vectors to provide controlled expression of toxic genes (O'Connor and Timmis, *J. Bacteriol.* 169:4457-4462 (1987)) and could also be used to regulate the synthesis of the initiator RNA II to initiate RNA replication at the DNA polymerase I dependent ori of high copy number plasmid vectors. The cI857 gene product is synthesized but inactive at 37° C., and especially at even higher temperatures found in birds and some mammals, and is synthesized but actively represses expression of genes at 30° C. and below whose transcription is controlled by either $\lambda P_L$ or $\lambda P_R$.

Leaky expression from the control sequences of a RADS, if encountered, can be eliminated in several ways. For example, the level of CI repressor produced can be increased by placing the cI857 gene under the control of a strong promoter, such as Ptrc, thus providing an excess of the thermosensitive repressor. In addition, more binding sites for the CI repressor can be introduced within the operator region of $\lambda P_R$ to reduce transcriptional starts at non-permissive temperatures, or engineered into regions downstream of the promoter element to hinder transcription at lower temperatures. Additionally, an antisense RNA for the regulated gene could be transcribed from a differently regulated promoter oriented in the opposite direction to $\lambda P_R$.

Arabinose Regulation. As previously discussed, a preferred regulatory system for triggering the expression switch when a microorganism is moved from a permissive to a non-permissive environment is the araC-$P_{BAD}$ system. The araC-$P_{BAD}$ system is a tightly regulated expression system which has been shown to work as a strong promoter induced by the addition of low levels of arabinose (see Guzman et al., *J. Bacteriol.* 177(14):4121-4130 (1995)). The araC-araBAD promoter is a bidirectional promoter controlling expression of the araBAD genes in one direction, and the araC gene in the other direction. For convenience, the portion of the araC-araBAD promoter that mediates expression of the araBAD genes, and which is controlled by the araC gene product, is referred to herein as $P_{BAD}$. For use in the vectors and systems described herein, a cassette with the araC gene and the araC-araBAD promoter should be used. This cassette is referred to herein as araC-$P_{BAD}$. The AraC protein is both a positive and negative regulator of $P_{BAD}$. In the presence of arabinose, the AraC protein is a positive regulatory element that allows expression of $P_{BAD}$. In the absence of arabinose, the AraC protein represses expression of $P_{BAD}$. This can lead to a 1,200-fold difference in the level of expression from $P_{BAD}$.

Enteric bacteria contain arabinose regulatory systems homologous to the araC araBAD system from *E. coli*. For example, there is homology at the amino acid sequence level between the *E. coli* and the *S. typhimurium* AraC proteins, and less homology at the DNA level. However, there is high specificity in the activity of the AraC proteins. For example, the *E. coli* AraC protein activates only *E. coli* $P_{BAD}$ (in the presence of arabinose) and not *S. typhimurium* $P_{BAD}$. Thus, a RADS can employ multiple arabinose regulatory sequences from multiple enterics to differentially regulate different components in the same system.

Maltose Regulation. Another preferred regulatory system for triggering the expression switch when high copy number is desired is the malT system. malT encodes MalT, a positive regulator of four maltose-responsive promoters ($P_{PQ}$, $P_{EFG}$, $P_{KBM}$, and $P_S$). The combination of malT and a mal promoter creates a tightly regulated expression system which has been shown to work as a strong promoter induced by the addition of maltose (see Schleif, "Two Positively Regulated Systems, ara and mal" pp. 1300-1309 in *Escherichia coli and Salmonella Cellular and Molecular Biology, Second Edition*, Neidhardt et al., eds., ASM Press, Washington, D.C., 1996. Unlike the araC-$P_{BAD}$ system, malT is expressed from a promoter ($P_T$) functionally unconnected to the other mal promoters. $P_T$ is not regulated by MalT. The malEFG-malKBM promoter is a bidirectional promoter controlling expression of the malKBM genes in one direction, and the malEFG genes in the other direction. For convenience, the portion of the malEFG-malKBM promoter that mediates expression of the malKBM gene, and which is controlled by the malT gene product, is referred to herein as $P_{KBM}$, and the portion of the malEFG-malKBM promoter that mediates expression of the malEFG gene, and which is controlled by the malT gene product, is referred to herein as $P_{EFG}$. Full induction of $P_{KBM}$ requires the presence of the MalT binding sites of $P_{EFG}$. For use in the vectors and systems described herein, a cassette with the malT gene and one of the mal promoters should be used. This cassette is referred to herein as malT-$P_{mal}$. In the presence of maltose, the MalT protein is a positive regulatory element which allows expression of $P_{mal}$.

As with arabinose and araC-$P_{BAD}$, regulation with maltose is useful for delayed RADS. This is because, once maltose is no longer supplied, it takes time for the maltose concentration to decline sufficiently to abolish induction by the MalT protein. To extend the time of temporary viability, it is preferred that strains for use with a maltose regulated RADS contain a deletion of the one or more elements of the mal operon. Such a deletion prevents metabolism of maltose, leading to a higher intracellular level of maltose. This results in a longer delay before maltose levels decline sufficiently to abolish induction by the MalT protein. Regulation with maltose is also useful since free maltose is not generally available in nature.

Delayed Death

As an alternative to rapid induction of the high copy number ori, the RADS can be designed to allow the host microorganism to remain viable for a limited time after the factor repressing the high copy number ori is withdrawn. This is referred to herein as a delayed RADS and results in RAVs which temporarily continue to be under the control of the lower copy number ori after host exposure to the environmental signal to switch to the high copy number ori. A preferred mechanism for delaying RAV high copy number is to base regulation on a trans regulatory element which must be degraded or diluted before the RAV can switch to the runaway condition. In such a system, upon moving the host microorganism from a high copy number repressed to a high copy number induced environment, a trans regulatory element which maintains the low copy number regime ceases to be produced. However, as long as the trans regulatory elements already on hand remain in sufficient quantity, the low copy number regime can remain in effect. Depending on the turnover of the trans regulatory element and the relationship between the amount of trans regulatory element on hand and the amount of trans regulatory element needed to maintain the low copy number regime, the low copy number regime can be maintained for several generations after transfer to the high copy number environment. Such temporary low copy number condition can be useful, for example, for allowing the host microorganism to colonize the host in a high copy number environment (e.g., without arabinose), such as an animal, but not remain indefinitely. As such, the RADS is a containment system even without the phage lysis genes described in WO96/40947. A delayed RADS is also useful when the desired gene product is harmful to the host cell, as in Example 3. Additionally, the delayed RADS can be used to depend an essential gene of a balanced lethal host system, such as asd, on an activatible control sequence such as araC$P_{BAD}$, to provide for a weakening of the cell wall upon immunization (and withdrawal of, in this case, arabinose). See Example 5.

A preferred trans regulatory element for use in a delayed RADS consists of the AraC protein and arabinose, its inducer. The AraC protein will continue to repress the high copy number orn operatively linked to $P_{BAD}$ until the concentration of arabinose falls below a critical level.

Vectors

As used herein, "vector" refers to an autonomously replicating nucleic acid unit. The present invention can be practiced with any known type of vector, including viral, cosmid, phasmid, and plasmid vectors. The most preferred type of vector is a plasmid vector.

As is well known in the art, plasmids and other vectors possess a wide array of promoters, multiple cloning sequences, etc., and these replicons can be used so that the amount of a synthesized foreign antigen can be controlled by the relative number of gene copies. For example, vectors with p15A, pBR and pUC replicons can be constructed, all of which are dependent on the polA gene encoding DNA polymerase I for their replication. Determination of whether replication of a vector is dependent on DNA polymerase I can be accomplished by growing the vector in a host with a temperature-sensitive polA mutation, such as χ1891 (see Table 1), and checking for vector maintenance as a function of temperature. Preferably, vectors used in RAD systems do not use antibiotic resistance to select for maintenance of the vector.

Preferred vectors have all of the essential elements of a RAV, that is (a) a gene encoding a desired gene product operably linked to a control sequence, (b) an origin of replication ("ori") conferring a low or intermediate copy number of the vector in the microorganism, and (c) an ori conferring a high copy number. Other elements which are part of any particular RADS may be on the vector or on another compatible vector or on the chromosome of the host microorganism.

Transfer Vectors. Rather than expressing an expression product directly, a microorganism can harbor a RAV for transfer to, and expression in, another cell in the environment into which the microorganism is placed. As used herein, a transfer vector is an expression vector which can be transferred from a RADS microorganism into a cell, and which directs the expression of an expression gene encoded by the transfer vector. It is intended that the transfer vector can contain any expression gene, including genes encoding antigens, immunomodulators, enzymes, and expression products that regulate gene expression or cellular activity in the recipient cell.

Preferred recipients for transfer vectors are cells of animals treated with the vector. For this purpose, RADS microorganisms containing a RAV transfer vector can be administered to an animal. It is preferred that the microorganisms invade cells of the animal in order to deliver the transfer vector. For this purpose, it is preferred that the microorganism lyses once it enters a cell of the animal. A preferred method for causing this lysis is an ELVS system, as described in WO96/40947. In that system, vector-borne lethal genes such as the phage lysis genes lys 13 and lys 19 are operably linked to P22 $P_R$ and the chromosome-encoded C2 repressor is operably linked to araCP$_{BAD}$. Introduction of the strain into an environment without arabinose, such as in an inoculated animal, results in a dilution of the C2 repressor present until the lethyl gene products kill the cell. In addition, the RADS with a RAV comprising a transfer vector can be designed as an ELVS that lysis due to regulated lysis genes inserted into the chromosome. Such expression of lysis genes would exhibit delayed expression such that lysis would only occur after the vertebrate cells with the transfer vector had entered a eukaryotic cell and conferred runaway vector replication. See also Example 6, which describes novel transfer vector adaptations to the RADS. When properly designed, the ELVS system is fully compatible with the RADS system and may share control elements. In this case, lysis of the cell, for example caused by an ELVS, will release the transfer vector inside the recipient cell. For expression of genes on the transfer vector in recipient cells, it is preferred that the expression genes be operatively linked to expression control sequences operable in the recipient cell. For example, where the recipient cell is an animal cell, it is preferred that the expression genes be operatively linked to a promoter functional in the animal and possess sequences ensuring polyadenylation of the mRNA. Methods for engineering such sequences are well known in the art.

Transfer vectors may also contain replication sequences operable in the recipient cell. This would allow replication of the transfer vector, resulting in increased or longer expression of expression genes present on the transfer vector. Transfer vectors are especially useful for expression of antigens and other proteins that need to be glycosylated or post-translationally modified in a eukaryotic cell. In this way a bacterial cell with a RAV/ELVS vector can be used for delivery of a protein requiring eukaryotic processing by expressing the protein from a transfer vector.

A preferred use for transfer vectors is in a RADS for stimulation of an immune response in an animal. For this purpose it is preferred that the bacteria is avirulent *Salmonella, Shigella, Yersinia,* or invasive *Escherichia* that would invade and then lyse to liberate a transfer vector designed for expression in cells of the animal. This can be useful in stimulating an immune response for viruses, parasites or against gamete antigens in which the antigens are normally glycosylated or post translationally modified in some way that can only be accomplished when the antigen product is synthesized within the eukaryotic cell.

The efficiency of transfer of transfer vector can be improved by including an endA mutation, mutations in recBC (with or without sbc suppressor mutations), and/or mutations in other nuclease genes. Such mutations can reduce degradation of the transfer vector upon lysis of the bacterial cell. It is also possible to influence the cell type and the mucosal surface to which the microorganism containing the transfer vector would adhere to and invade. This can be achieved by blocking or turning on the expression of specific adhesins and/or invasins.

Many vectors are known for DNA immunization or introduction into cells in an animal. Such vectors can be used as transfer vectors in microorganisms containing a RAV with an ELVS. In this case, the RADS provides a useful means for introducing such vectors into cells. Preferred promoters for expression of expression genes on transfer vectors are adenovirus, herpes virus and cytomegalovirus promoters. Expression of the expression gene can also be increased by placing a bacterial promoter upstream of the-eukaryotic promoter, so that the bacterial strain would already express some of the expression product. This expression product would be liberated upon lysis of the bacterium.

Preferred bacterial hosts/strains and vectors useful in, or useful for constructing, Environmentally Limited Viability Systems are listed in Tables 1 and 2.

TABLE 1

Bacterial Strains

| Strain | Description | Genotype |
|---|---|---|
| χ$^{3339}$ | *S. typhimurium* SL 13444 wild-type, isolated from liver of moribund mouse after peroral inoculation. | wild type, rpsL hisG |
| χ$^{3761}$ | *S. typhimurium* UK-1 wild-type strain obtained as a chicken passaged spleen isolate. | wild type |
| χ$^{8429}$ (MGN-2030) | Defined deletion derivative of *S. typhimurium* UK-1 containing ΔphoP24. See FIG. 2 for detail. | ΔphoP24 |

TABLE 1-continued

Bacterial Strains

| Strain | Description | Genotype |
|---|---|---|
| $\chi^{8431}$ (MGN-2084) | Defined deletion derivative of *S. typhimurium* UK-1 containing ΔphoP1918 (intact phoQ). See FIG. 2 for detail. | ΔphoP1918 |
| $\chi^{8448}$ | Defined deletion derivative of *S. typhimurium* UK-1 containing ΔaraBAD1923. Generated ΔaraBAD1923 deletion by conjugating $\chi^{3761}$ with MGN-617(pYA3484). See FIG. 2 for detail. | ΔaraBAD1923 |
| $\chi^{8449}$ | Defined deletion derivative of *S. typhimurium* SL 1344 containing ΔaraBAD1923. Generated ΔaraBAD1923 deletion by conjugating $\chi^{3339}$ with MGN-617(pYA3484). See FIG. 2 for detail. | ΔaraBAD1923 rpsL hisG |
| $\chi^{8477}$ | Defined deletion derivative of *S. typhimurium* UK-1 containing ΔaraE25. Generated ΔaraE25 deletion by conjugating $\chi^{3761}$ with MGN-617(pYA3485). See FIG. 2 for detail. | ΔaraE25 |
| $\chi^{8478}$ | Defined deletion derivative of *S. typhimurium* SL 1344 containing ΔaraE25. Generated ΔaraE25 deletion by conjugating $\chi^{3339}$ with MGN-617(pYA3485). See FIG. 2 for detail. | ΔaraE25 rpsL hisG |
| $\chi^{8514}$ | Defined deletion derivative of *S. typhimurium* UK-1 containing ΔphoP ΔasdA16. Generated ΔasdA16 deletion by conjugating $\chi^{8429}$ with MGN-617(pMEG-443). | ΔphoP24 ΔasdA16 |
| $\chi^{8516}$ | Defined deletion derivative of *S. typhimurium* UK-1 containing ΔaraBAD1923 ΔaraE25. Generated ΔaraE25 deletion by conjugating $\chi^{8477}$ with MGN-617(pYA3484). | ΔaraBAD1923 ΔaraE25 |
| $\chi^{8517}$ | Defined deletion derivative of *S. typhimurium* SL 1344 containing ΔaraBAD1923 ΔaraE25. Generated ΔaraBAD1923 deletion by conjugating $\chi^{8478}$ with MGN-617(pYA3484). | ΔaraBAD1923 ΔaraE25 rpsL hisG |
| $\chi^{8554}$ | Defined deletion derivative of *S. typhimurium* SL 1344 containing ΔasdA16. Generated by conjugating $\chi^{3339}$ with MGN-617(pMEG-443). | ΔasdA16 rpsL hisG |
| $\chi^{8581}$ | Defined deletion derivative of *S. typhimurium* UK-1 containing ΔaraBAD1923 ΔasdA16. Generated ΔasdA16 deletion by conjugating $\chi^{8448}$ with MGN-617(pMEG-443). | ΔaraBAD1923 ΔasdA16 |
| $\chi^{8582}$ | Defined deletion derivative of *S. typhimurium* SL 1344 containing ΔaraBAD1923 ΔasdA16. Generated ΔasdA16 deletion by conjugating $\chi^{8449}$ with MGN-617(pMEG-443). | ΔaraBAD1923 ΔasdA16 rpsL hisG |
| $\chi^{8583}$ | Defined deletion derivative of *S. typhimurium* UK-1 containing ΔaraBAD1923 ΔaraE25 ΔasdA16. Generated by conjugating $\chi^{8516}$ with MGN-617(pMEG-443). | ΔaraBAD1923 ΔaraE25 ΔasdA16 |
| $\chi^{8584}$ | Defined deletion derivative of *S. typhimurium* SL 1344 containing ΔaraBAD1923 ΔaraE25 ΔasdA16. Generated by conjugating $\chi^{8517}$ with MGN-617(pMEG-443). | ΔaraBAD1923 ΔaraE25 ΔasdA16 rpsL hisG |
| MGN-023 | An Asd⁻ Tet$^s$ derivative of *S. typhimurium* UK-1 $\chi^{3761}$ obtained after counter selection on fusaric acid of the pMEG-006 integrant. | ΔasdA16 |
| MGN-2267 | A sucrose resistant ΔasdA16 derivative of *S. choleraesuis*, MGN-2266. ΔphoP1918 attenuated host for runaway vectors regulated by arabinose controlled lacI. | ΔphoP1918 ΔasdA16 ΔilvG3(P$_{BAD}$.lacI) |
| MGN-2338 | A sucrose resistant ΔphoP1918 derivative of *S. typhimurium* UK-1, MGN-2237. This is an arabinose regulated expression strain for expression of antigens on both lambda P$_L$ and P$_{trc}$ expression vectors and runaway vectors. The P$_{BAD}$.cI857 insert in ΔasdA21 provides temperature and arabinose regulated expression of genes on λP$_L$ vectors. while P$_{BAD}$.lacI regulates P$_{trc}$ vectors. | ΔasdA21 (P$_{BAD}$.cI857) ΔilvG3 (P$_{BAD}$.lacI) ΔphoP1918 |
| MGN-4598 | A Δasd19::(P$_{BAD}$.C2) derivative of *S. typhimurium* UK-1, MGN-4597 obtained by plating on LB + 5% sucrose + DAP and then screening sucrose resistant isolates for Asd⁻ phenotype. | ΔaraBAD1923 ΔphoP24 ΔilvG:::(P$_{BAD}$ .lacI) Δasd19::(P$_{BAD}$.C2) |
| MGN-617 | E. coli K-12 ΔasdA4 suicide donor strain derived from SM10 λ pir, following transduction with P1 from $\chi^{2981}$ to Tet resistance and Asd⁻. Fusaric acid resistant isolate selected and confirmed to be Ap$^S$, Tet$^S$, and Asd⁻. | thi-1 thr-1 leuB6 supE44 tonA21 lacY1 recA RP4-2-Tc::Mu lpir, ΔasdA4 Δzhf-2::Tn10 |

TABLE 1-continued

Bacterial Strains

| Strain | Description | Genotype |
|---|---|---|
| MGN-966 | A defined ΔphoP22 derivative of S. typhimurium UK-1 MGN-965. obtained by plating MGN-965 on fusaric acid plates and screening for the Pho⁻ phenotype by sodium acetate soft agar overlay. This strain has the arabinose regulated P22 C2 repressor in Δasd and the arabinose regulated lacI repressor in ΔilvG. | ΔphoP22 ΔasdA19 ($P_{BAD}$.C2) ΔilvG3 ($P_{BAD}$.lacI) |
| SE-9 | Erysipelothrix rhusiopathiae virulent swine isolate of serotype 2. | wild-type |

TABLE 2

Plasmid Vectors

| Plasmid | Description |
|---|---|
| pMEG-104 | A P22 $P_R$ lysis and λ$P_L$ regulated asd containment vector on p15A replicon, obtained by deleting the 1.36 kb SalI fragment of pMEG-100 containing the Km cartridge. |
| pMEG-249 | A mobilizable suicide vector for $P_{BAD}$.lacI construct in ΔilvG3 derived from the suicide vector pMEG-149. This vector allows integration of the lacI gene driven by $P_{BAD}$ into the chromosome followed by sucrose counter-selection and screening for aminotriazole sensitivity. Provides an arabinose regulated control of expression of $P_{trc}$ and $P_{lac}$ RAVs. |
| pMEG-283 | A regulated pUC replicon/pSC101 plasmid with pUC ori driven by $P_{lac}$. This provides $P_{lac}$ control of the RNAII primer of replication. When in a $P_{BAD}$.lacI strain exhibits low copy number (6-8 copies) when arabinose is present to produce lacI from $P_{BAD}$.lacI in the host, however, without arabinose plasmid exhibits very high copy number (>300). |
| pMEG-368 | A suicide donor for ΔphoP24. The 3.1 kb EcoRV fragment of pMEG-359 (derived from pEG5381) cloned into the SmaI site of pMEG-149. This phoP24 deletion contains the trpA terminator with a new NotI site but does not modify the sequence of phoQ. |
| pMEG-375 | A chloramphenicol and ampicillin resistant mobilizable suicide vector derived from pMEG-149 by inserting the ~1.6 kb HincII-XmnI fragment of pYA800 containing the cat gene of pACYC184 into the SspI site of pMEG-149. |
| pMEG-446 | pMEG-446 contains the PCR product of Ery65 with signal sequence from Erysipelothrix rhusiopathiae strain E1-6P, ligated into pYA3332. |
| pMEG-525 | Runaway vector expressing Ery65 of Erysipelothrix rhusiopathiae from the 2.5 kb BstEII-HindIII fragment of pMEG-446 containing Ery65 with the signal sequence subcloned into BstEII-HindIII digested pMEG-283. |
| pMEG-546 | A runaway expression vector with an NcoI cloning site yet retaining the blue white lacZ screen for inserts. This plasmid was produced by inverse PCR of pMEG-283 using primers pMEG530-NCO1 and PMEG530-NCO2, introducing a unique NcoI site between the EcoRI site and the Ptrc promoter |
| pMEG-550 | A ΔphoP1918 suicide vector obtained by cloning the smaller EcoRV fragment from pMEG-549 (containing ΔphoP1918) into the PmeI site of pMEG-375. pMEG-549 was derived from inverse PCR using primers designed to delete phoP upstream sequences (−10 and −35) and ATG through TAA (phoP1918) of pEG5381 from E. Groisman. |
| pMEG-573 | A runaway vector expressing the SeM protein of Streptococcus equi without the signal sequence. Obtained by PCR amplification of sem from pSEM06 using primers SeM444-474NcoI and SeM1265-1233Bam and cloning into the NcoI and BamHI sites of pMEG-546. |
| pMEG-575 | A λ$P_L$ expression vector for SeM protein of Streptococcus equi without signal sequence, obtained by PCR amplification of sem from pSEM06 using primers SeM404-474NcoI and SeM1265-1233Bam and cloning into the NcoI and BamHI sites of pMEG-547, a $P_L$ expression vector with pBR ori. Expression is regulated by lambda CI repressor in $P_{BAD}$.CI host. |
| pMEG-611 | A mobilizable suicide vector for introduction of ΔasdA19, derived from pMEG-375 by inserting the ~4.6 kbAccI(blunted)-SphI fragment of pMEG-221 containing the P22 C2 repressor under the control of AraCP$_{BAD}$ in the ΔasdA16 deletion into the SphI-PmeI sites of pMEG-375. |
| pMEG-771 | A runaway replicon expression vector obtained by removing the EagI-XhoI fragment of pMEG-546 containing the lac promoter, and replacing the lac promoter with the HindIII-SalI fragment of pMEG-104 containing the 5S T1 T2 transcription terminator and the P22 $P_R$. |
| pMEG-776 | A chloramphenicol and ampicillin resistant suicide vector for inserting ΔendA3 of S. typhimurium into the chromosome, obtained by ligating the BamHI-NotI ΔendA fragment from pMEG-761 into the BamHI-NotI sites of pMEG-375. |
| pMEG-825 | P22 $P_R$ expression vector for SeM protein of Streptococcus equi without signal sequence, obtained by inserting the 829 bp BamHI-NcoI SeM fragment from |

TABLE 2-continued

Plasmid Vectors

| Plasmid | Description |
|---|---|
| | pMEG-573 into BamHI-NcoI digested pMEG-818, a P22 $P_R$ expression vector with pBR ori. Expression is regulated by P22 C2 repressor in $P_{BAD}$.C2 host. |
| pMEG-826 | $P_{trc}$ expression vector for SeM protein of *Streptococcus equi* without signal sequence, obtained by inserting the 829 bp BamHI-NcoI SeM fragment from pMEG-573 into BamHI-NcoI digested pYA3333, a $P_{trc}$ expression vector with pBR ori. Expression is regulated by LacI repressor in $P_{BAD}$.lacI host. |
| pYA3332 | A lacZα negative derivative of asd plasmid pYA3098 with the p15A origin of replication. |
| pYA3450 | araC $P_{BAD}$ SD-asd vector derived from pMEG-247 with deletions of 35 bp between $P_{BAD}$ and asd gene and 24 bp deletion in between the stop codon of asd and the HindIII site of pMEG-247. |
| pYA3484 | Suicide vector derivative of pMEG-375 to generate ΔaraBAD1923. See FIG. 6 |
| pYA3485 | Suicide vector derivative of pMEG-375 to generate ΔaraE25. See FIG. 7 |
| pYA3488 | araC $P_{BAD}$ P22 c2 SD-asd vector. P22 c2 gene is inserted NheI-EcoRI site of pYA3450 |
| pYA3530 | araC $P_{BAD}$ SD-GTG asd vector. Asd starting codon ATG of pYA3450 is changed to GTG by site-directed mutagenesis. See FIG. 20 |
| pYA3531 | araC $P_{BAD}$ P22 c2 SD-GTG asd vector. Asd starting codon ATG of pYA3488 is changed to GTG by site-directed mutagenesis. See FIG. 21 |
| pYA3535 | A derivative of pMEG-771 to include a lacRB (LacI repressor binding) site in between P22 $P_R$ and pUC RNAII. See FIG. 11 for detail. |

As previously discussed, the host cells of the present invention also have a desired recombinant gene encoding the polynucleotide of a desired gene product such as a polypeptide or a mRNA. The choice of desired gene is not narrowly limited and may include genes encoding, for example, viral, bacterial, fungal or parasite antigens, etc.

In order for the desired gene to be useful in the present invention, the gene must be expressed. Gene expression means that the information encoded in the sequence of DNA bases is transformed into a physical product in the form of a RNA molecule, polypeptide or other biological molecule by the biochemical mechanisms of the cell in which the gene is located. The biological molecule so produced is called the gene product. The term gene product as used here refers to any biological product or products produced as a result of expression of the gene. The gene product may be, for example, an RNA molecule, a peptide, or a product produced under the control of an enzyme or other molecule that is the initial product of the gene, i.e., a metabolic product. For example, a gene may first control the synthesis of an RNA molecule that is translated by the action of ribosomes into an enzyme that controls the formation of glycans in the environment external to the original cell in which the gene was found. The RNA molecule, the enzyme, and the glycan are all gene products as the term is used here. Any of these as well as many other types of gene products, such as glycoproteins and polysaccharides, will act as antigens if introduced into the immune system of an animal. Protein gene products, including glycoproteins and lipoproteins, are preferred gene products for use as antigens in vaccines.

Preferred embodiments of the present invention relate to the use of the above-described RADS microorganisms as constituents of live vaccines. In these cases, the desired recombinant gene would encode an antigen of a fungal, bacterial, parasitic, or viral disease agent. Live vaccines are particularly useful where localized immunity to the disease agent is important and might be a first line of defense. However, in this case it is essential that the host cells be attenuated to the individual being vaccinated.

Preferably, the host cells used in live vaccines are attenuated derivatives of pathogens. Most preferably, the attenuated derivatives are able to attach to, invade and persist in the gut-associated lymphoid tissue (GALT) or bronchial-associated lymphoid tissue (BALT). Such attenuated host cells are preferred because they are known to be able to persist in the inoculated animal, causing exposure to the antigen for an extended time period. Such a long exposure period is known to be highly effective in inducing an immunogenic response to the antigen.

Attenuation can be conferred upon the microbes by any known means, including chemical mutagenesis and the use of various recombinant genes. Preferred methods of conferring attenuation render the host cells unable to revert to the pathogenic condition. The most preferred methods of conferring attenuation on host cells are though the introduction of stable mutations or gene insertions by recombinant methods. Non-limiting examples of such methods include (1) introducing mutations that impose a requirement for aromatic amino acids and vitamins derived from precursors in this pathway (Stocker et al., 1983, *Dev. Biol. Stand.* 53:47-54; Hoiseth and Stocker, 1981, *Nature* 291:238-9); (2) mutating genes for global regulators such as cya and cyp (U.S. Pat. Nos. 5,389,368; 5,855,879; 5,855,880; 5,294,441 and 5,468,485), phoP (U.S. Pat. No. 5,424,065), ompR (Dorman et al., 1989, *Infect. Immun.* 57:2136-40), and poxA (U.S. patent application Ser. No. 08/829,402); (3) mutating genes for lipopolysaccharide (LPS) synthesis, such as galE (Germanier et al., 1975, *J. Infect. Dis.* 131:553-8), although this alone may be insufficient (Hone et al., 1988 *Infect. Immun.* 56:1325-33); (4) mutating genes needed for colonization of deep tissues, such as cdt (U.S. Pat. No. 5,387, 744); or (5) by preventing expression of genes for proteases required at high temperature, such as htrA (Johnson et al., 1991, *Mol. Microbiol.* 5:401-7).

Once rendered attenuated, the microbes can serve as the immunogenic component of a vaccine to induce immunity against the microbe. Thus, the use of any microbe possessing the characteristics of the host cells described supra, including avirulence, are contemplated by this invention, including but not limited to *E. coli, Salmonella* spp., *E. coli-S. typhimurium* hybrids, *Shigella* spp., *Yersinia* spp., *Pasteurella* spp., *Legionella* spp. or *Brucella* spp. Preferred microbes are members of the genus *Salmonella* such as *S. typhimurium, S. typhi, S. paratyphi, S. gallinarum, S. enteritidis, S. choleraesius, S. arizona*, or *S. dublin*.

Live bacterial antigen delivery systems. Preferred hosts for use as antigen delivery systems are enteric bacteria. As used herein, the terms "antigen delivery system" and "antigen delivery microorganism" refer to a microorganism that produces an antigen or that harbors a transfer vector encoding an antigen. As used herein, "enteric bacteria" refers to any *Enterobacteriaceae*. Many of the preferred genes and regulatory elements described herein are operable in most enteric bacteria, thus allowing use of the many well developed *E. coli* and *Salmonella* regulatory systems. Most preferably, the bacterial host is an attenuated derivative of a pathogenic *Salmonella*.

In one embodiment of the system described herein, an attenuated derivative of a pathogenic microbe that attaches to, invades and persists in the gut-associated lymphoid tissue (GALT) or bronchial-associated lymphoid tissue (BALT) is used as a carrier of the gene product which is used for stimulating immune responses against a pathogen or allergen. Attenuated does not mean that a microbe of that genus or species can not ever cause disease, but that the particular microbe being used is attenuated with respect to the particular animal being treated. The microbe may belong to a genus or even a species that is normally pathogenic, but must belong to a strain that is attenuated. By pathogenic is meant capable of causing disease or impairing normal physiological functioning. Attenuated strains are incapable of inducing a full suite of symptoms of the disease that is normally associated with its virulent pathogenic counterpart. Microbes as used herein include bacteria, protozoa, parasites, unicellular fungi, and multicellular fungi.

*Shigella* or an enteroinvasive *E. coli* can be useful in antigen delivery systems since invasion into colonic mucosa could stimulate lymphoid tissues adjacent to the colon, so as to stimulate a strong mucosal immune response in the reproductive tract. Rectal immunization can be effective because of anatomical features such as the proximity of lymph nodes and lymphatics to the colon.

In order for a vaccine to be effective in inducing antibodies, the antigenic material must be released in such a way that the antibody-producing mechanism of the vaccinated animal can come into play. Therefore the microbe carrier of the gene product must be introduced into the animal. In order to stimulate a preferred response of the GALT or BALT cells as discussed previously, introduction of the microbe or gene product directly into the gut or bronchus is preferred, such as by oral administration, gastric intubation or in the form of intranasal, although other methods of administering the vaccine, such as intravenous, intramuscular, subcutaneous injection or intramammary or intrapenial or vaginal administration, are possible.

When the attenuated microbe is used as a vaccine, the antigen needs to become available to the animal's immune system. This may be accomplished when the carrier microbe dies so that the antigen molecules are released. Of course, the use of "leaky" attenuated mutants that release the contents of the periplasm without lysis is also possible. Alternatively, a gene may be selected that controls the production of an antigen that will be made available by the carrier cell to the outside environment prior to the death of the cell.

Antigens. Live recombinant RADS microorganisms can be used to deliver any product that can be expressed in the host microorganism. Preferred expression products for this purpose are antigens. For example, antigens can be from bacterial, viral, mycotic and parasitic pathogens, to protect against bacterial, viral, mycotic, and parasitic infections, respectively; gametes, provided they are gamete specific, to block fertilization; and tumor antigens, to halt cancers. It is specifically contemplated that antigens from organisms newly identified or newly associated with a disease or pathogenic condition, or new or emerging pathogens of animals or humans, including those now known or identified in the future, can be used in a RADS. Furthermore, antigens for use in a RADS are not limited to those from pathogenic organisms. The selection and recombinant expression of antigens has been previously described by Schödel (1992) and Curtiss (1990). Immunogenicity of the microorganisms can be augmented and/or modulated by constructing strains that also express genes for cytokines, adjuvants, and other immunomodulators.

Some examples of microorganisms useful as a source for antigen are listed below. Theses include microorganisms for the control of plague caused by *Yersinia pestis* and other *Yersinia species* such as *Y. pseudotuberculosis* and *Y. enterocolitica*, of gonorrhea caused by *Neisseria gonorrhoea*, of syphilis caused by *Treponema pallidum*, and of venereal diseases as well as eye infections caused by *Chlamydia trachomatis*. Species of *Streptococcus* from both group A and group B, such as those species that cause sore throat or heart diseases, *Erisipelothrix rhusiopathiae, Neisseria meningitidis, Mycoplasmapneumoniae* and other *Mycoplasma* species, *Hemophilus influenza, Bordetella pertussis, Mycobacterium tuberculosis, Mycobacterium leprae, Bordetella* species, *Escherichia coli, Streptococcus equi, Streptococcus pneumoniae, Brucella abortus, Pasteurella hemolytica* and *P. multocida, Vibrio cholera, Shigella* species, *Borrellia* species, *Bartonella* species, *Heliobacter pylori, Campylobacter* species, *Pseudomonas* species, *Moraxella* species, *Brucella* species, *Francisella* species, *Aeromonas* species, *Actinobacillus* species, *Clostridium* species, *Rickettsia* species, *Bacillus* species, *Coxiella* species, *Ehrlichia* species, *Listeria* species, and *Legionella pneumophila* are additional examples of bacteria within the scope of this invention from which antigen genes could be obtained. Viral antigens can also be used in a RADS. Viral antigens can be used in antigen delivery microorganisms directed against viruses, either DNA or RNA viruses, for example from the classes Papovavirus, Adenovirus, Herpesvirus, Poxvirus, Parvovirus, Reovirus, Picornavirus, Myxovirus, Paramyxovirus, Flavivirus or Retrovirus. Antigen delivery microorganisms using antigens of pathogenic fungi, protozoa and parasites can also be used.

Certain vaccine embodiments comprise utilization of microorganisms comprising a RADS system where the desired gene encodes an allergen. Such a vaccine may be used in an exposure regimen designed to specifically desensitize an allergic host. Allergens are substances that cause allergic reactions in an animal that is exposed to them. Allergic reactions, also known as Type I hypersensitivity or immediate hypersensitivity, are vertebrate immune responses characterized by IgE production in conjunction with certain cellular immune reactions. Many different materials may be allergens, such as animal dander and pollen, and the allergic reaction of individual animals will vary for any particular allergen. It is possible to induce tolerance to an allergen in an animal that normally shows an allergic response. The methods of inducing tolerance are well-known and generally comprise administering the allergen to the animal in increasing dosages.

Recombinant attenuated *Salmonella* are capable of stimulating strong mucosal, systemic and cellular immune responses against foreign antigens and thus against the pathogen that is the source of the foreign antigen. It is not necessary that the antigen gene be a complete gene as present in the parent organism, which was capable of producing or regulating the production of a macromolecule, for example, a functioning polypeptide. It is only necessary that the gene be capable of serving as the template used as a guide in the production of an antigenic product. The product may be one that was not found in that exact form in the parent organism. For example, a functional gene coding for a polypeptide antigen comprising 100 amino acid residues may be transferred in part into a carrier-microbe so that a peptide comprising only 75, or even 10, amino acid residues is produced by the cellular mechanism of the host cell. Alternatively, if the amino acid sequence of a particular antigen or fragment thereof is known, it is possible to chemically synthesize the DNA fragment or analog thereof by means of automated gene synthesizers, PCR, or the like and introduce said DNA sequence into the appropriate expression vector. At the other end of the spectrum is a long section of DNA coding for several gene products, one or all of which can be antigenic.

Multiple antigens can also be expressed by a recombinant avirulent *Salmonella* strain. In addition, antigens, or even parts of antigens, that constitute a B cell epitope or define a region of an antigen to which an immune response is desired, can be expressed as a fusion to a carrier protein that contains a strong promiscuous T cell epitope and/or serves as an adjuvant and/or facilitates presentation of the antigen to enhance, in all cases, the immune response to the antigen or its component part. This can easily be accomplished by genetically engineering DNA sequences to specify such fusions for expression by attenuated strains. Fusion to tenus toxin fragment C, CT-B, LT-B and hepatitis virus B core are particularly useful for these purposes, although other epitope presentation systems are well known in the art.

In order for the expression gene to be effective in eliciting an immune response, the expression gene must be expressed, which can be accomplished as described above. In order for an antigen delivery microorganism to be effective in immunizing an individual, the antigenic material must be released in such a way that the immune system of the vaccinated animal can come into play. Therefore the live avirulent microorganism must be introduced into the animal. In order to stimulate a preferred response of the GALT or BALT cells as discussed previously, introduction of the microbe or gene product directly into the gut or bronchus is preferred, such as by oral administration, intranasal administration, gastric intubation or in the form of aerosols, although other methods of administering the antigen delivery microorganism, such as intravenous, intramuscular, subcutaneous injection or intramammary, intrapenial, intrarectal, or vaginal administration, is possible.

Antigen Delivery Compositions. A preferred use of antigen delivery microorganisms is as vaccines for stimulating an immune response to the delivered antigens. Oral immunization in a suitable animal host with live recombinant *Salmonella* vaccine strains leads to colonization of the gut-associated lymphoid tissue (GALT) or Peyer's patches, which leads to the induction of a generalized mucosal immune response to both *Salmonella* antigens and the foreign antigens synthesized by the recombinant *Salmonella* (Curtiss et al., *Adv. Exp. Med. Biol.* 251:33-47 (1989)). Further penetration of the vaccine strain into the mesenteric lymph nodes, liver and spleen augments the induction of systemic and cellular immune responses directed against *Salmonella* antigens and the foreign antigens made by the recombinant *Salmonella* (Doggett and Curtiss (1992)). Thus the use of recombinant avirulent *Salmonella* vaccines for oral immunization stimulates all three branches of the immune system, particularly important when immunizing against infectious disease agents which colonize on and/or invade through mucosal surfaces.

By vaccine is meant an agent used to stimulate the immune system of a living organism so that an immune response occurs. Preferably, the vaccine is sufficient to stimulate the immune system of a living organism so that protection against future harm is provided. Immunization refers to the process of inducing a continuing high level of antibody and/or cellular immune response in which T-lymphocytes can either kill the pathogen and/or activate other cells (for example, phagocytes) to do so in an organism, which is directed against a pathogen or antigen to which the organism has been previously exposed. Although the phrase "immune system" can encompass responses of unicellular organisms to the presence of foreign bodies, that is, interferon production, as used herein the phrase is restricted to the anatomical features and mechanisms by which a multicellular organism responds to an antigenic material which invades the cells of the organism or the extra-cellular fluid of the organism. The antibody so produced may belong to any of the immunological classes, such as immunoglobulins A, D, E, G or M. Of particular interest are vaccines which stimulate production of immunoglobulin A (IgA) since this is the principle immunoglobulin produced by the secretory system of warm-blooded animals, although the vaccines described herein are not limited to those which stimulate IgA production. For example, vaccines of the nature described herein are likely to produce a broad range of other immune responses in addition to IgA formation, for example, cellular and humoral immunity. Immune responses to antigens are well studied and widely reported. A survey of immunology is given in Paul, Ed. (1999), *Fundamental Immunology*, fourth ed., Philadelphia: Lippincott-Raven, Sites et al., *Basic and Clinical Immunology* (Lange Medical Books, Los Altos, Calif., 1994), and Orga et al., Handbook of Mucosal Immunology (Academic Press, San Diego, Calif., 1994). Mucosal immunity is also described by Ogra et al., Eds. (1999), *Mucosal Immunology*, second ed., Academic Press, San Diego.

An individual treated with a vaccine of the invention is defined herein as including all vertebrates, for example, mammals, including domestic animals and humans, various species of birds, including domestic birds, particularly those of agricultural importance. Preferably, the individual is a warm-blooded animal.

The dosages of live recombinant vaccines required to elicit an immune response will vary with the antigenicity of the cloned recombinant expression product and need only be a dosage sufficient to induce an immune response typical of existing vaccines. Routine experimentation will easily establish the required dosage. Typical initial dosages of vaccine for oral administration could be $1\times10^7$ to $1\times10^{11}$ CFU depending upon the size and age of the individual to be immunized. Administering multiple dosages can also be used as needed to provide the desired level of protective immunity. The pharmaceutical carrier in which the vaccine is suspended can be any solvent or solid material for encapsulation that is non-toxic to the inoculated animal and compatible with the carrier organism or antigenic gene product. Suitable pharmaceutical carriers include liquid carriers, such as normal saline and other non-toxic salts at or near physiological concentrations, and solid carriers not used for humans, such as talc or sucrose, or animal feed.

Adjuvants may be added to enhance the antigenicity if desired. When used for administering via the bronchial tubes, the vaccine is preferably presented in the form of an aerosol.

Immunization with a pathogen derived gene product can also be used in conjunction with prior immunization with the attenuated derivative of a pathogenic microorganism acting as a carrier to express the gene product specified by a recombinant gene from a pathogen. Such parenteral immunization can serve as a booster to enhance expression of the secretory immune response once the secretory immune system to that pathogen-derived gene product has been primed by immunization with the carrier microbe expressing the pathogen derived gene product to stimulate the lymphoid cells of the GALT or BALT. The enhanced response is known as a secondary, booster, or anamnestic response and results in prolonged immune protection of the host. Booster immunizations may be repeated numerous times with beneficial results.

Although it is preferred that antigen delivery microorganisms be administered by routes that stimulate a mucosal immune response, namely oral, intranasal, intravaginal, and interrectal, these microorganisms can also be delivered intramuscularly, intravenously, and in other parenteral routes. Administration of an antigen delivery microorganism can also be combined with parenteral administration of purified antigenic components. In case where an ELVS is used to control or treat cancer, it is preferred that the ELVS be administered parenterally.

Adaptation of RADS to Useful Host Strains. Avirulent strains of *S. typhimurium* are known to be totally attenuated and highly immunogenic in mice, chickens, and pigs, inducing protective immunity to infection with 10,000 times a lethal dose with the virulent wild-type strain. Similarly, avirulent strains of *S. choleraesuis* are attenuated and-immunogenic in mice and pigs and also offer significant protective immunity. Avirulent strains: of *S. dublin* have been isolated and tested and found to be avirulent, immunogenic, and protective in calves. Attenuated *S. typhi* strains have also been constructed and found to induce significant immune responses in human volunteers. Attenuated derivatives of *Vibrio cholerae* and *Shigella flexneri* have also been constructed and used as vaccines to induce significant immune responses in human volunteers. *Mycobacterium bovis* strain BCG has also been used to orally immunize humans. Attenuated *Listeria monocytogenes* has also been used as a live vaccine for immunization of mice. In addition to serving as vaccines to immunize animals and human hosts against infection with related virulent wild-type strains, avirulent derivatives of the above cited microorganisms can also be used as antigen delivery vectors by genetically engineering them to express foreign antigens. These antigens could be from bacterial, viral, fungal and parasitic pathogens or they could be allergens or they could be gamete specific antigens in a contraceptive vaccine or tumor antigens in anti cancer vaccines. Immunization of animal and/or human hosts with these live recombinant avirulent vaccines is known to induce mucosal, systemic and cellular immune responses directed against the foreign antigen and against the pathogen from which the gene specifying the foreign antigen was isolated or against allergens or against sperm or ova or against tumor cells, respectively.

Bacterial pathogens can be attenuated by introducing deletion mutations in various genes as described above or as known to the skilled artisan. Any of these strains are suitable for introduction of a RADS of the sort disclosed herein, although modifications would be needed to make the system operable in gram-positive bacteria. Specifically these modifications would require modification of Shine-Dalgarno sequences to permit translation of mRNA, and slight changes in promoter sequences to cause transcription to be more efficient, as is known in the art.

Administration of a live vaccine of the type disclosed above to an animal may be by any known or standard technique. These include oral ingestion, gastric intubation, or broncho-nasal spraying. All of these methods allow the live vaccine to easily reach the GALT or BALT cells and induce antibody formation and are the preferred methods of administration. Other methods of administration, such as intravenous injection to allow the carrier microbe to reach the animal's blood stream may be acceptable. Intravenous, intramuscular or intramammary injection is also acceptable with other embodiments of the invention, as is described later.

Since preferred methods of administration are oral ingestion, aerosol spray and gastric intubation, preferred carrier microbes are those that belong to species that home preferentially to any of the lymphoepithelial structures of the intestines or of the bronchi of the animal being vaccinated. Preferably, these strains are attenuated derivatives of enteropathogenic strains produced by genetic manipulation of enteropathogenic strains. Strains that home to Peyer's patches and thus directly stimulate production of IgA are most preferred. In animals these include specific strains of *Salmonella*, and *Salmonella-E. coli* hybrids that home to the Peyer's patches.

The dosages required will vary with the antigenicity of the gene product and need only be an amount sufficient to induce an immune response typical of existing vaccines. Routine experimentation will easily establish the required amount. Typical initial dosages of vaccine could be 0.001-0.1 mg antigen/kg body weight, with increasing amounts or multiple dosages used as needed to provide the desired level of protection.

The pharmaceutical carrier in which the vaccine is suspended or dissolved may be any solvent or solid or encapsulated in a material that is non-toxic to the inoculated animal and compatible with the carrier organism or antigenic gene product. Suitable pharmaceutical carriers include liquid carriers, such as normal saline and other non-toxic salts at or near physiological concentrations, and solid carriers not used for humans, such as talc, sucrose, and feed for farm animals. Adjuvants may be added to enhance the antigenicity if desired. When used for administering via the bronchial tubes, the vaccine is preferably presented in the form of an aerosol.

Immunization with a pathogen-derived gene product can also be used in conjunction with prior immunization with the attenuated derivative of a pathogenic microorganism acting as a carrier to express the gene product specified by a recombinant gene from a pathogen. Such parenteral immunization can serve as a booster to enhance expression of the secretory immune response once the secretory immune system to that pathogen-derived gene product has been primed by immunization with the carrier microbe expressing the desired gene product to stimulate the lymphoid cells of the GALT or BALT. The enhanced response is known as a secondary, booster, or anamnestic response and results in prolonged immune protection of the host. Booster immunizations may be repeated numerous times with beneficial results.

In other embodiments of the invention, a recombinant attenuated derivative of a pathogenic microbe can be used to express, in the animal host, gene products that are therapeutic in the inoculated animal. Non-limiting examples of such products include lymphokines or cytokines to modulate the immune response (Saltzman et al., 1996, *Cancer Bio. Ther. Radiol. Pharm.* 11: 145-153; Saltzman et al., 1997, *J. Pediatric. Surg.* 32:301-306; Whittle et al., 1997, *J. Med. Microbiol.* 46:1029-1038, 1997; Dunstan et al., 1996, *Infect. Immun.* 64:2730-2736), sperm-specific and egg-specific autoantigens to arrest fertility (U.S. Pat. No. 5,656,488), blood products such as clotting factors, specific antibodies, e.g., which bind to tumors or pathogens such as viruses, fungi, parasites, or bacteria; growth factors, essential enzymes or structural proteins which are insufficiently produced in the host, ribozymes or antisense RNA which cleaves or inactivates a nucleic acid encoding an undesirable gene product (e.g., a gene product essential for tumor metastasis or angiogenesis of tumors; a gene product essential for a pathogen to cause disease), or enzymes that have the potential to convert prodrugs into toxic drugs within a tumor cell mass in an individual with a solid tumor (Pawelek et al., 1997, *Cancer Res.* 57:4537-44).

Because the avirulent microbes of this invention are able to traverse a variety of immunocompetent structures including the GALT, mesenteric lymph nodes and spleen, such microbes may also be used to modulate the immune system by producing a variety of immunoregulatory products. Accordingly, one or more genes encoding immunoregulatory proteins or peptides may be recombinantly introduced as a desired gene into the attenuated microbes such that the microbes are capable of taking up residence in the appropriate immunocompetent tissue and express the recombinant desired gene product to suppress, augment or modify the immune response in the host. Nonlimiting examples of immunoregulatory molecules include colony stimulating factors (macrophage, granulocyte, or mixed), macrophage chemotoxin, macrophage inhibition factor, leukocyte inhibitory factors, lymphotoxins, blastogenic factor, interferons, and interleukins.

Derivatives of attenuated microbes are also contemplated to be within the scope of this invention. By derivative is meant sexually or asexually derived progeny and mutants of the avirulent strains including single or multiple base substitutions, deletions, insertions or inversions which retain the basic functioning of the host cells previously described.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims that follow the examples.

EXAMPLES

Example 1

Construction of Bacterial Host Strains as Attenuated Antigen Delivery Hosts for RAVs.

Figure 2:
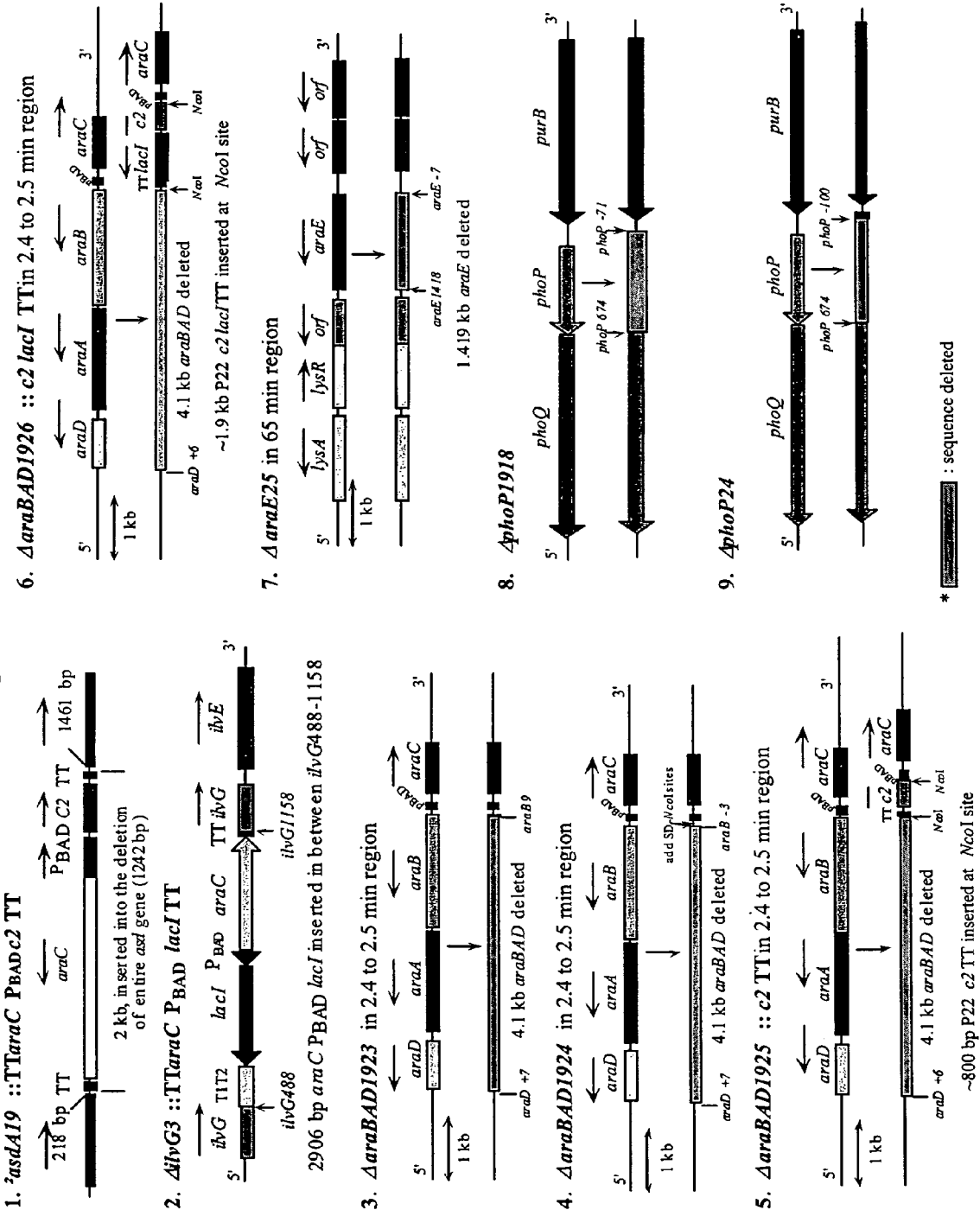
FIG. 2 depicts various deletion and deletion/insertion mutations needed for the maintenance of RAVs as components of regulated antigen delivery systems (RADSs), and deletion mutations suitable for attenuation of vaccine strains to render them avirulent while retaining immunogenicity.
Figure 3:
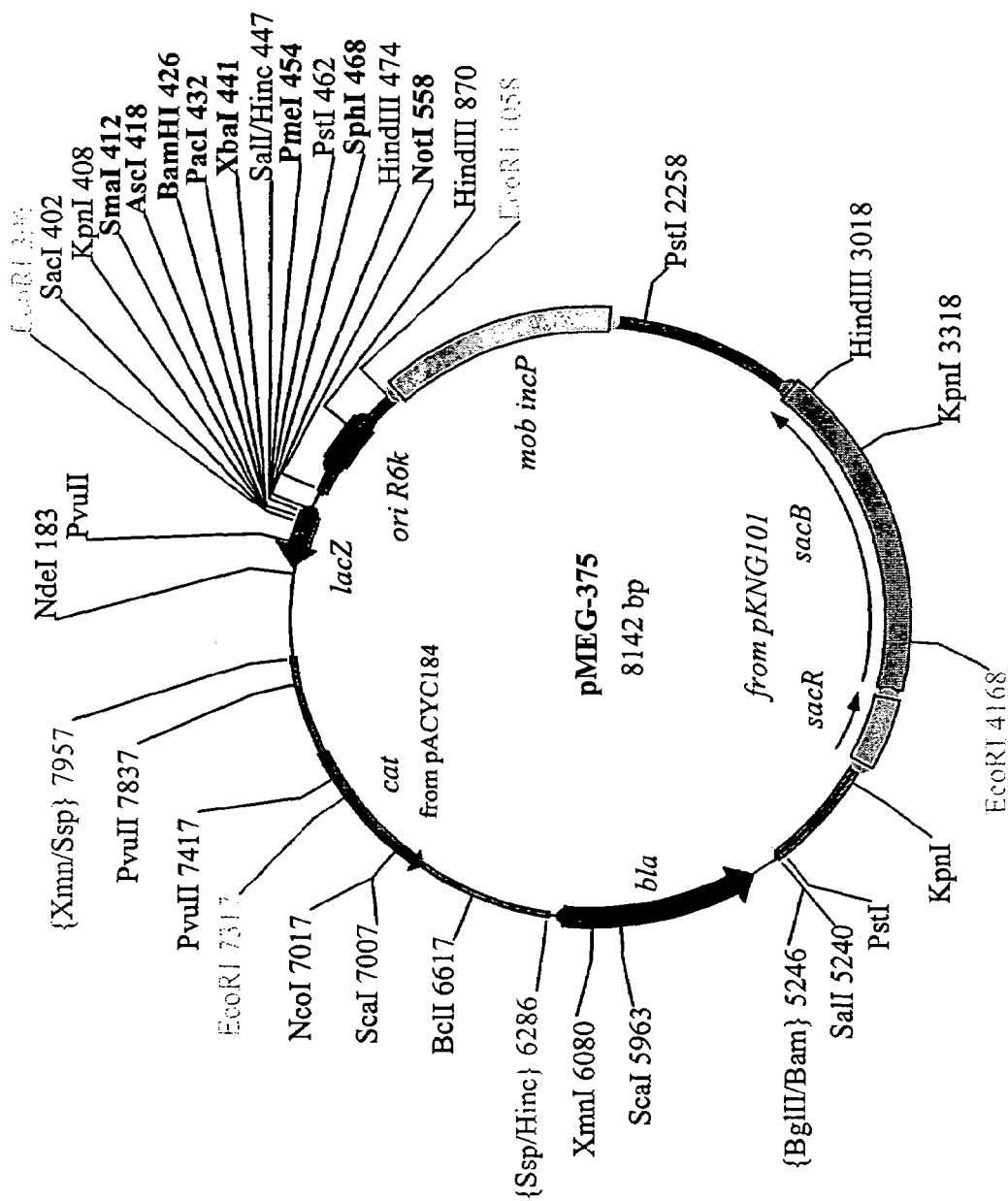
FIG. 3 depicts mobilizable suicide vector pMEG-375.
Figure 4:
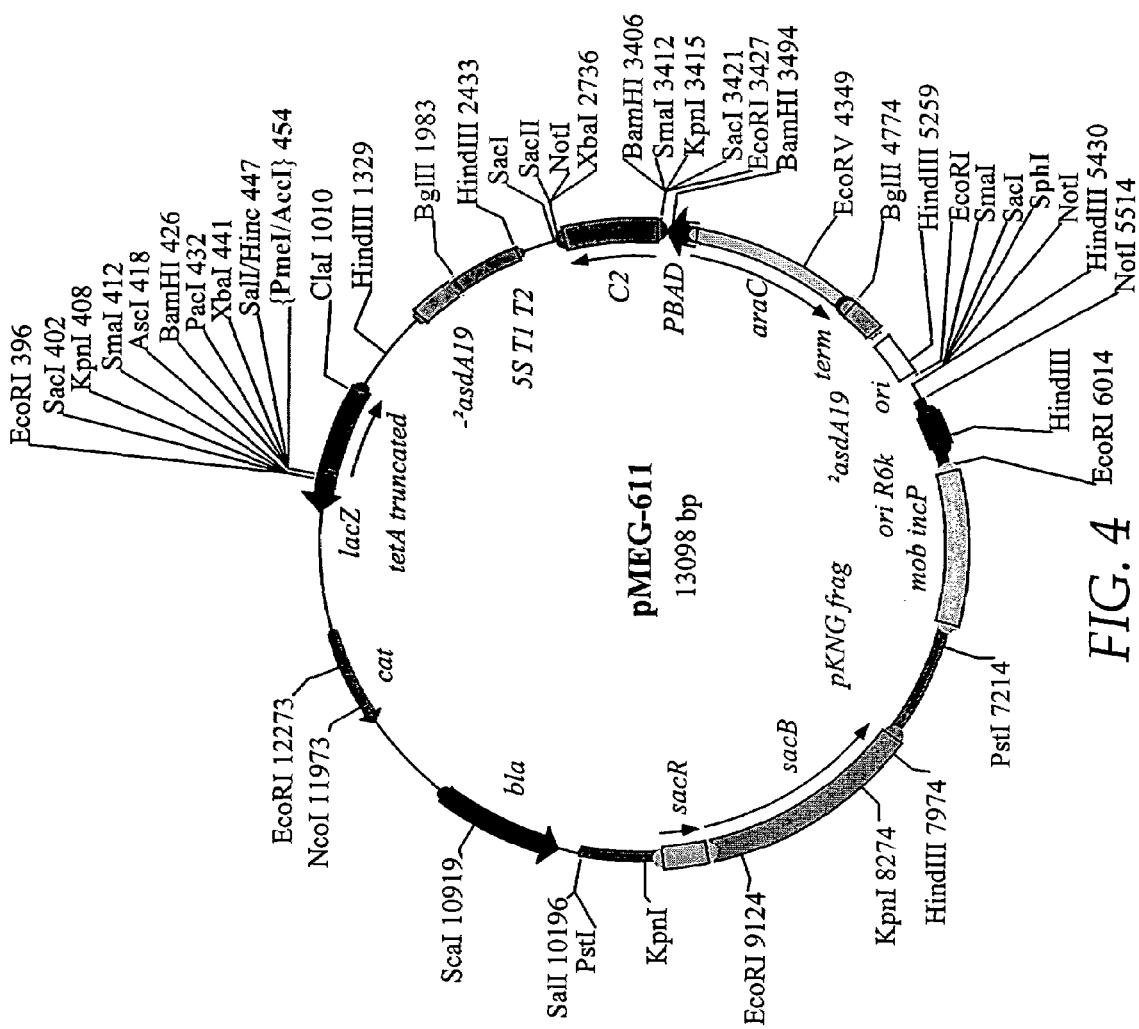
FIG. 4 depicts suicide vector pMEG-611, for delivery of $\Delta asdA19::TTaraCP_{BAD}c2TT$.

The RADSs are dependent upon the presence of RAV constructions as described in Example 2 and the presence of chromosomal deletion mutations, often with insertions, to permit regulation of genes on the RAVs under permissive versus non-permissive conditions. Deletion/insertion mutations 1 and 2 in FIG. 2 are generally needed for the maintenance of most RAVs described although the deletion/insertion mutation 2 is sufficient for maintenance and function of one of the RAVs described in a subsequent example. The introduction of mutations such as $\Delta smdA19::TTaraCP_{BAD}c2TT$ and $\Delta ilvG3::TTaraCP_{BAD}lacITT$ is best accomplished by the use of suicide vectors. As stated above, the $araCP_{BAD}$ regulatory system enables arabinose supplied as a free sugar to bind to the AraC protein which acts as an activator of transcription commencing at the $P_{BAD}$ promoter thus causing synthesis, after translation of the c2 and/or lad mRNA, of the repressor protein products C2 and/or LacI. The molecular construction of the $TTaraCP_{BAD}c2TT$ product and its insertion into the 1244 bp deletion of the asd gene as well as the molecular genetic construction of the $TTaraCP_{BAD}lacITT$ construction and its insertion into the $\Delta ilvG3$ mutation are described in WO96/40947. (It should be noted that the ilvG3 mutation was incorrectly designated $\Delta relA3$ in WO96/40947.) These molecular constructs can be placed in a suicide vector such as pMEG-375 (FIG. 3), which possesses genes for ampicillin and chloramphenicol resistance to select for primary recombinants with the suicide vector inserted into the chromosome and also the sacB gene encoding levansucrase for the hydrolysis of sucrose. The latter permits selection of recombinants losing the suicide vector by a second recombination event, hopefully associated with allele replacement. The suicide vector also contains the mob sequence from an IncP plasmid to enable its mobilization and conjugation from strains possessing an integrated IncP conjugative plasmid. pMEG-375 also possesses the origin of replication from the plasmid R6K which is dependent on a gene pir and which is introduced into the chromosome of a suicide vector donor strain such as MGN-617 (Table 1) in a bacteriophage λ prophage. When the $\Delta asdA19::TTaraCP_{BAD}c^2TT$ is inserted into pMEG-375, the suicide victor pMEG-611 (FIG. 4) is the result. pMEG-611 can be introduced either by transformation or electroporation into the suicide vector conjugational donor strain MGN-617 (Table 1). MGN-617 also possesses a $\Delta asd$ mutation causing an obligate requirement for DAP. Thus MGN-617, containing a suicide vector such as pMEG-611 (FIG. 4), can be mated with a suitable *S. typhimurium* recipient strain such as λ3761 in the presence of DAP and exconjugants inheriting the pMEG-611 suicide vector by a single reciprocal crossover between homologous sequences flanking the asd gene on the plasmid vector and those on the chromosome lead to ampicillin and chloramphenicol resistant survivors. (DAP is not included in this selection medium so that the MGN-617 cells that are permissive for the suicide vector die by lysis.) These single crossover integrants can be purified by restreaking on medium that contains ampicillin or chloramphenical but lacks DAP. Small cultures can then be prepared of these drug resistant isolates and plated on medium containing 5% sucrose and DAP (so that cells inheriting the $\Delta asdA19::TTaraCP_{BAD}c2TT$ mutation survive). If the suicide plasmid still resides in the bacterial chromosome the cells will be killed, whereas if the second crossover event has occurred excising the suicide vector from the chromosome, bacteria will survive and form a colony. If the second crossover event occurs on the opposite side of the asd deletion mutation as was involved in the first crossover event, an allele replacement will occur so that the wild-type asd$^+$ allele in the chromosome is now replaced with a $\Delta asdA19::TTaraCP_{BAD}c2TT$ deletion/insertion mutation. By use of DNA probes and PCR with suitable oligonucleotides, proof of the stable existence of the construction in the chromosome can be verified including the absence of the wild-type asd$^+$ allele. The bacteria now have an obligate requirement for DAP.

Figure 5:
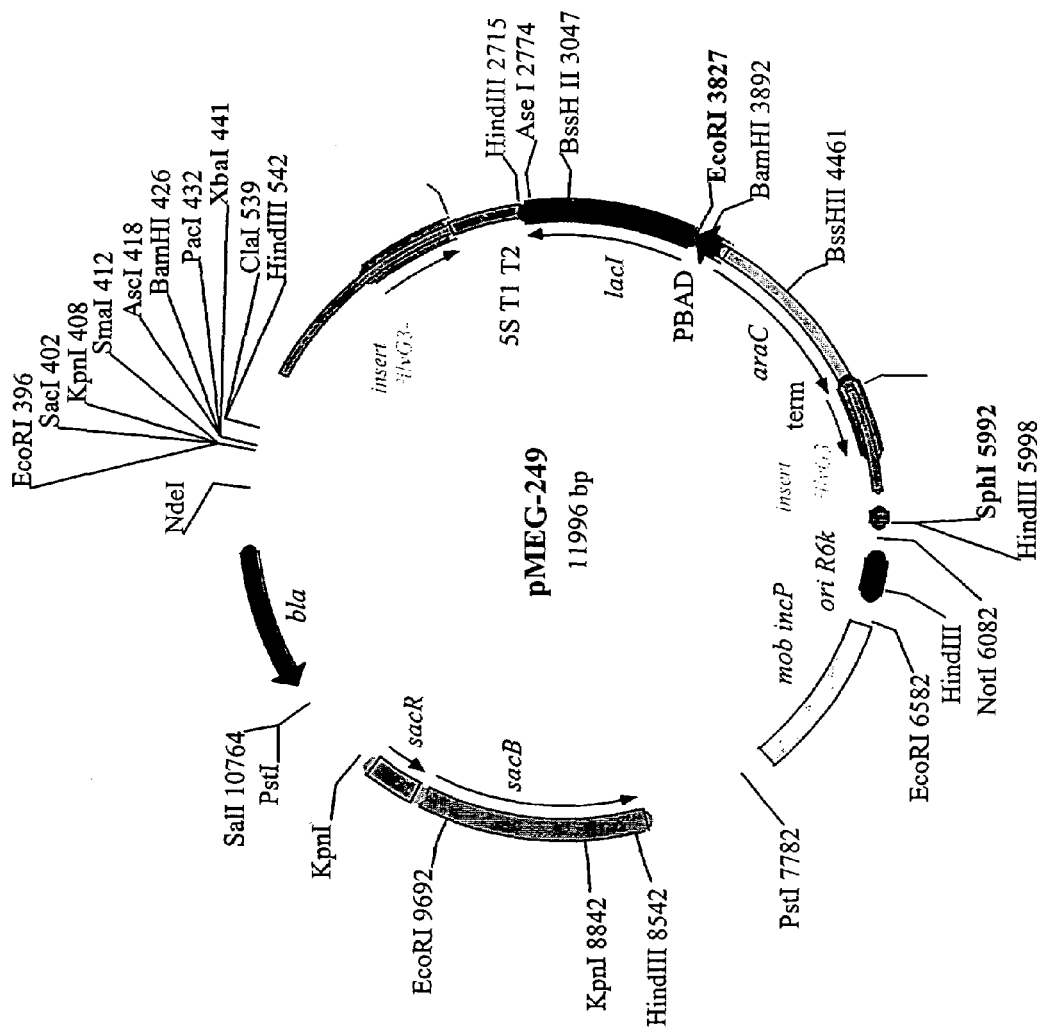
FIG. 5 depicts suicide vector pMEG-249 for delivery of $\Delta ilvG3::TTaraCP_{BAD}lacITT$.

A suicide vector to be used for allele replacement to introduce the ΔilvG3::TTaraCP$_{BAD}$lacITT deletion/insertion mutation is depicted as pMEG-249 (FIG. 5). The suicide vector portion of pMEG-249 is slightly different than that in pMEG-611 in that there is no gene for chloramphenicol resistance although other properties of the suicide vector construct are the same and it can be conjugated from the suicide vector donor strain MGN-617.

Figure 1:
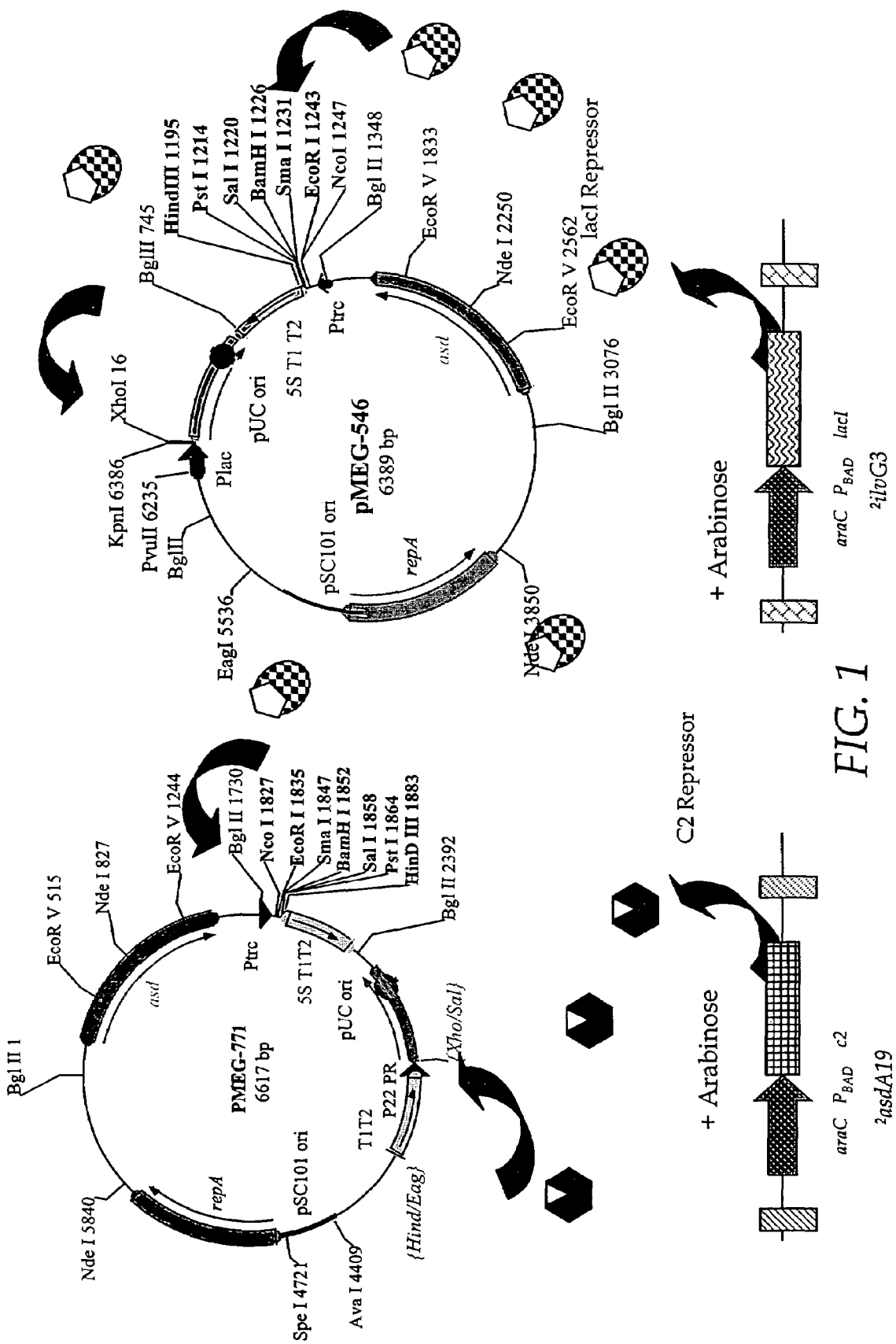
FIG. 1 depicts the RAVs pMEG-546 and pMEG-771 and the essential chromosomal deletion/insertion mutations needed for their maintenance.
Figure 6:
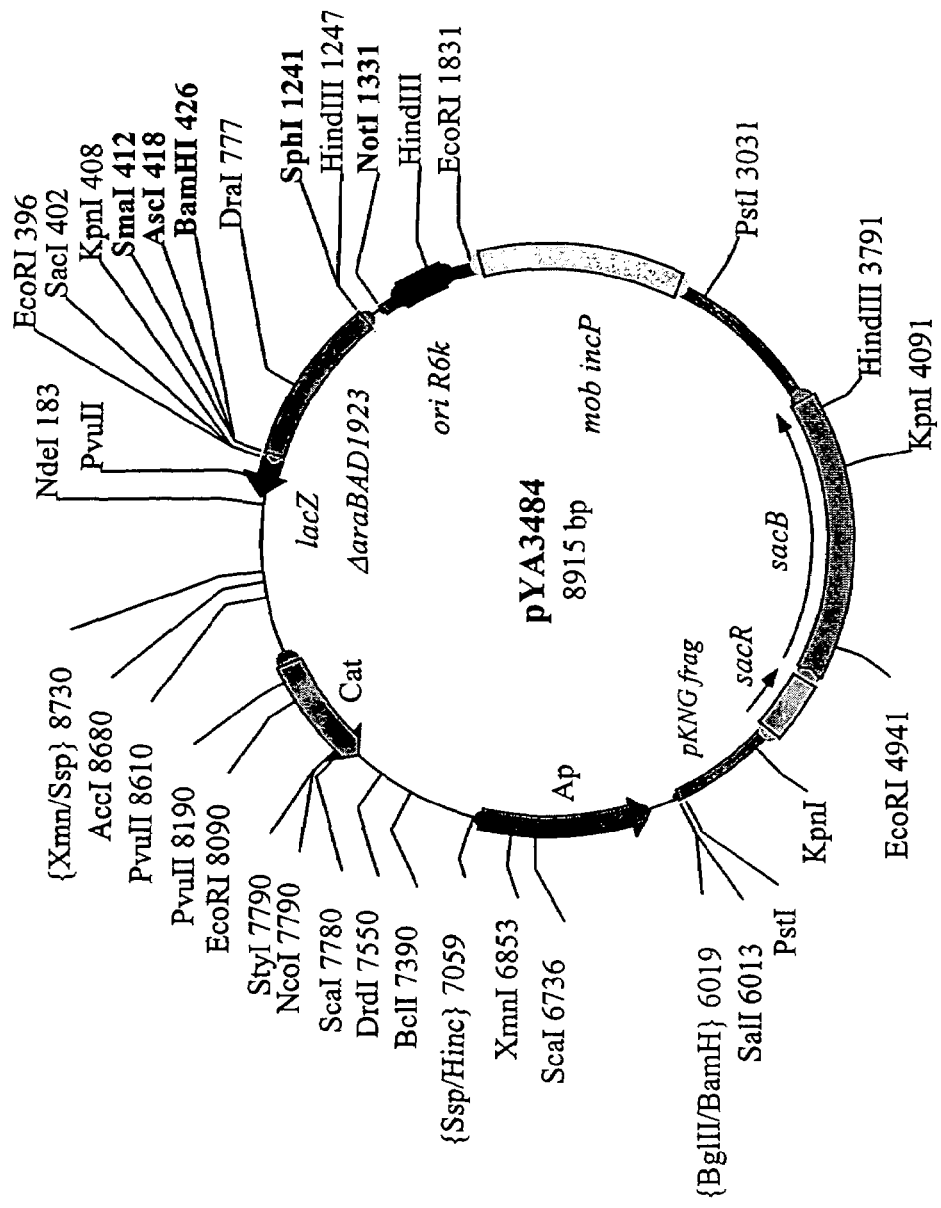
FIG. 6 depicts suicide vector pYA3484 for delivery of $\Delta araBAD1923$.

As previously stated, a RAV in a bacterial host with mutations 1 and 2 (FIG. 2), when moved from a medium with arabinose to a medium without arabinose initiates runaway replication quite rapidly and growth can cease within two generations. One way to decrease the rate of arabinose utilization is to include mutation 3, that is ΔaraBAD1923. This mutation eliminates the structural genes for the enzymes that break down arabinose, thus arabinose taken into the cell stays there until it leaks out or is decreased in concentration during each subsequent cell division. Thus, a bacterial strain with mutations 1, 2, and 3 (FIG. 2) will initiate runaway vector replication after a longer time in the absence of exogenous arabinose than is the case for a strain with only mutations 1 and 2 as shown in FIG. 1. FIG. 6 depicts the suicide vector pYA3484 for delivery of the ΔaraBAD1923 deletion mutation into the chromosome of the strain to be constructed. The procedures to achieve allele exchange are as described above in detail for the ΔasdA19::TTaraCP$_{BAD}$c2TT deletion/insertion mutation. However, plating in the presence of 5% sucrose is done on MacConkey-Ara plates containing 1% arabinose (plus DAP if the strain also possesses the ΔasdA19::TTaraCP$_{BAD}$c2TT mutation). Success in allele replacement is recognized by examining the plates after 16 h incubation at 37° C. to identify Ara⁻ non-fermenting isolates.

Figure 7:
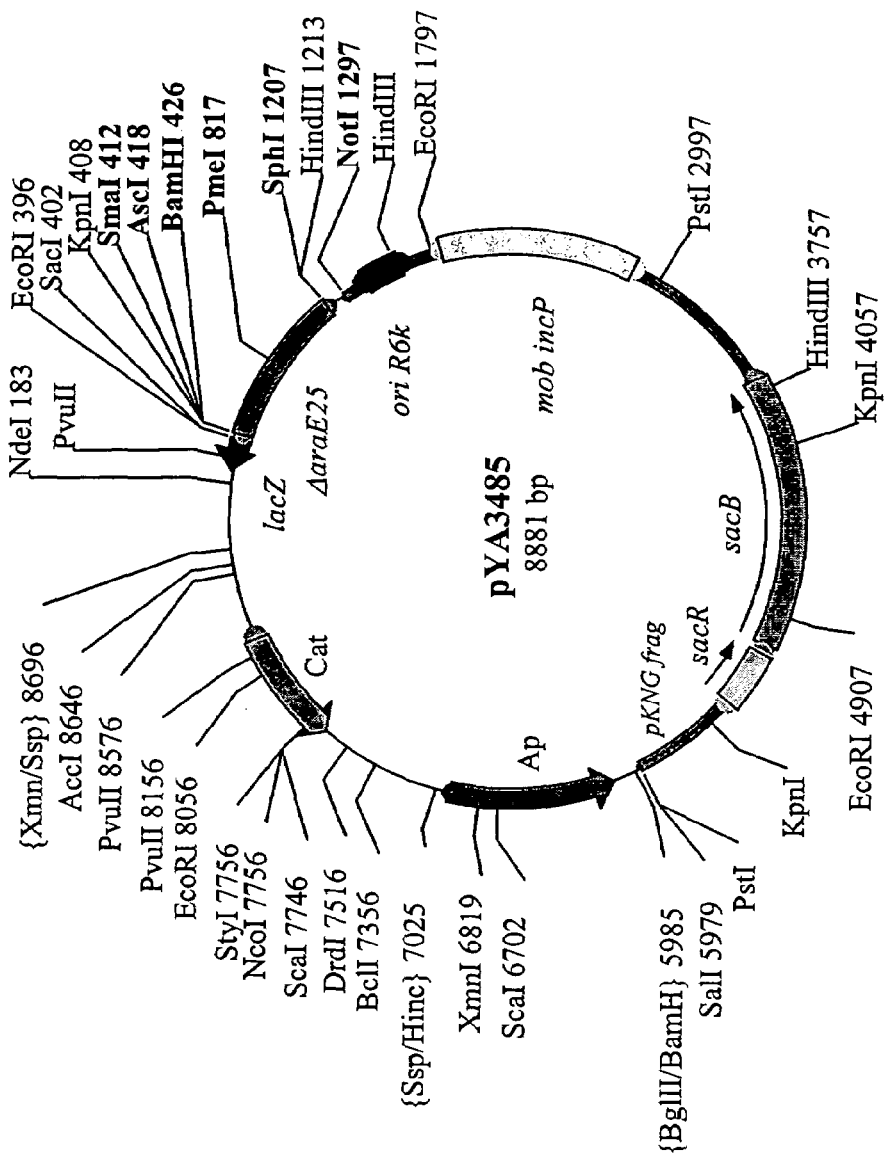
FIG. 7 depicts suicide vector pYA3485 for delivery of $\Delta araE25$.

As stated above, in a strain with mutation 3 precluding the metabolic breakdown of arabinose, it is possible that some of the arabinose taken up by the cell grown in the presence of arabinose might leak out. For this reason mutation 7, which is a ΔaraE25 mutation (FIG. 2), can be introduced into the strain making use of the suicide vector pYA3485 (FIG. 7). The araE gene encodes the low affinity transport protein for arabinose and in its absence, higher concentrations of arabinose are needed for expression of the araCP$_{BAD}$ regulatory signal, but once internalized, arabinose is very inefficiently leaked out of the bacterial cell (Schlief et al., pp. 1300-1309 in Neidhardt et al.). Thus in a bacterial strain with the ΔaraBAD1923 and ΔaraE25 mutations in addition to mutations 1 and 2 (FIG. 2), runaway replication of a RAV would be delayed even more in moving from a medium with to a medium without arabinose. In the construction of such a strain, it is necessary to introduce the ΔaraE25 mutation prior to the ΔaraBAD1923 mutation. This is because bacteria with the ΔaraE25 mutation can still ferment arabinose to result in a color change on MacConkey-Ara plates but do so slowly. It is important, for this reason, to examine the MacConkey-Ara plates (containing 5% sucrose, 1% arabinose and DAP, if necessary) after only 16 h incubation at 37° C. Longer incubation obscures the differences because cells with the ΔaraE25 allele will eventually metabolize enough arabinose to produce sufficient acid to give a color reaction indistinguishable from that given by colonies from cells with the wild-type araE allele. The recognition of success in introducing the ΔaraBAD1923 allele, into the strain containing the ΔaraE25 mutation, is straightforward since colonies examined after 40 h of incubation at 37° C., exhibit an Ara⁺ phenotype in the case of the ΔaraE25 parent, while the double mutant with ΔaraE25 and ΔaraBAD1923 mutations will be unable to ferment arabinose and will be Ara⁻ in phenotype.

Further modification of the strains for even more delay in the timing of RAV expression can be achieved by modifying mutation 3 (FIG. 2) in two steps. First, the ΔaraBAD1923 allele is modified to remove the sequence encoding several N-terminal amino acids of the araB gene and is replaced with an NcoI cloning site to enable insertion of other genes into this site to yield mutation ΔaraBAD1924. In this regard, it should be noted that the ΔaraBAD1924 mutation is a deletion of all parts of the arabinose operon other than the araCP$_{BAD}$ promoter. Thus the modified ΔaraBAD1924 allele (mutation 4, FIG. 2) is the equivalent of a native araCP$_{BAD}$ within the chromosome into which can be inserted various foreign genes using the NcoI site which encodes an ATG start codon. One such derivative, mutation 5 in FIG. 2, encodes the P22 c2 repressor gene. In another case, mutation 6 in FIG. 2, the insertion has both the c2 repressor gene and the lacI repressor to yield the ΔaraBAD1926 allele. In both of these cases the level of C2 or C2 and LacI repressor proteins should be double the concentration present in cells that only possess a single copy of the repressor gene as in mutations 1 and 2 (FIG. 2). These dual repressor genes will further delay the time of derepression of the C2 repressible pUC RNAII gene and the LacI repressible P$_{trc}$ controlled gene for the foreign antigen on the RAV.

Candidate vaccine strains must have mutations rendering them avirulent for the animal or human host and yet retain immugenicity. Mutations that are effective in attenuating *S. typhimurium* as well as other *Salmonella* serotypes, and mutations that engender them with high immunogenicity include mutations in the phoPQ operon (U.S. Pat. No. 5,424,065; Miller, et al., 1989), such as the ΔphoP1918 and ΔphoP24 mutations (mutations 8 and 9 in FIG. 2). A suicide vector for allele replacement to introduce the ΔphoP1918 allele is depicted in FIG. 8 as pMEG-550 and the suicide vector pMEG-368 for allele replacement to introduce the ΔphoP24 mutation is depicted in FIG. 9. Success in introducing either of these phoP mutations is achieved by screening for the phoN gene encoded non-specific acid phosphatase which is not synthesized in phoP mutants (Kier et al., 1979). This is achieved by using a soft agar overlay assay with the chromogenic phosphatase substrate α-naphthyl phosphate (Kier et al., 1999 J. Bacteriol. 138:155-161). Definitive proof for presence of the mutant alleles is accomplished using PCR to reveal the size of the deletions, DNA probe hybridization to show the absence of phoP sequences, and screening for phenotypes associated with ΔphoP mutations. These phenotypes include: the inability to synthesize non-specific acid phosphatase (Kier et al., 1979); polymyxin-B sensitivity; and susceptibility to killing by macrophages (Fields et al., 1989).

Example 2

Construction of RAVs for Use in RADS.

The RAV pMEG-771 (FIG. 10) is obtained by removing the EagI-XhoI fragment of pMEG-546 (FIG. 10) containing the lac promoter and replacing it with P22 P$_R$ from pMEG-104 FIG. 10 and FIG. 4 of U.S. patent application Ser. No. 08/761,769). pMEG-546 is digested with EagI and treated with T4 DNA polymerase to blunt the end, then digested with XhoI. This removes P$_{tac}$. PMEG-104 is then digested with HindIII then blunt ended with T4 DNA polymerase and digested with SalI. This fragment of pMEG-104 contains the

Figure 10:
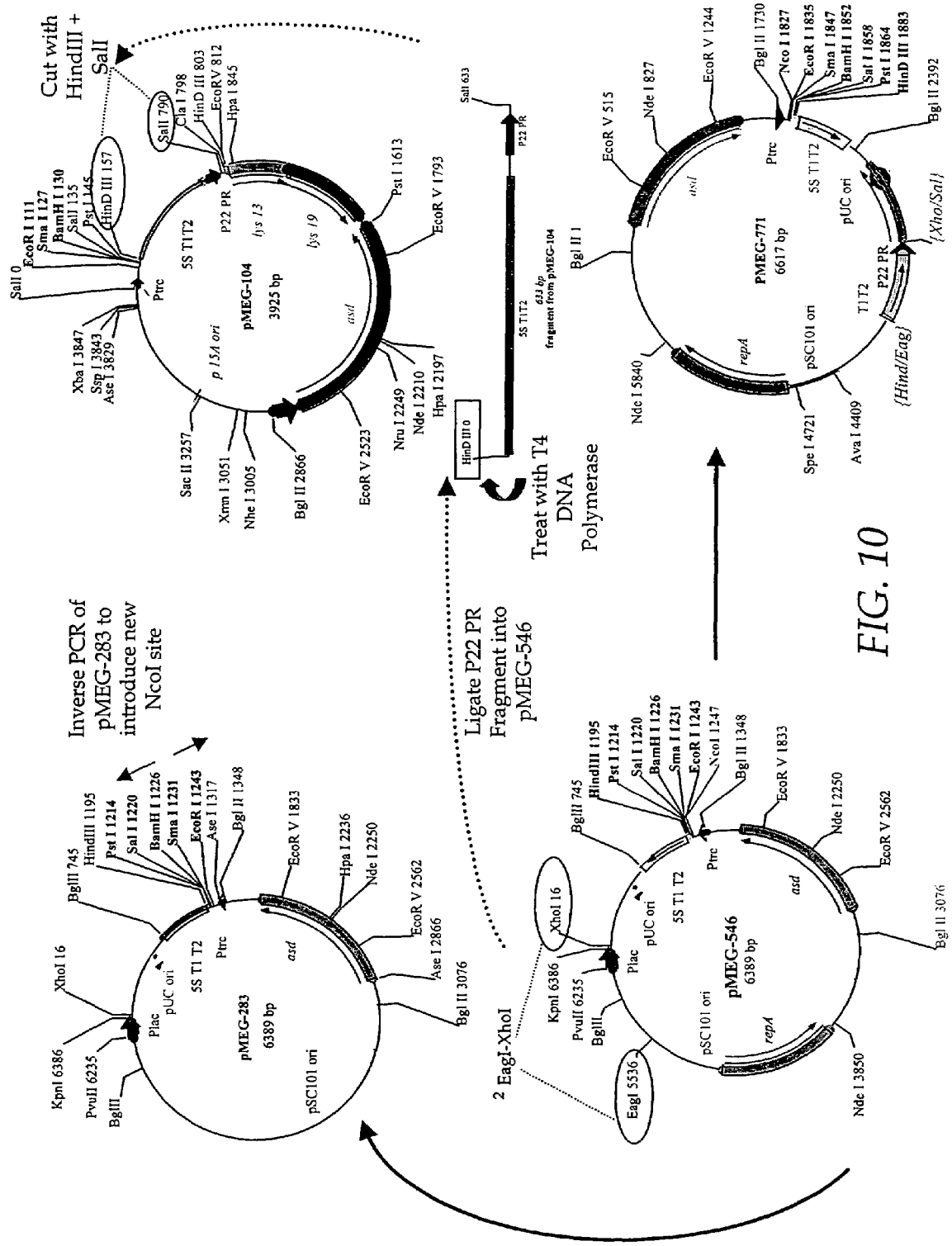
FIG. 10 depicts the generation of RAVs pMEG-546 from pMEG-283, and pMEG-771 from pMEG-546 and pMEG-104.

5S T1 T2 transcription terminator and the P22 $P_R$, which is blunt end ligated into the cut pMEG-546 to yield pMEG-771 (FIG. 10). pMEG-771 can be used with host strains containing mutations 1 and 2 (FIG. 2) plus other mutations such as 3 or 5 or 6, optionally with mutations as described in Example 1, to provide arabinose regulated runaway expression. Another RAV, pMEG-546, as depicted in FIG. 1, has all the regulatory signals repressible by the lacI gene product encoded within the ilvG³::TTaraCP$_{BAD}$lacITT deletion/insertion mutation 2 (FIG. 2). In this case, the pUC RNAIIA transcript is under the control of the lac promoter ($P_{lac}$), which in the absence of LacI is transcriptionally active, leading to the pUC mode of unregulated replication. In addition, (the site for insertion of foreign genes in pMEG-546 is adjacent to and downstream from $P_{trc}$ which is a hybrid trp-lac promoter that is very efficient at transcription initiation and also repressible by the LacI repressor protein) (Brossius, J. et al. (1984) Gene 27:161-172). pMEG-546, like pMEG-771, has the pSC101 origin of replication and thus when the RAV host strain is grown in medium with arabinose present there are only five to six copies of pMEG-546 per chromosome DNA equivalent and the strain grows very well because of this low copy number and the low expression of any gene for a foreign antigen (cloned into the multiple cloning site downstream from $P_{trc}$.)

Figure 11:
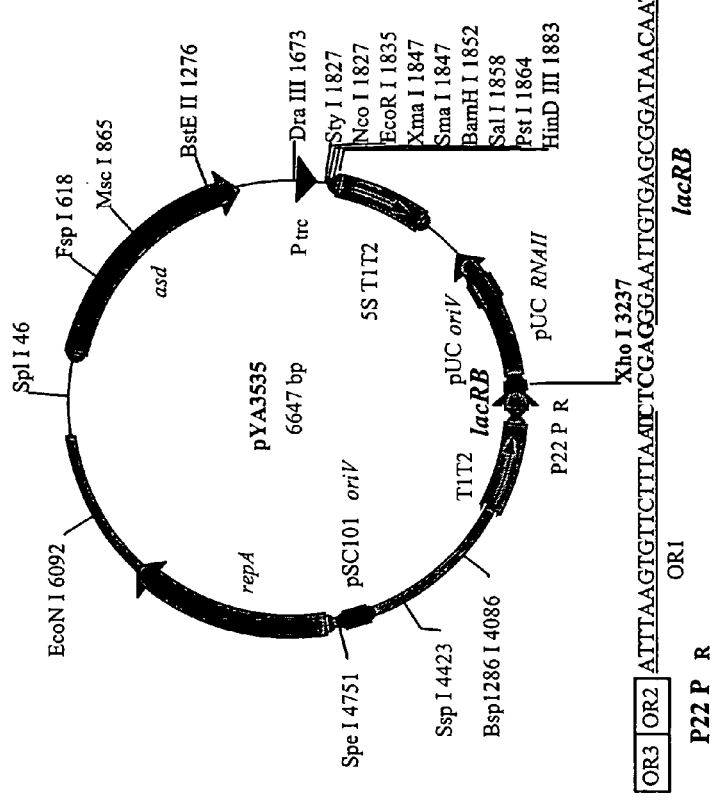
FIG. 11 depicts the modification of pMEG-771 to include a lacRB (LacI repressor binding) site after P22 $P_R$ but before pUC RNAII to yield pYA3535.

Another way to delay the time of onset of runaway vector replication expression upon introduction of the vaccine strain into an immunized animal is to enhance the repressive ability of repressors. This increased repression will then delay the time before transcription from P22 $P_R$ in pMEG-771 (FIG. 1) initiates to make the pUC RNAII transcript. One way to achieve this is by insertion of a LacI repressor binding site (lacRB) as part of the P22 $P_R$ so that both the P22 C2 repressor and LacI repressor block transcription leading to the synthesis of the pUC RNAII transcript. Such a construct as a modification of pMEG-771 is depicted in FIG. 11.

Figure 8:
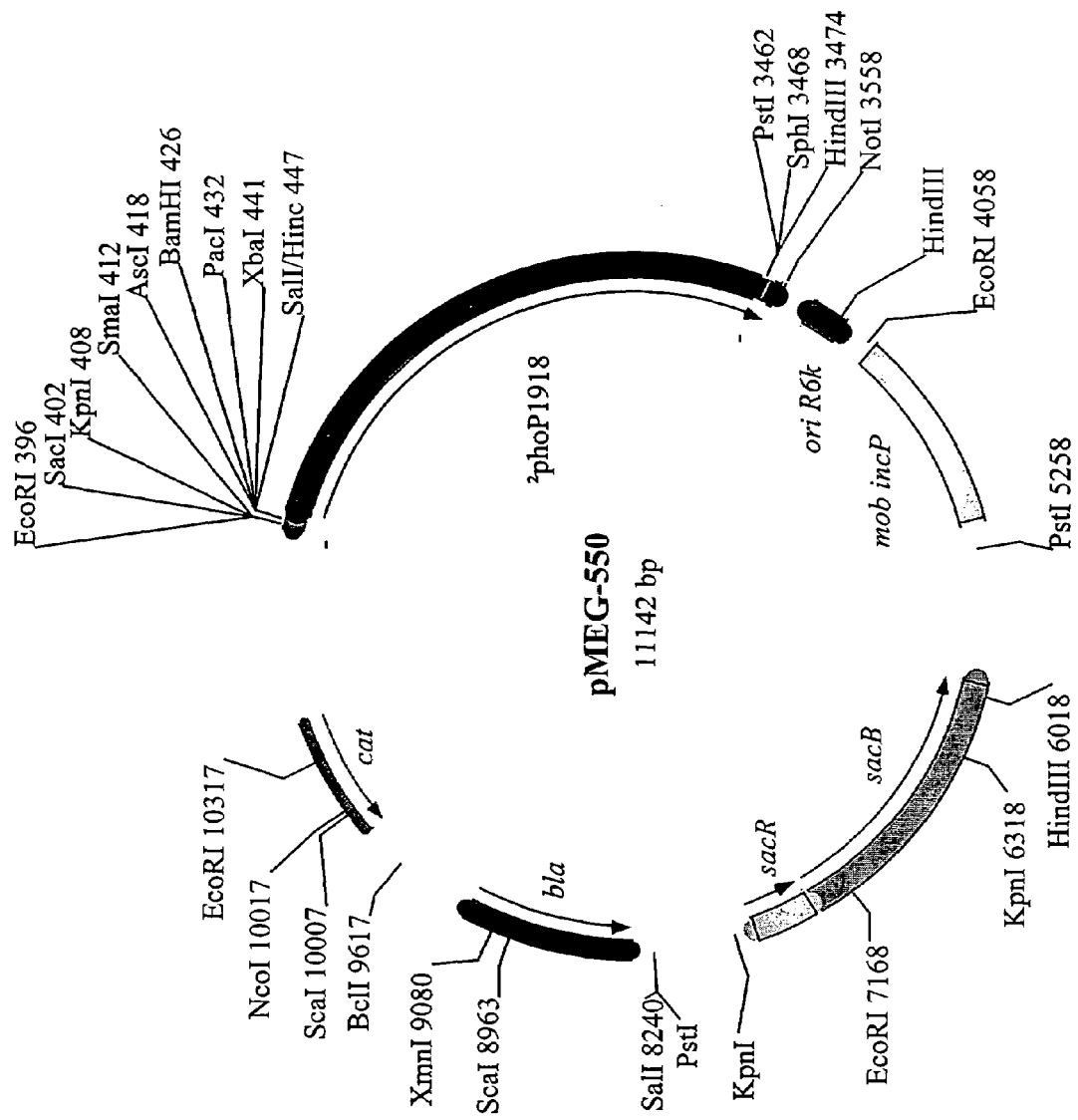
FIG. 8 depicts suicide vector pMEG-550 for delivery of $\Delta phoP1918$.
Figure 9:
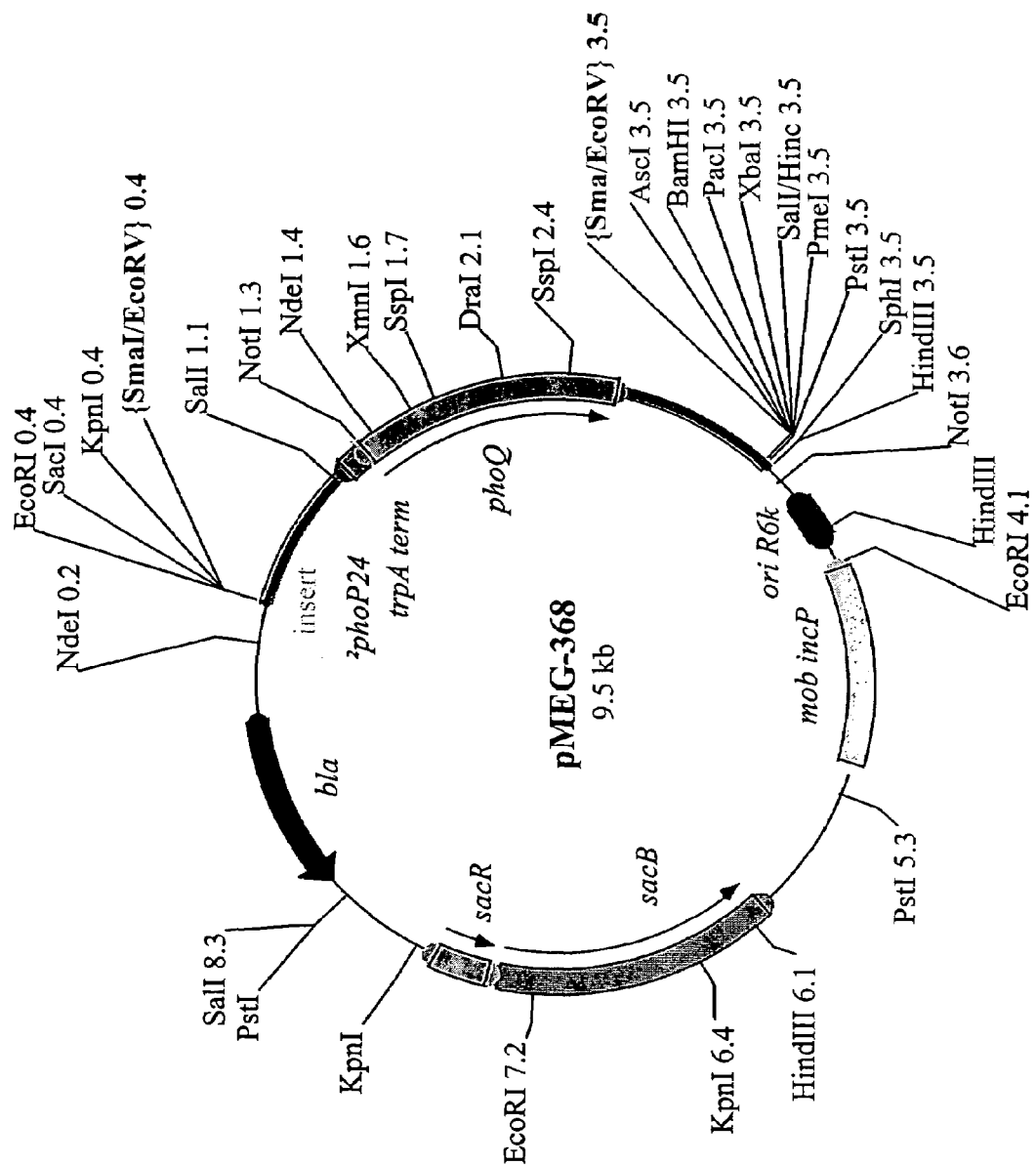
FIG. 9 depicts suicide vector pMEG-368 for delivery of $\Delta phoP24$.
Figure 12:
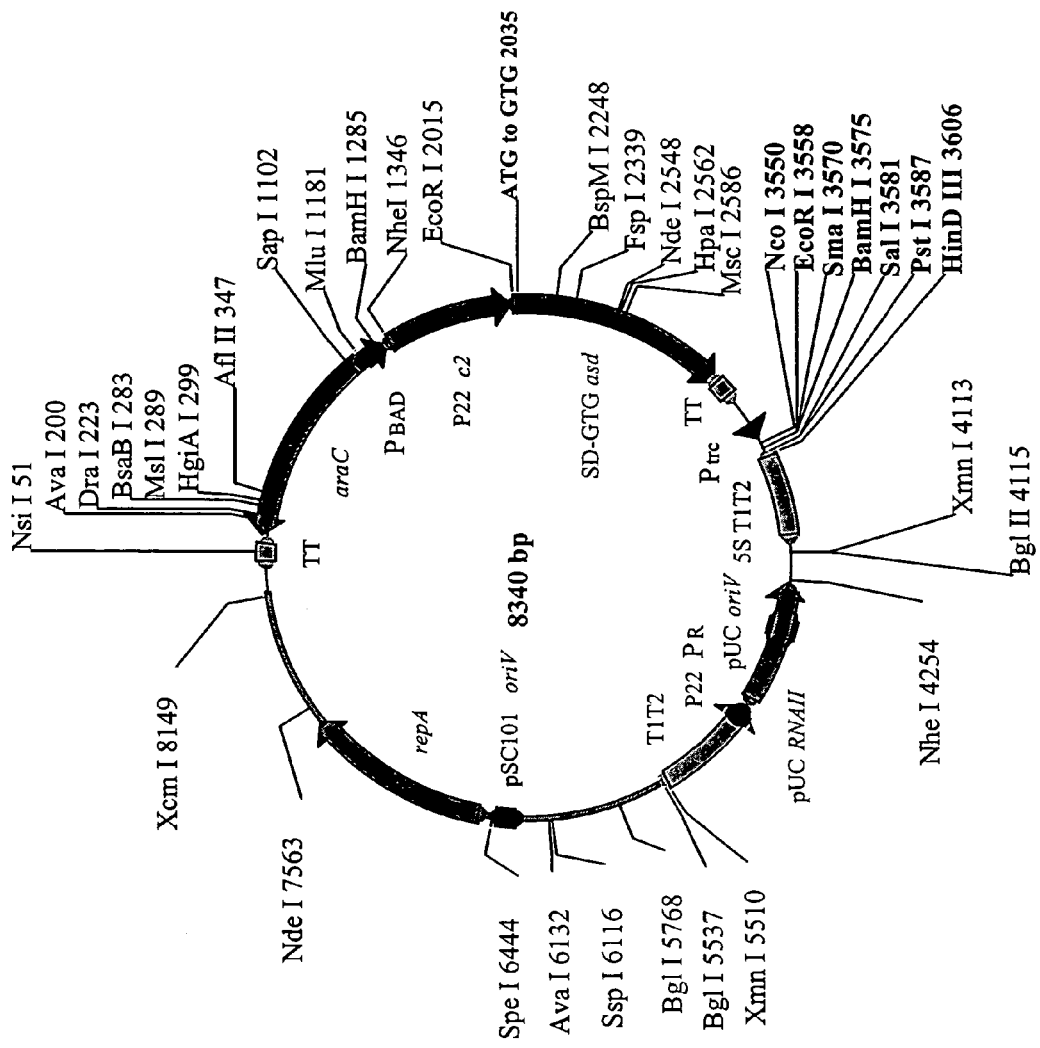
FIG. 12 depicts the RAV pMEG-771 derivative with $TTaraCP_{BAD}c2GTGasd$ in place of asd.

In FIG. 8 of WO96/40947 a runaway lysis containment vector is depicted that has the attributes of pMEG-546 (FIG. 10) but also contains the P22 phage lysis genes lys-13 and lys-19 under the control of P22 $P_R$ so that by shifting from medium with arabinose to medium without arabinose the cessation in P22 c2 gene expression leads to a reduction in C2 repressor and transcription of the phage lysis genes on the RAV to ultimately cause lysis and death of the bacteria. Observations to date with the expression of high copy number plasmids with phage lysis genes, even under stringent repression, demonstrates that some leak through transcription occurs to result in death by lysis of some cells in the population. We have therefore resorted to a delayed onset lysis by cessation of synthesis of the essential gene asd needed for the synthesis of DAP, an essential constituent of the rigid layer of the bacterial cell wall. This was accomplished by generating a TTaraCP$_{BAD}$c2GTG asd sequence in which the start codon for the asd gene has been changed from ATG to GTG to reduce the efficiency of translation of the asd mRNA and therefore the level of Asd enzyme synthesized. This modified version of pMEG-771 is depicted in FIG. 12. Specifically, the 2.5 kb BglII-NdeI TT araCP$_{BAD}$C² GTG asd DNA fragment from pYA3531 (FIG. 21) is subcloned into pMEG-771 (FIG. 1) partially digested with BglII at position 1 and NdeI at position 827. Then, a synthesized transcriptional terminator is inserted at the BglII site located before the $P_{trc}$ promoter to yield the plasmid depicted in FIG. 12. We have the same construct without the c2 gene, but the presence of the c2 gene in proximity to the P22 $P_R$ on the RAV enhances the efficiency of repression of transcription initiated at $P_R$. In this regard, recall that in bacteriophages such as λ and P22 the repressor gene and the promoters to which the repressor binds are adjacent, thus enhancing the efficiency of repression. This is undoubtedly due to the fact that proteins are synthesized on polyribosomes in which the mRNA is still attached to the DNA template in proximity to the site of action of the repressor gene products. At such time as arabinose becomes exhausted and transcription from the araCP$_{BAD}$ promoter on the RAV ceases, asd mRNA ceases to be synthesized and because of the inefficiency of its translation due to the GUG start codon (encoded as GTG in the DNA sequence), Asd enzyme becomes limiting and after a few generations cells begin to undergo DAP-less death. The extent to which this will be achieved when plasmid copy number goes from the pSC101 level to the unregulated level in excess of several hundred copies of plasmid DNA per chromosome DNA equivalent after induction of the RAV expression is yet to be evaluated. An additional modification to further reduce the efficiency of translation of the asd gene mRNA is to change the Shine-Dalgarno sequence from AGGA to AAGA or AGAA.

Example 3

Construction and Evaluation of RADSs to Prevent *Erysipelothrix rhusiopathiae* Infection and Disease.

*Erysipelothrix rhusiopathiae* is a gram-positive pathogen of swine and turkeys that causes the disease erysipelas and in later life can cause arthritis (Wood, R. L. (1984) J. Am. Vet. Med. Assoc. 184:944-949). Previous work has identified a 65 kDa surface antigen termed Ery65 or SpaA.1 (Shimoji, Y. et al. 1999 Infect. Immun. 67:1646-1651) that can be injected into animals with adjuvant to confer protective immunity to *E. rhusiopathiae* challenge. There also exists a monoclonal antibody (Mab) to the Ery65 protein which can confer passive protection to animals infused with the Mab against challenge with viable *E. rhusiopathiae* (Henderson, L. et al. 1997. U.S. Pat. No. 5,625,038).

Figure 13:
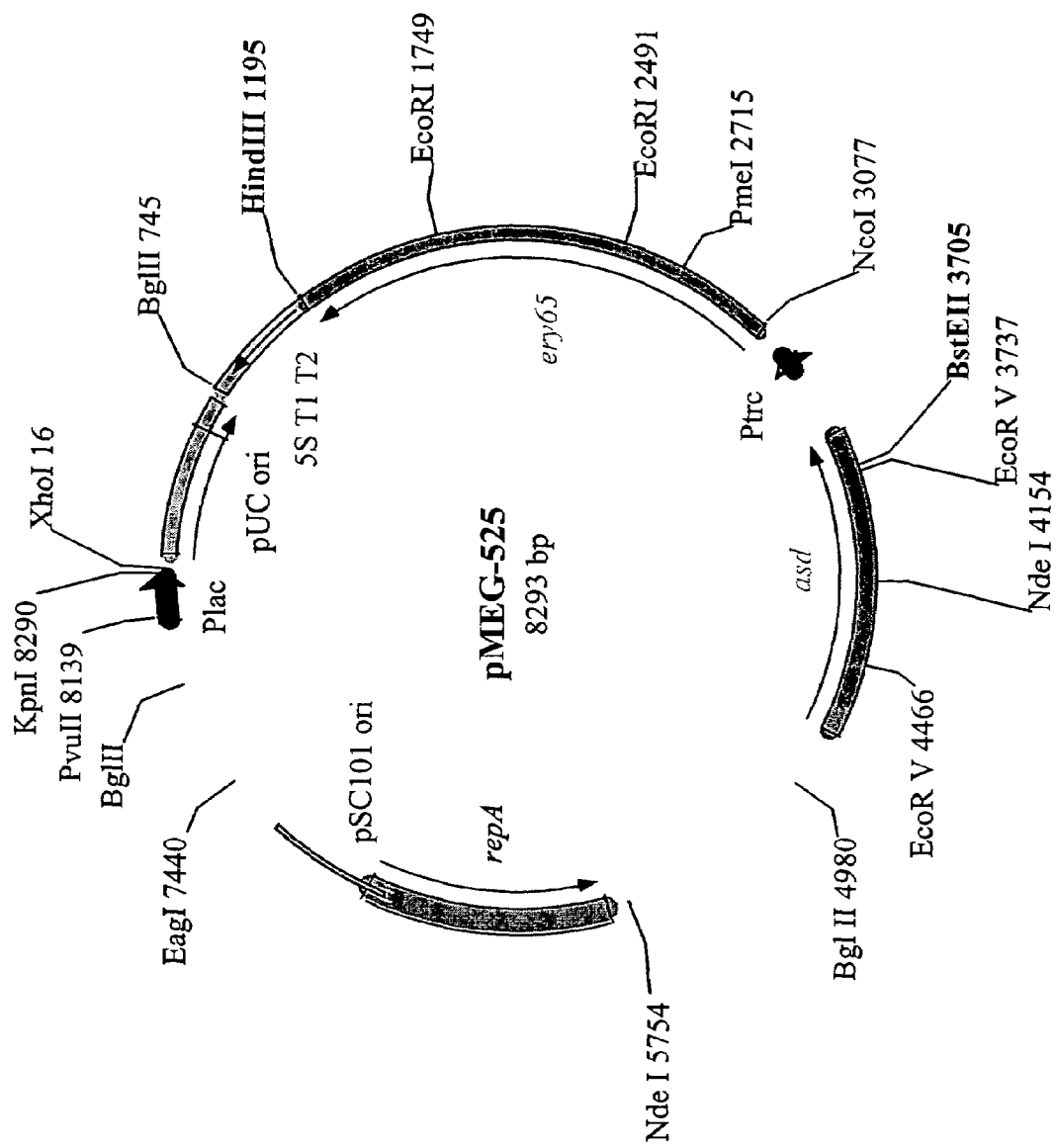
FIG. 13 depicts the RAV pMEG-525 specifying the Ery65 antigen.
Figure 14:
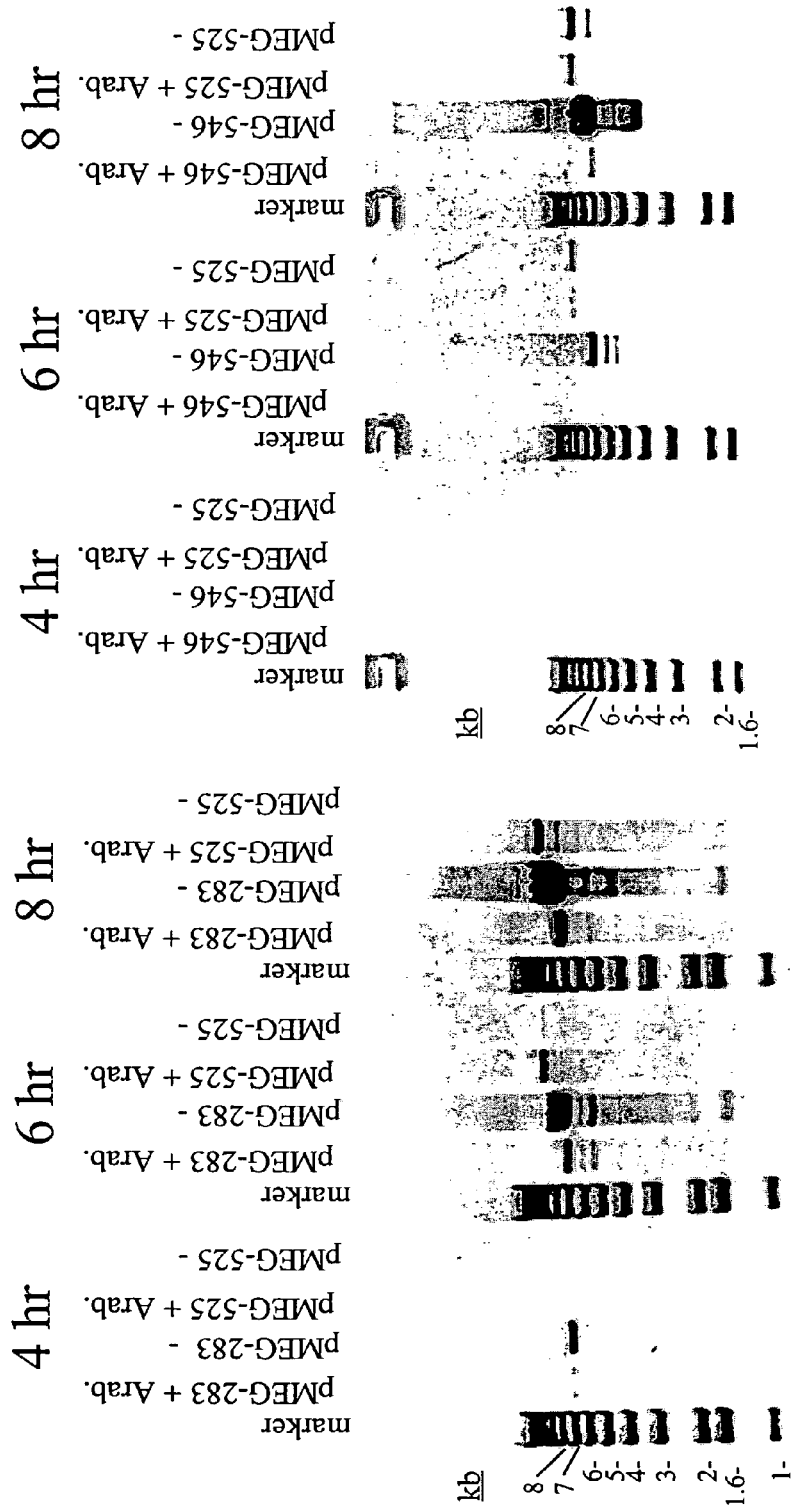
FIG. 14 shows the results of experiments demonstrating the increase in copy number for RAVs encoding Ery65. Plasmid DNA is shown for S. typhimurium MGN-966 (pMEG-283) vector and MGN-966(pMEG-525)+Ery65 or S. choleraesuis MGN-2267 (pMEG-546) vector and MGN-2267(pMEG-525)+Ery65 grown in Luria Broth in the presence or absence of arabinose following a dilution of 1 to 1,000.
Figure 15:
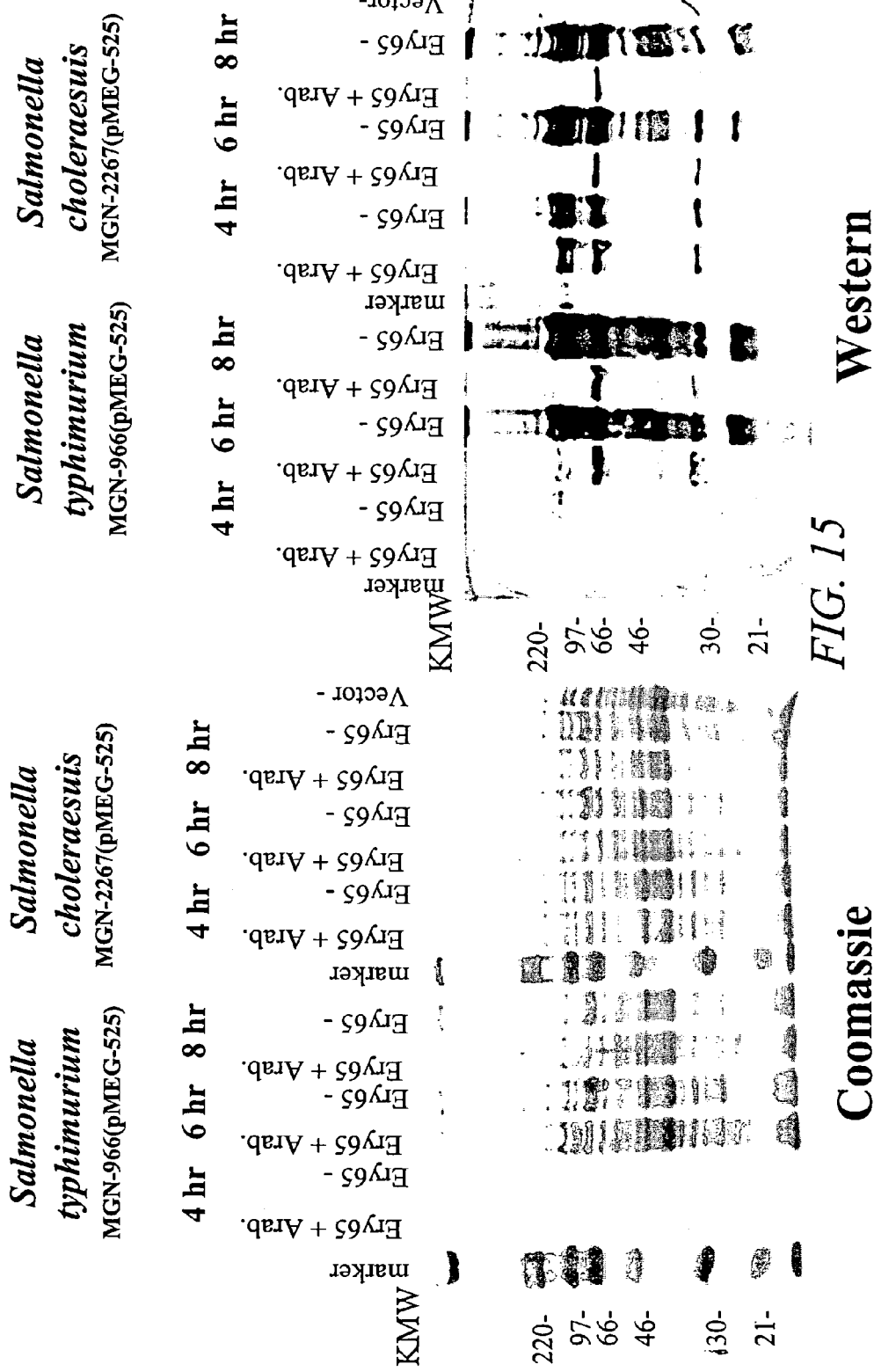
FIG. 15 shows the results of the same experiment as in FIG. 14, but here demonstrating the increase in Ery65 protein dependent upon growth of S. typhimurium MGN-966 (pMEG-525) and S. choleraesuis MGN-2267(pMEG-525) grown in Luria Broth in the presence or absence of arabinose following a dilution of 1 to 1,000.
Figure 16:
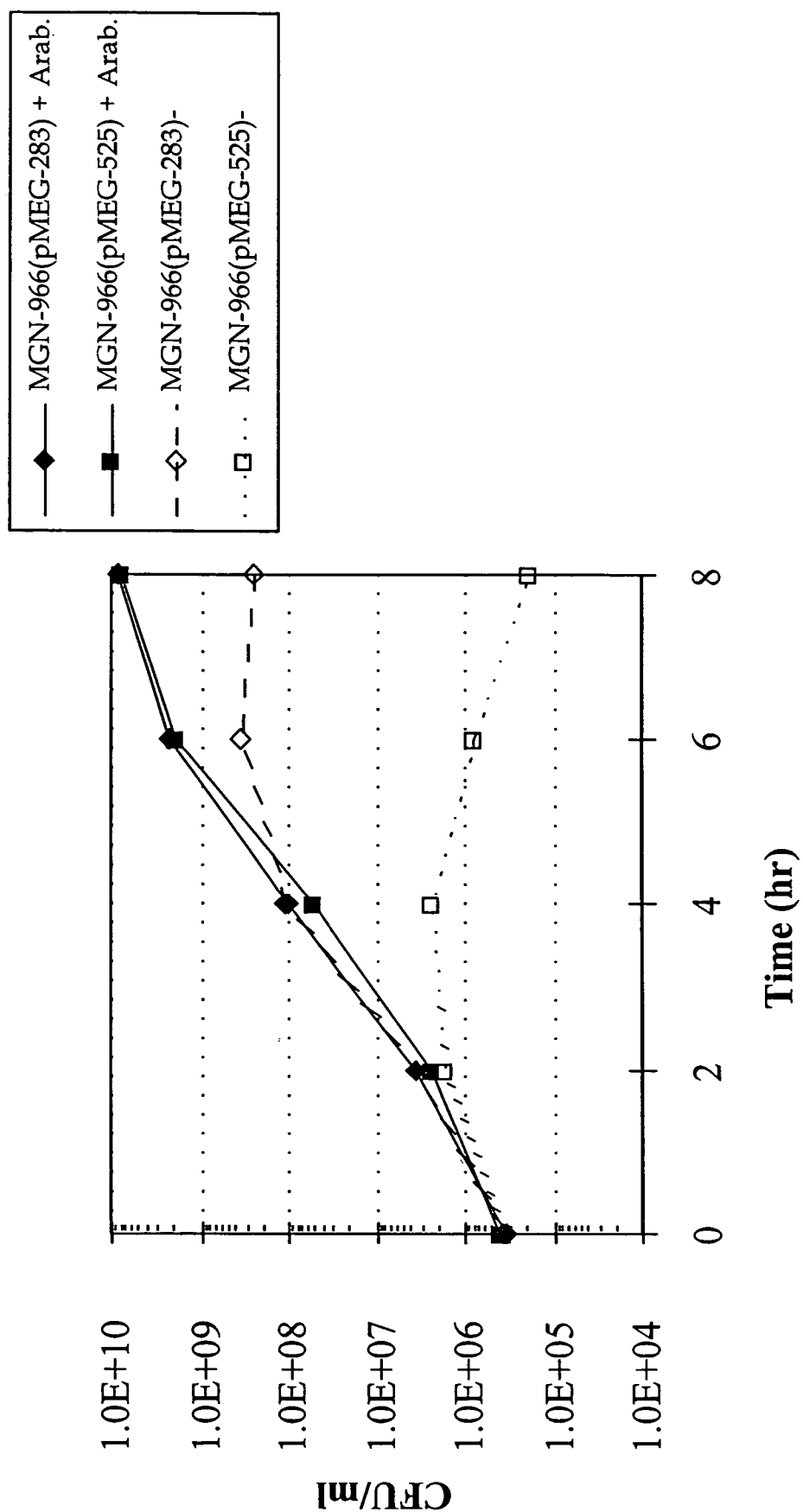
FIG. 16 shows the growth of S. typhimurium strains MGN-966(pMEG-525) expressing Ery65 and MGN-966 (pMEG-283) vector control grown in Luria Broth in the presence or absence of arabinose following a dilution of 1 to 1,000.
Figure 17:
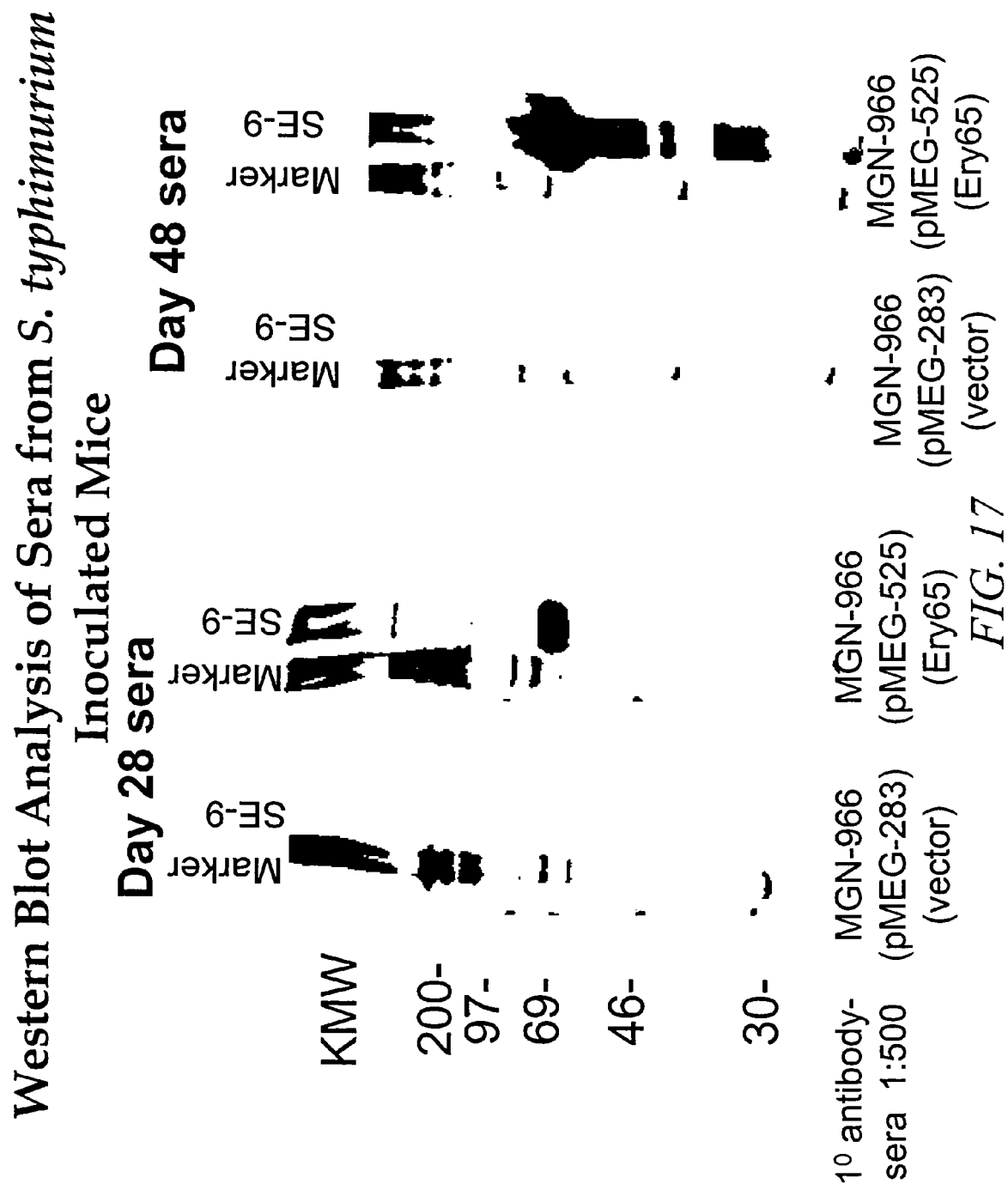
FIG. 17 depicts western blot analyses of sera from mice immunized with the vector control MGN-966(pMEG-283) and with MGN-966(pMEG-525) expressing the Ery65 antigen.
Figure 18:
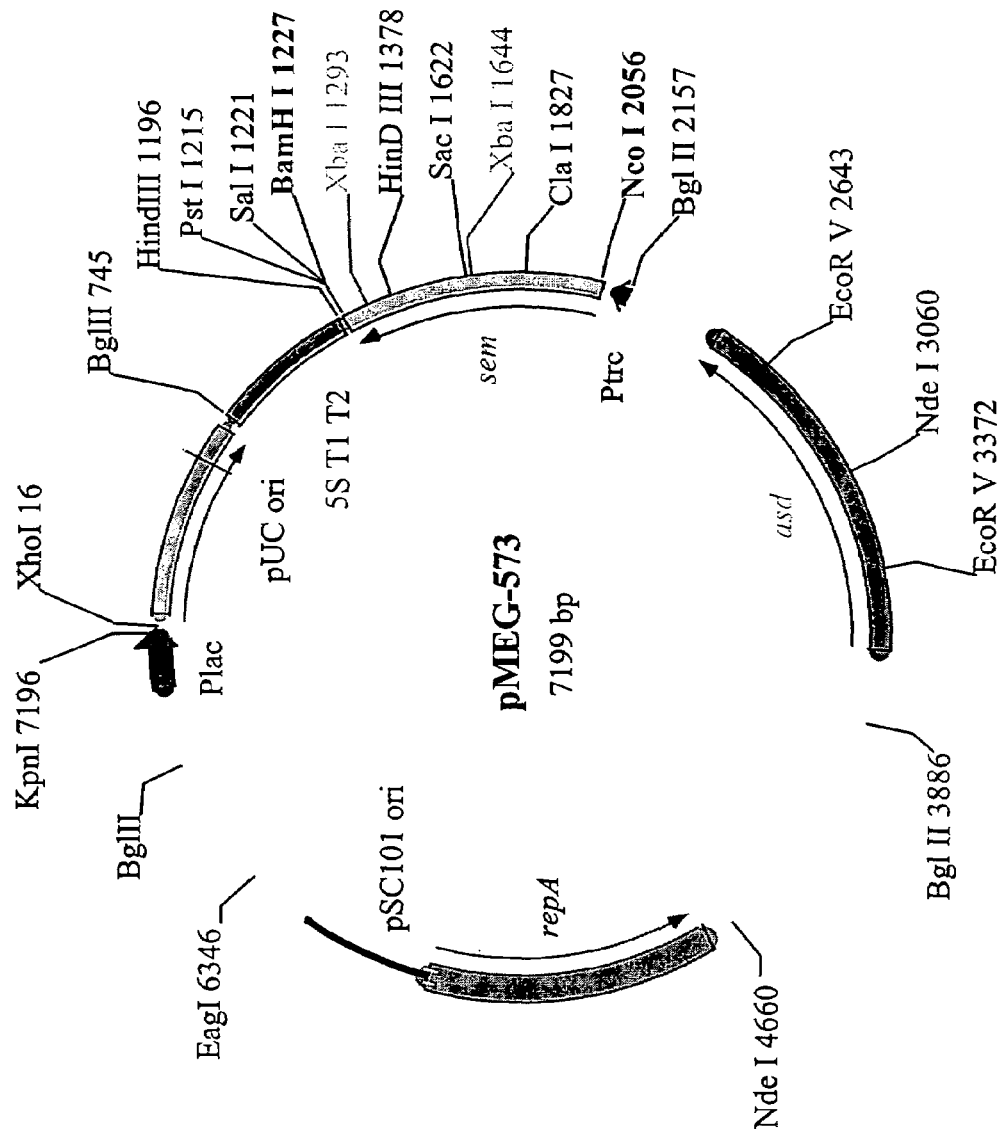
FIG. 18 depicts RAV pMEG-573 specifying the Streptococcus equi M protein (SeM).

The expression of the full length ery65 gene in *E. coli* and *S. typhimurium* tends to be quite toxic, possibly because of the signal sequence that doesn't function as well in gram-negative bacteria as it does in the natural gram-positive bacterial host, but more likely because of the highly hydrophobic C-terminal domain, which tends to have an affinity for the cytoplasmic membrane in *E. coli* and *Salmonella*, thereby impairing electron transport and metabolic good health. One solution to this problem is to express the Ery65 antigen on a RAV so that expression is delayed until the vaccine strain persists-in an environment lacking arabinose until the arabinose is exhausted, leading to the decrease of repressors to allow for the runaway replication from the pUC origin and high-level expression of the cloned gene insert. pMEG-525 (FIG. 13) is a RAV containing the Ery65 coding region, as shown in FIG. 14 including that for the signal sequence, cloned as a 2.5 kb BstEII-HindIII fragment from pMEG-446, (a pYA3332 vector containing the 1881 bp NcoI-HindIII PCR fragment encoding erg65 from *E. rhusiopathiae* E1-6P) into BstEII-HindIII digested runaway vector pMEG-283. When pMEG-525 is placed in either *S. typhimurium* or *S. choleraesuis* there is a time-dependent increase in plasmid copy number as a function of time after movement from a medium with arabinose to a medium without arabinose. It is also clear that there is a substantially increased amount of plasmid DNA with either vector only control RAV pMEG-283 in *S. typhimurium* MGN-966 or pMEG-546 in *S. choleraesuis* MGN-2267, compared to that for the RAV pMEG-525 which encodes the Ery65 antigen (FIG. 14) in either MGN-996 or MGN-2267. Thus, toxicity of Ery65 is still observed to some extent during induction. In spite of this, there are very substantial increases in the synthesis of Ery65 protein in both S. typhimurium and S. choleraesuis as a function of time after moving cultures from medium with arabinose to medium without arabinose (FIG. 15). As revealed in FIG. 16, S. typhimurium strain MGN-966(pMEG-525) with the RAV specifying the Ery65 antigen grows equally well as the isogenic strain MGN-966 (pMEG-283) containing the control RAV not encoding a foreign antigen, provided that arabinose is present. However, after diluting 1 to 1,000 non-aerated cultures grown for 12-16 hours in Luria Bertani broth containing 0.2% arabinose into Luria Bertani broth without arabinose, the expression of the Ery65 antigen sharply diminishes the rate of growth ultimately followed by death and inability to propagate viable bacteria (FIG. 16).

The above-described strains were grown in Luria Bertani broth containing 0.2% arabinose to an $OD_{600}$ of 1.0 and administered intranasally to Rompun and Ketaset sedated BALB/c mice weighing ~20 gm. Mice immunized with ~$10^5$ CFU of the S. typhimurium vaccine strain MGN-966 (pMEG-525) on days 0 and 31, exhibit strong immune responses following a single immunization on day 28, as detected by Western blot with sera from immunized mice, to a protein of about 65 kDa in size in an extract of the SE-9 strain of E. rhusiopathiae* (FIG. 17). This antibody response is even more substantial following the day 31 booster immunization as seen on day 48 after immunization (FIG. 17). Challenge of these immunized mice with a sub cutaneous lethal dose of 118 CFU of *E. rhusiopathiae* strain E1-6P revealed 100% protection, relative to the vector only control mice, as shown in Table 3. This was in contrast to previous studies conducted using the entire Ery65 antigen on other expression vectors in *Salmonella* which were unable to provide either a detectable immune response to Ery65 or protection against a lethal challenge of *E. rhusiopathiae*.

TABLE 3

Survival of BALB/c Mice Immunized with RAV *S. typhimurium* Expressing Entire Ery65 after S.C. Challenge with *E. rhusiopathiae* E1-6P

| Strain[1] | Immunizing Dose (CFU) day 0, day 31 | Survivors/Total[2] After Challenge |
|---|---|---|
| Control | — | 0/3 |
| MGN-966 (pMEG-283) | $1.1 \times 10^6$, $1.8 \times 10^6$ | 0/10 |
| MGN-966 (pMEG-525) | $2.0 \times 10^4$, $6.4 \times 10^5$ | 10/10 |

[1]Genotype: ΔphoP22ΔasdA19($P_{BAD}$c2) ΔilvG3($P_{BAD}$.lacI)
[2]after challenge on day 52 with 118 CFU of E1-6P Example 4

Construction of RADSs to Prevent *Streptococcus equi* Infection and Disease

*Streptococcus equi* causes a very severe disease of racehorses and other equines called strangles (Nara, P. et al. (1983) Am. J. Vet. Res. 44:529-534). Even worse is the immune complex disease *Purpura hemorrhagica*, a consequence of earlier in life *S. equi* infection (Galan, J. and J. Timoney (1985) J. Immunology 135:3134-3137). *S. equi*, like group A *streptococci*, produce an M protein on the surface with is antiphagocytic and thus a major virulence determinant enhancing the success of *S. equi* infection.

Antibodies to the *S. equi* M protein (SeM) are opsonic and facilitate the successful phagocytosis and killing of *S. equi* (Galan, J. and J. Timoney (1985) Infect. Immun. 47:623-628). Thus an antibody response to SeM is likely to be highly protective in preventing *S. equi* infection of horses. The RAV pMEG-573 encoding the *S. equi* SeM protein is depicted in FIG. 18. This RAV was obtained by cloning the PCR fragment flanked by primers SeM444-474 GCGAACTCTGAGGTTAGTCGTACGGCGACTC (SEQ ID NO: 1) and SeM1265-1233 TTGATCAATTTCT-GCTAATTTTTGAGCCATTTC (SEQ ID NO: 2), containing the central portion of the SeM coding region from the SeM clone pSEM06, into the Ned and BamHI sites of pMEG-546. pMEG-573 is only dependent on the presence of the ΔilvG3::TTaraC$P_{BAD}$lacITT deletion/insertion mutation (FIG. 2) in the chromosome to repress the runaway phenotype and SeM expression. The vaccine strains for SeM also contain either the ΔphoP1918 or ΔphoP24 attenuating deletion mutation (mutations 8 and 9, FIG. 2). A comparison of the level of SeM expression by different attenuated *Salmonella* vaccine strains, in which SeM expression on the plasmid vector was under the transcriptional control of either P22$P_R$, $P_{trc}$ or λ$P_L$ on pBR based plasmids, or under the control of $P_{trc}$ on the RAV, pMEG-573, is shown in FIG. 19. Strains for this comparison were grown in Luria Bertani broth for 6 hours either with or without 0.2% arabinose following a 1/1,000 dilution from non-aerated *Luria Bertani* broth cultures with 0.2% arabinose. One milliliter of cells was then pelleted and total proteins were run on SDS PAGE for analysis by staining with Coomassie blue or transfer to nitrocellulose for western blot analysis with SeM specific antibody as shown in FIG. 19. It is readily apparent from this experiment that the amount of the SeM protein is substantially more in the bacterial strain, MGN-4598 (pMEG-573), with the RAV pMEG-573 than present in any of the other host-vector strains. Given that all plasmids in these strains contain the same SeM coding region found in pMEG-375, and that the level of SeM expression obtain is not detectable on the Coomassie gel with any of the other strong promoters tested in MGN-4598 (pMEG-825) P22 $P_R$, MGN-4598 (pMEG-826) $P_{trc}$ or-2238 (pMEG-575) λ$P_L$ (all on pBR based plasmids), only the RAV constructs were ever evaluated in animals.

The immunogenic properties of the RAV SeM vaccine strains were initially evaluated in BALB/c mice given ~$10^7$ CFU of each strain intranasally on day 0 and day 28 without anesthesia. Only low levels (<1,000 CRU) of vaccine strains were recovered from the Lungs and Peyer's patches of the immunized mice 72 hours following immunization and similarly were rarely detected in feces of the immunized mice following day 3. The serological IgG SeM specific antibody response detected indicated that all strains induced strong antibody immune responses to the SeM antigen as indicated in Table 4.

TABLE 4

Average Serum IgG Immune Responses to SeM Induced by RAV SeM Vaccine Strains in Mice ELISA Readings at 1/100 Dilution of Sera

| Strain | Day 14 (pos. mice) | Day 35 (pos. mice) | Day 41 (pos. mice) |
|---|---|---|---|
| MGN-2238 (pMEG-573) | 0.319 (1/4) | 1.209 (4/4) | 1.003 (4/4) |
| MGN-4598 (pMEG-573) | 0 | 1.846 (4/4) | 1.858 (4/4) |
| MGN-4598 (pMEG-573) Ara+ transductant | 0 | 0.924 (4/4) | 1.296 (4/4) |

TABLE 4-continued Average Serum IgG Immune Responses to SeM
Induced by RAV SeM Vaccine Strains in Mice
ELISA Readings at 1/100 Dilution of Sera

| Strain | Day 14 (pos. mice) | Day 35 (pos. mice) | Day 41 (pos. mice) |
|---|---|---|---|
| MGN-4598 (pMEG-546) Vector Only | 0.040 | 0.073 | 0.075 |

Based on this information, horse studies were then conducted using the same strains administered to horses to evaluate the serological immune responses-to the SeM antigen in the target animal. Horses were immunized on days 0 and 14 with ~$10^8$ CFU of each of the strains indicated. Sera and nasal washings were then collected and evaluated for SeM specific antibodies as indicated in Table 5 and Table 6. The data revealed higher backgrounds for the SeM antigen in many of the horses being evaluated than seen in mice, and also greater variation in the immune responses to SeM between different animals; however, there is still a clear serum IgG response in three of the MGN4598 (pMEG-573) Ara+ transductant immunized horses and 1 of the MGN4598 (pMEG-573) immunized horses. Nasal wash IgA responses to SeM (Table 6) are similar in that there is a high SeM background in the horses prior to immunization, while two of the MGN4598 (pMEG-573) Ara+ transductant immunized horses and three of the MGN4598 (pMEG-573) immunized horses appear to have IgA responses to SeM. Both the mouse studies and the horse studies support the use of RAV based SeM vaccines for intranasal immunization with or without the modification of the strains to eliminate the ability to utilize arabinose.

TABLE 5

Average Serum IgG Immune Responses to SeM
Induced by RAV SeM Vaccine Strains in Horses
ELISA Readings at 1/10,000 Dilution of Sera

| Strain | Horse | Day 0 | Day 28 |
|---|---|---|---|
| MGN-4598 (pMEG-573) | Lyon#1 | 0.134 | 0.156 |
|  | CB1 | 0.968 | 0.853 |
|  | 949 | 0.488 | 0.944 |
|  | 9802 | 0.250 | 0.343 |
| MGN-4598 (pMEG-546) Vector Only | Lyon#2 | 0.273 | 0.328 |
|  | Lyon#3 | 00.317 | 0.229 |
|  | P13 in RAV expression because of inclusion of the c2 repressor gene on the RAV vector and because of the inclusion of mutations 1 and 2, 3, 5 or 6 and 7 and either 8 or 9 (FIG. 2) in the host chromosome so that the vaccine strain will have sufficient time and growth opportunities in the absence of arabinose to attach to, invade, and colonize lymphoid organs, whether administered intranasally or orally to animals or humans.

Example 6

Circular plasmid DNA, so called transfer plasmids, encoding antigens of various pathogens can be introduced into animal hosts to stimulate the induction of immunity to the pathogen from which the antigen gene was derived (Ullmer et al., *ASM News* 62:476-479, 1996; Ullmer et al., *Curr. Opin. Immunol.* 8:531-536, 1996; Whalen, *Emerg. Infect. Dis.* 2:168-175, 1996; Robinson, *Vaccine* 15:785-787, 1997). DNA vaccines make use of expression systems such that the genetic information specifying the antigen of some pathogen is expressed by the immunized hosts using host machinery for transcription and translation. This may be particularly important for expression of viral, fungal and parasite antigens which are often glycosylated but only when synthesized in a eukaryotic host and never when expressed in a prokaryotic host such as an attenuated bacterial antigen delivery host. Initially, DNA vaccines where administered by injection into muscle tissue, but other injection sites have also been used. Most recently, DNA vaccines have been administered using particle guns to accelerate entry of DNA-coated gold beads into skin or mucosal tissues. The DNA vaccine vectors are propagated in and isolated from recombinant *E. coli* strains grown in fermentors.

Sizemore et al. (*Science,* 270:299-302, 1995; *Vaccine* 15:804-807, 1997) described the use of *Shigella flexneri* 2 a strain 15D with a Δasd mutation that harbored a DNA vaccine vector engineered to express *E. coli* β-galactosidase. The Shigella strain was attenuated due to the Δasd mutation which causes death due to absence of diaminopimelic acid upon invasion into eukaryotic cells. The strain was able to deliver the DNA vaccine vector intracellularly after attachment to, invasion into and lysis within the cytoplasm of eukaryotic cells in culture or within immunized mice. More recently, others have used *S. typhimurium* strains possessing a DNA vaccine vector and caused to lyse by spontaneous or animal host-dependent means (Powell et al., WO96/34631, 1996; Pascal et al., *Behring. Inst. Mitt.* 98:143-152, 1997; Datji et al., *Cell* 91:765-775, 1997). In cases in which lysis was spontaneous, it was necessary that the bacterial strain possess one or more deletion mutations rendering the strain attenuated. *Shigella, Salmonella* and invasive *E. coli* are known to have a much enhanced ability to attach to and invade M cells overlying the GALT rather than to attach to and invade intestinal epithelial cells (enterocytes). Delivery of foreign antigens or the production of foreign antigens within the NALT, BALT, CALT and GALT, which all have a M cell layer leads to induction of mucosal immune responses as well as systemic immunity. Because mucosal immune responses are protective against the vast majority of infectious disease agents that colonize on or invade through a mucosal surface, it would be expected that DNA vaccine vectors could thus be delivered by *Salmonella, Shigella, Escherichia* or hybrids between any two of these genera. These microbes would have a superior ability to attach to and invade the M cells overlying the lymphoid tissues of the NALT, CALT, BALT and GALT where they would then gain access to antigen presenting cells, such as macrophages and dendritic cells. Since immune responses are more or less proportional to the dose of antigen to which the immunized individual is exposed, it would be expected that means for delivering DNA vaccine vectors that would increase the number of copies of the coding sequence for the foreign antigen to be expressed within a eukaryotic cell would be beneficial in maximizing the immune response induced. Indeed, only about 2% of eukaryotic cells that receive a DNA vaccine vector functionally express the gene product encoded by the foreign gene inserted into the DNA vaccine vector. Thus, the use of an attenuated RADS that would deliver a runaway vector modified for expression of an inserted foreign gene only within eukaryotic cells and not within prokaryotic cells would significantly improve the efficacy of DNA vaccine vector immunization.

In the past, we have employed DNA vaccine vectors: derived from both pCMV β and pVAX-1 that are commercially available and have replaced the drug resistance gene with the *S. typhimurium* asd gene to alleviate the concern for introducing antibiotic resistance genes as parts of vaccines into immunized animal and human hosts. In the present case, however, it becomes important to design the RADS with RAV so that the system upon runaway amplification of the plasmid vector will undergo lysis within eukaryotic cells within the immunized animal host. Therefore, the plasmid vector depicted in FIG. 12 and described in Example 5, which possesses an araC$P_{BAD}P^{22}c^2$ SDGTG asd cassette will serve as the starting plasmid construct. This RAV's maintenance within bacterial cells that possesses a mutation 1 (FIG. 2), that is the ΔasmA19:araC$P_{BAD}c^2$ mutation/insertion, is dependent on growth in the presence of arabinose. In the absence of arabinose runaway replication commences, but also cessation of synthesis of Asd enzyme, which leads to a weakened cell wall due to inability to synthesize DAP. The pool of DAP is also rapidly depleted by conversion of DAP to lysine needed for protein synthesis. It should be pointed out that the number of Asd enzyme molecules produced in the bacterial cell with the plasmid depicted in FIG. 12 is just adequate to maintain viability in the absence of added DAP. This is because of the low efficiency of translation of the asd coding sequence due to the GTG start codon. To construct a transfer vector suitable for use as a transfer RAV, the $P_{TRC}$ MCS 5S T1T2 transcription terminator cassette is removed and replaced with the pCMV MCS bovine growth hormone polyadenylation specification from the commercially available DNA vaccine vector pVAX-1. The resulting transfer vector derived from the modified pMEG-771 is depicted in FIG. 22. This transfer RAV can be introduced into various attenuated bacterial strains to generate a RADS. The bacterial host strain would possess mutations 1 and 2 (FIG. 2) and, depending upon the desired level of delay in phenotypic expression of runaway replication, mutations 3, 5 or 6 and 7 (FIG. 2). In order to attenuate the bacterial host strain, one could include attenuating mutations, such as mutations 8 or 9 (FIG. 2), although one could use any of a diversity of other attenuating mutations. When bacteria lyse to liberate transfer vectors, such as the transfer RAV depicted in FIG. 22, the endonuclease I present in the periplasmic space is encountered and this enzyme can cleave circular plasmid DNA into linear fragments, which are then subject to exonucleolytic digestion. We therefore have cloned the endA gene encoding endonuclease I from *S. typhimurium*, SL1344 strain χ3339 generated a defined internal deletion and constructed a suicide vector designated pMEG-776 depicted in FIG. 23. This suicide vector has all of the features of pMEG-375 (FIG. 3)

from which pMEG-776 was derived, and enables one skilled in the art using-methods described above to introduce by allele replacement the ΔendA mutation into the chromosome of bacterial host strains to be used for delivery of transfer RADs.

The transfer RAV in FIG. 22 would be modified to insert a sequence encoding a foreign antigen using the multiple cloning site (MCS) after the $P_{cmv}$ promoter. The genes for these foreign antigens would be preferably from viral, fungal and parasitic pathogens, whose expression within a eukaryotic host may benefit from the post-translational modification machinery of the eukaryotic host. This is particularly important with regard to protective antigens that would be subject to such post-translational modification such as by glycosylation.

The foreign antigen encoding transfer vector of the type depicted in FIG. 22 could also be produced by a nonattenuated bacterial host, such as an *E. coli* strain only possessing mutations 1 and 2 (FIG. 2) but also with the endA3 mutation to eliminate the presence of endonuclease I in the periplasmic space. This construct could be grown in a fermentor in the presence of arabinose and runaway replication would occur following removal and/or complete utilization of arabinose to generate very high quantities of plasmid DNA, which could be harvested and used as a DNA vaccine to be delivered by injection, particle gun, etc. as described above. An important feature, is the absence of antibiotic resistance genes which would thereby preclude the possibility for contamination of the DNA vaccine with antibiotics used during the propagation of the bacteria within a fermentor.

Another important benefit of the type of DNA vaccine vector depicted in FIG. 22 is the presence of unique CpG sequences that have been shown to enhance immune responses (Krieg, *J. Lab. Clin. Med.* 128: 128-133, 1996). Research in many labs has found that certain CpG sequences are particularly important for stimulating B cell responses leading to high antibody production. In this regard, the antibiotic resistance gene for kanamycin, which is contained in many DNA vaccine vectors, lacks any of these preferred CpG sequences. On the other hand, the *S. typhimurium* asd gene, which is included in the vectors described herein, possesses two natural CpG sequences that strongly enhance the immunogenicity of the DNA vaccine vector. In addition, the P22 c2 gene sequence contains an additional two natural CpG sequences that also strongly enhance the immunogenicity of the DNA vaccine vector. Thus, the transfer RAV depicted in FIG. 22 has numerous features to enhance the immunogenicity of foreign genes cloned into the vector and expressed in eukaryotic cells within the immunized animal host. The use of the *S. typhimurium* asd gene in such DNA vaccine vectors is described in U.S. Pat. No. 5,840,483.

All references cited in this specification are hereby incorporated in their entirety by reference. The discussion of the references herein is intended merely to summarize the assertions made by their authors and no admission is made that any reference constitutes prior art. Applicant reserves the right to challenge the accuracy and pertinence of the cited references.

A deposit of a microorganism bearing plasmid pMEG-771 was made on Jun. 10, 2003 under the terms of the Budapest Treaty with the American Type Culture Collection, Manassas, Va. 20110-2209, and has been assigned accession number PTA-5256.

What is claimed is:

1. A microorganism comprising a regulated antigen delivery system (RADS), wherein the RADS comprises:
    (a) a vector comprising (1) a gene encoding a desired gene product operably linked to a second control sequence; (2) a first origin of replication (ori) conferring vector replication using DNA Polymerase III; and (3) a second ori conferring vector replication using DNA Polymerase I,
    wherein the second ori is operably linked to a first control sequence repressible by a first repressor, and wherein the runaway vector does not comprise a phage lysis gene; and
    (b) a gene encoding a first repressor operably linked to a first activatible control sequence, wherein said microorganism additionally comprises a balanced lethal host vector system comprising a lack of a functioning essential gene, wherein the essential gene is a gene necessary for synthesis of essential cell wall constituent diaminopimelic acid (DAP), on the chromosome and the presence of a recombinant functioning copy of the essential gene on the vector.

2. The microorganism of claim 1, wherein the essential gene is an asd gene.

3. The microorganism of claim 2, wherein the asd gene is inactivated by the insertion of a repressor gene operably linked to araCP$_{BAD}$.

4. The microorganism of claim 1, further comprising an inactivating mutation in a native gene selected from the group consisting of cya, crp, phoPQ, ompR, galE, cdt, hemA, aroA, aroC, aroD and htrA.

5. The microorganism of claim 1, wherein the first ori is pSCori, and the second ori is a pUC ori.

6. The microorganism of claim 1, wherein the first control sequence is P22 P$_R$ and the first repressor is C2 repressor.

7. The microorganism of claim 1, wherein the second control sequence is P$_{trc}$ and wherein the second control sequence is repressible by a second repressor, and wherein the second repressor is a LacI repressor.

8. The microorganism of claim 7, wherein the first control sequence is P22 P$_R$; the first repressor is C2 repressor; the first on is a pSC ori, and the second ori is a pUC ori.

9. The microorganism of claim 8, wherein the vector is a pMEG-771 with a gene encoding an antigen.

10. The microorganism of claim 1, wherein the gene encoding the desired gene product is operably linked to a eukaryotic control sequence.

11. The microorganism of claim 1, which exhibits delayed RADS characteristics, wherein the delayed RADS characteristics are conferred by an alteration selected from the group consisting of: mutations that delay the loss of activator molecules by metabolism and/or leakage, a mutation or insertion to increase repressor concentration, and inclusion of a vector control sequence with binding sites for more than one repressor and/or vector sequences encoding repressor molecules that act on a vector control sequence.

12. A method of producing a desired gene product, comprising, in order,
(a) engineering a gene encoding the desired gene product into the vector in the microorganism of claim 1, wherein the microorganism comprises control sequences that repress expression of the second ori under a first condition, but in which the expression of the second oil is derepressed under a second environmental condition;
(b) culturing the microorganism of step (a) under the first environmental condition; and
(c) culturing the microorganism with runaway vector of step (a) under the second environmental condition for a time sufficient to produce the desired gene product.

13. The method of claim 12, wherein the desired gene product is an antigen.

14. The method of claim 13, wherein the first environmental condition comprises the presence of arabinose and the second environmental condition comprises the absence of arabinose.

15. The method of claim 14, wherein the first environmental condition comprises in vitro culture conditions and the second environmental condition comprises conditions inside of a vertebrate.

16. The method of claim 15, wherein
(a) the first ori is a PSC ori;
(b) the secorid ori is a pUC ori, which is operably linked to a repressing coritrol sequence corisisting of P22P$_R$;
(c) the product coritrol sequence is P$_{trc}$;
(d) the microorganism comprises a gene encoding a first repressor operably linked to a first activatible control sequence, wherein the first repressor is C2; and
(e) the microorganism comprises a gene encoding a secorid repressor operably linked to a second activatible control sequence, wherein the second repressor is LacI;
(f) the microorganism comprises a chromosome without a functiorial asd gene and the runaway vector comprises a functiorial asd gene; and
(g) the microorganism comprises an inactivating mutation in the native gene selected from the group consisting of cya, crp phoPQ, ompR, galE, cdt, hemA, arcA, aroC, aroD, and htr.

17. The method of claim 16, wherein the first envirorimental condition comprises the presence of arabinose and the second envirorimental condition comprises the absence of arabinose.

18. The method of claim 17, wherein the microorganism further comprises an inactivating deletiori in the araCBAD operori and/or the araE gene.

19. The method of claim 18, wherein the desired gene product is selected from the group corisisting of Ery65 and SeM.

20. The method of claim 18, wherein the gene encoding the desired gene product is operably linked to a eukaryotic control sequence.

21. A method of delivering a desired gene product to a vertebrate comprising administering the microorganism of claim 1 to the vertebrate.

22. The microorganism of claim 2, wherein the microorganism is a *Salmonella sp.*

23. The microorganism of claim 2, wherein the first activatible control sequence is araCP$_{BAD}$.

* * * * *

SEQUENCE LISTING

```
<160> NUMBER OF SEQ ID NOS: 2

<210> SEQ ID NO 1
<211> LENGTH: 31
<212> TYPE: DNA
<213> ORGANISM: Artificial
<220> FEATURE:
<223> OTHER INFORMATION: PCR primer SeM444-474

<400> SEQUENCE: 1
gcgaactctg aggttagtcg tacggcgact c                              31

<210> SEQ ID NO 2
<211> LENGTH: 33
<212> TYPE: DNA
<213> ORGANISM: Artificial
<220> FEATURE:
<223> OTHER INFORMATION: PCR Primer SeM1265-1233

<400> SEQUENCE: 2
ttgatcaatt tctgctaatt tttgagccat ttc                            33
```